US008597922B2

(12) United States Patent
Alibhai et al.

(10) Patent No.: US 8,597,922 B2
(45) Date of Patent: Dec. 3, 2013

(54) METHODS AND COMPOSITIONS FOR PRODUCING OLEFINS

(75) Inventors: Murtaza F. Alibhai, Austin, TX (US); Mathew A. Rude, South San Francisco, CA (US); Andreas W. Schirmer, South San Francisco, CA (US)

(73) Assignee: LS9, Inc., South San Francisco, CA (US)

( * ) Notice: Subject to any disclaimer, the term of this patent is extended or adjusted under 35 U.S.C. 154(b) by 0 days.

(21) Appl. No.: 13/452,449

(22) Filed: Apr. 20, 2012

(65) Prior Publication Data

US 2012/0253088 A1    Oct. 4, 2012

Related U.S. Application Data

(62) Division of application No. 12/673,752, filed as application No. PCT/US2008/014029 on Dec. 22, 2008, now Pat. No. 8,183,028.

(60) Provisional application No. 61/016,183, filed on Dec. 21, 2007, provisional application No. 61/051,886, filed on May 9, 2008, provisional application No. 61/092,378, filed on Aug. 27, 2008.

(51) Int. Cl.
*C12N 1/20* (2006.01)
*C12P 5/02* (2006.01)

(52) U.S. Cl.
USPC ........ 435/167; 536/23.2; 435/252.3; 435/232

(58) Field of Classification Search
USPC ................................. 435/232, 167
See application file for complete search history.

(56) References Cited

U.S. PATENT DOCUMENTS

| | | | |
|---|---|---|---|
| 5,233,109 | A | 8/1993 | Chow |
| 6,982,155 | B1 * | 1/2006 | Fukuda et al. ............ 435/135 |
| 7,118,896 | B2 | 10/2006 | Kalscheuer et al. |
| 2003/0040474 | A1 | 2/2003 | Kapeller-Libermann et al. |
| 2003/0097686 | A1 | 5/2003 | Knauf et al. |
| 2003/0129601 | A1 | 7/2003 | Cole |
| 2004/0009576 | A1 | 1/2004 | Kalscheuer et al. |
| 2004/0159537 | A1 | 8/2004 | Maeda et al. |
| 2004/0197896 | A1 | 10/2004 | Cole |
| 2005/0250135 | A1 | 11/2005 | Klaenhammer et al. |
| 2006/0014977 | A1 | 1/2006 | Miller et al. |
| 2007/0251141 | A1 | 11/2007 | Bist et al. |
| 2007/0261138 | A1 | 11/2007 | Graham et al. |
| 2007/0270319 | A1 | 11/2007 | Seggelkow et al. |
| 2008/0161595 | A1 | 7/2008 | Huang et al. |
| 2008/0271364 | A1 | 11/2008 | Wiesman et al. |
| 2008/0295388 | A1 | 12/2008 | Bazzani et al. |
| 2009/0038211 | A1 | 2/2009 | Sarin et al. |
| 2009/0084025 | A1 | 4/2009 | Bhatia et al. |
| 2010/0071259 | A1 | 3/2010 | Hu et al. |
| 2010/0154293 | A1 | 6/2010 | Hom et al. |
| 2010/0199548 | A1 | 8/2010 | Del Cardayre et al. |
| 2010/0242345 | A1 | 9/2010 | Keasling et al. |
| 2010/0251601 | A1 | 10/2010 | Hu et al. |
| 2010/0257778 | A1 | 10/2010 | Gaertner et al. |
| 2010/0274033 | A1 | 10/2010 | Sanchez-Riera et al. |
| 2011/0072714 | A1 | 3/2011 | Gaertner et al. |
| 2011/0162259 | A1 | 7/2011 | Gaertner et al. |
| 2012/0253088 | A1 * | 10/2012 | Alibhai et al. ............. 585/16 |

FOREIGN PATENT DOCUMENTS

| | | |
|---|---|---|
| DE | 10 2004 052115 A1 | 4/2006 |
| WO | WO 2006/072256 A2 | 7/2006 |
| WO | WO 2007/136762 A2 | 11/2007 |
| WO | WO 2008/119082 A2 | 10/2008 |
| WO | WO 2009/042950 A1 | 4/2009 |
| WO | WO 2010/022090 A1 | 2/2010 |
| WO | WO 2010/075483 A2 | 7/2010 |
| WO | WO 2010/118410 A1 | 10/2010 |
| WO | WO 2010118409 A1 | 10/2010 |
| WO | WO 2010126891 A1 | 11/2010 |
| WO | WO 2011/038132 A1 | 3/2011 |

OTHER PUBLICATIONS

Nishio et al. [Genome Research, 13:1572-1579 (2003)].*
Abbadi et al., "Knockout of the regulatory site of 3-ketoacyl-ACP synthase III enhances short-and medium-chain acyl-ACP synthesis", *Plant Journal*, 24(1): 1-9 (2000).
Abdel-Hamid et al., "Pyruvate oxidase contributes to the aerobic growth efficiency of *Escherichia coli*," *Microbiology*, 147(6): 1483-98 (2001).
Abdel-Hamid et al., "Coordinate Expression of the Acetyl Coenzyme A Carboxylase Genes, accB and accC, Is Necessary for Normal Regulation of Biotin Synthesis in *Escherichia coli*", *J. Bacteriol.*, 189:369-376 (2007).
Alper, et al., "Engineering for biofuels: exploiting innate microbial capacity or importing biosynthetic potential?", *NRM* 7: 715-723 (2009).
Antoni, et al., "Biofuels from microbes", *Appl. Microbiol. Biotechnol.*, 77: 23-35 (2007).
Atsumi et al., "Metabolic engineering for advanced biofuels production from *Escherichia coli*", *Current Opin.Biotech*, 19:414-419 (2008).
Atsumi et al., "Metabolic engineering of *Escherichia coli* for 1-butanol production", *Metabolic Enginering* 10:305-311 (2008).
Barnes, Jr. et al., "Studies on the Mechanism of Fatty Acid Synthesis. XIX. Preparation and General Properties of Palmityl Thioesterase", *J. Biol. Chem.*, 243(11):2955-2962 (1968).
Beekwilder et al., "Functional Characterization of Enzymes Forming Volatile Esters from Strawberry and Banana", *Plant Physiology*, 135: 1865-1878 (2004).
Birge et al., "Acyl Carrier Protein. XVI.Intermediate Reactions of Unsaturated Fatty Acid Synthesis in *Escerichia coli* and Studies of fab B Mutants", *J.Biol.Chem*. 247(16): 4921-4929 (1972).

(Continued)

*Primary Examiner* — Tekchand Saidha
(74) *Attorney, Agent, or Firm* — Brigitte A. Hajos

(57) ABSTRACT

Compositions and methods for producing olefins are described herein. The olefins can be used to produced biofuels.

21 Claims, 46 Drawing Sheets

(56) References Cited

OTHER PUBLICATIONS

Black et al., "Cloning, Sequencing, and Expression of the fadD Gene of *Escherichia coli* Encoding Acyl Coenzyme A Synthetase," *J. Biol. Chem.* 267(35): 25513-25520 (1992).
Black, P., "Primary Sequence of the *Escherichia coli* fadL Gene Encoding an Outer Membrane Protein Required for Long-Chain Fatty Acid Transport", *J. Bacteriololgy* 173(2): 435-442 (1991).
Black et al., "Mutational Analysis of a Fatty Acyl-Coenzyme A Synthetase Signature Motif Identifies Seven Amino Acid Residues That Modulate Fatty Acid Substrate Specificity", *J. Biol. Chem.* 272(8) 4896-4903 (1997).
Black et al., "Long-Chain Acyl-CoA-Dependent Regulation of Gene Expression in Bacteria, Yeast and Mammals", *J. Nutrition*, 305S-309S (2000).
Blanchard et al., "Overexpression and Kinetic Characterization of the Carboxyltransferase Component of Acetyl-CoA Carboxylase", *J.Biol.Chem.* 273(30): 19140-19145 (1998).
Bonamore et al., "The desaturase from *Bacillus subtilis*, a promising tool for the selective olefination of phospholipids", *J.Biotechnology* 121: 49-53 (2006).
Bond-Watts et al., "Enzyme mechanism as a kinetic control element for designing synthetic biofuel pathways", *Nature Chem Bio* 537: 1-6 (Suppl. S1-S28) (2011).
Bonner et a.l, "Purification and Properties of Fatty Acyl Thioesterase I from *Escherichia coli*", *J.Biol.Chem.* 247(10): 3123-3133 (1972).
Boonstra et al., "The *udhA* Gene of *Escherichia coli* Encodes a Soluble Pyridine Nucleotide Transhydrogenase", *J.Bacteriology* 181(3): 1030-1034 (1999).
Boulanger et al., "Purification and Structrual and Functional Characterization of FhuA, a Transporter of the *Escherichia coli* Outer Membrane," *Biochemistry*, 35(45): 14216-14224 (1996).
Bunch et al., "The IdhA Gene Encoding the Fermentative Lactate Dehydrogenase of *Escherichia coli*," *Microbiology*, 143(1): 187-95 (1997).
Cahoon et al., "Modification of the Fatty Acid Composition of *Escherichia coli* by Coexpression of a Plant Acyl-Acyl Carrier Protein Desaturase and Ferredoxin", J.Bacteriology 178(3): 936-936 (1996).
Cahoon et al., "Redesign of soluble fatty acid desaturases from plants for altered substrate specificity and double bond position", *Proc. Natl. Acad. Sci.*94: 4872-4877 (1997).
Cahoon et al., "A Determinant of Substrate Specificity Predicted from the Acyl-Acyl Carrier Protein Desaturase of Developing Cat's Claw Seed", *Plant Physiol* 117: 593-598 (1998).
Campbell et al., "The Enigmatic *Escherichia coli fadE* Gene is *yafH*" *J. Bacteriol.*, 184(13): 3759-3764 (2002).
Campbell et al., "A New *Escherichia coli* metabolic competency: growth on fatty acids by a novel anaerobic β-oxidation pathway," *Mol. Microbiol.*, 47(3): 793-805 (2003).
Campbell et al,, "*Escherichia coli* FadR Positively Regulates Transcription of the fabB Fatty Acid Biosynthetic Gene", *J.Bacteriology* 183(20): 5982-5990 (2001).
Canonaco et al., "Metabolic flux response to phosphoglucose isomerase knock-out in *Escherichia coli* and impact of overexpression of the soluble transhydrogenase UdhA", *FEMS Microbiology Letters* 204: 247-252 (2001).
Carlson et al., "Fundamental *Escherichia coli* Biochemical Pathways for Biomass and Energy Production: Creation of Overall Flux States", *Biotech & Bioengineering* 86(2): 149-162 (2004).
Caviglia et al., "Rat Long Chain Acyl-CoA Synthetase 5, but Not 1,2,3, or 4, Complements *Escherichia coli fadD*," *J. Biol. Chem.*, 279(12): 11163-11169 (2004).
Chan et al., "Current understanding of fatty acid biosynthesis and the acyl carrier protein", *Biochem. J.* 430: 1-19 (2010).
Cheng et al., "Mammalian Wax Biosynthesis, II. Expression Cloning of Wax Synthase cDNAs Encoding a Member of the Acyltransferase Enzyme Family*," *J. Biol. Chem.*, 279(36): 37798-37807 (2004).
Cho et al., "Defective Export of a Periplasmic Enzyme Disrupts Regulation of Fatty Acid Synthesis," *J. Biol. Chem.*, 270: 4216-4219 (1995).

Cho et al., "*Escherichia coli* Thioesterase I, Molecular Cloning and Sequencing of the Structural Gene and Identification as a Periplasmic Enzyme", *J.Biol.Chem* 268(13:5): 9238-9245 (1993).
Cho et al., "Transcriptional regulation of the *fad* regulon genes of *Escherichia coli* by ArcA", *Microbiology* 152: 2207-2219 (2006).
Choi et al., "β-Ketoacyl-acyl Carrier Protein Synthase III (FabH) Is a Determining Factor in Branched-Chain Fatty Acid Biosynthesis" *J. of Bacteriology* 182(2): 365-370 (2000).
Coleman et al., "Enzymes of triacylglycerol synthesis and their regulation" *Progress in Lipid Research* 43:134-176 (2004).
Davis, J.B., "Microbial Incorporation of Fatty Acids Derived From n-Alkanes Into Glycerides and Waxes" *Applied Microbiology* 12(3): 210-214 (1964).
Davis et al., "Inhibition of *Escherichia coli* Acetyl Coenzyme A Carboxylase by Acyl-Acyl Carrier Protein" *J. of Bacteriology* 183(4): 1499-1503 (2001).
Davis et al., "Overproduction of Acetyl-CoA Carboxylase Activity Increases the Rate of Fatty Acid Biosynthesis in *Escherichia coli*" *J.Biol.Chem* 275(37:15) 28593-28598 (2000).
Dehesh et al., "KAS IV: A 3-ketoacyl-ACP synthase from *Cuphea* sp. Is a medium chain specific condensing enzyme", *The Plant Journal* 15(3):383-390 (1998).
Dehesh et al., "Production of high levels of 8:0 and 10:0 fatty acids in transgenic canola by overexpression of *Ch FatB2*, a thioesterase cDNA from *Cuphea* hookeriana" *The Plant Journal* 9(2): 167-172 (1996).
Delay et al., "In Vivo Functional Analyses of the Type II Acyl Carrier Proteins of Fatty Acid Biosynthesis", *J.Biol.Chem.* 282: 20319-20328 (2007).
Dellomonaco et al., "Engineered Respiro-Fermentative Metabolism for the Production of Biofuels and Biochemicals from Fatty Acid-Rich Feedstocks", *Applied & Environmental Microbiology* 76(15): 5067-5078 (2010).
Dellomonaco et al., "The path to next generation biofuels: successes and challenges in the era of synthetic biology", *Microbial Cell Factories* 9(3): 1-15 (2010).
Demendoza et al., "Thermal Regulation of Membrane Fluidity in *Escherichia coli*. Effects of Overproduction of P-Ketoacylacyl Carrier Protein Synthase 1", *J.Biol.Chem.* 258(4):2098-2101 (1983).
Demibras, A., "Relationships derived from physical properties of vegetable oil and biodiesel fuels", *Fuel* 87: 1743-1748 (2008).
Demibras, A., "Progress and recent trends in biofuels", *Progress in Energy and Combustion Science* 33: 1-18 (2007).
Doan et al., "Functional expression of five *Arabidopsis* fatty acyl-CoA reductase genes in *Escherichia coli*" *J. Plant Physiology* 166:787-796 (2009).
Domergue et al., "Acyl Carriers Used as Substrates by the Desaturases and Elongases Involved in Very Long-chain Polyunsaturated Fatty Acids Biosynthesis Reconstituted in Yeast" *J.Biol.Chem* 278(37):35115-35126 (2003).
Duan et al., "De novo Biosynthesis of Biodiesel by *Escherichia coli* in Optimized Fed-Batch Cultivation", *PLoS ONE* 6(5): 1-7 (2011).
Elbahloul et al., "Pilot-Scale Production of Fatty Acid Ethyl Esters by an Engineered *Escherichia coli* Strain Harboring the p(Microdiesel) Plasmid", *Appl. and Environ. Microbiol.* 76(13):4560-4565 (2010).
Farewell et al., "Role of the *Escherichia coli* FadR Regulator in Stasis Survival and Growth Phase-Dependent Expression of the *uspA, fad,* and *fab* Genes", *J. of Bacteriology* 178(22): 6443-6450 (1996).
Feng et al., "A New Member of the *Escherichia coli* fad Regulon: Transcriptional Regulation of *fadM* (*ybaW*)", *J. of Bacteriology* 191(20): 6320-6328 (2009).
Feng et al., "Overlapping Repressor Binding Sites Result in Additive Regulation of *Escherichia coli* FadH by FadR and ArcA" *J. of Bacteriology* 192(17):4289-4299 (2010).
Feng et al., "*Escherichia coli* Unsaturated Fatty Acid Synthesis: Complex Transcription of the fabA Gene and In Vivo Identification of the Essential Reaction Catalyzed by FabB", *J.Biol.Chem.* 284(43): 29526-29535 (2009).
Fischer et al., "Selection and optimization of microbial hosts for biofuels production" *Metabolic Engineering* 1:295-304 (2008).

(56) References Cited

OTHER PUBLICATIONS

Flaman et al., "Site-directed Mutagenesis of Acyl Carrier Protein (ACP) Reveals Amino Acid Residues Involved in ACP Structure and Acyl-ACP Synthetase Activity", *J.Biol.Chem.* 276(38): 35934-35939 (2001).

Fujita et al., "Regulation of fatty acid metabolism in bacteria", *Mol. Microbiology* 66(4): 829-839 (2007).

Heath et al., "Regulation of Malonyl-CoA Metabolism by Acyl-Acyl Carrier Protein and β-Ketoacyl-Acyl Carrier Protein Synthases in *Escherichia coli*", *J.Biol.Chem.* 270(26):15531-15538 (1995).

Heath et al., "Regulation of Fatty Acid Elongation and Initiation by Acyl-Acyl Carrier Protein in *Escherichia coli*", *J.Biol.Chem.* vol. 271(4): 1833-1836 (1996).

Heath et al., "Inhibition of β-Ketoacyl-Acyl Carrier Protein Synthase III (FabH) by Acyl-Acyl Carrier Protein in *Escherichia coli*", *J.Biol. Chem.*271(18):10996-11000 (1996).

Heath et al., "Roles of the FabA and FabZ β-Hydroxyacyl-Acyl Carrier Protein Dehydratases in *Escherichia coli* Fatty Acid Biosynthesis", *J.Biol.Chem.* 271(44): 27795-27801 (1996).

Henry et al., "*Escherichia coli* Transcription Factor That Both Activates Fatty Acid Synthesis and Represses Fatty Acid Degradation", *J. Mol. Bio E.* 222: 843-849 (1991).

Holtzapple et al., "Biosynthesis of Isoprenoid Wax Ester in Marinobacter hydrocarbonoclasticus DSM 8798: Identification and Characterization of Isoprenoid Coenzyme A Synthetase and Wax Ester Synthases", *J.Bacteriology* 189(10): 3804-3812 (2007).

Hu et al., Microalgal triacylglycerols as feedstocks for biofuel production: perspectives and advances, *The Plant Journal* 54: 621-639 (2008).

Huber et al., "Synthesis of Transportation Fuels from Biomass: Chemistry, Catalysts, and Engineering", *Chem.Rev.*106: 1-55 (2006).

Hunt et al., "Characterization of an Acyl-CoA Thioesterase That Functions as a Major Regulator of Peroxisomal Lipid Metabolism" *J.Biol.Chem.* 277(2):1128-1138 (2002).

Imahara et al., "Thermodynamic study on cloud point of biodiesel with its fatty acid composition", *Fuel* 85: 1666-1670 (2006).

Ishige et al., "Long-Chain Aldehyde Dehydrogenase That Participates in *n*-Alkane Utilization and Wax Ester Synthesis in *Acinetobacter* sp. Strain M-1", *Appl. Environ. Microbiol.* 66(8): 3481-3486 (2000).

Ishige et al., "Wax Ester Production from n-Alkanes by *Acinetobacter* sp. Strain M-1: Ultrastructure of Cellular Inclusions and Role of Acyl Coenzyme A Reductase", *Appl. Environ. Microbiol.* 68(3): 1192-1195 (2002).

Jayakumar et al., "Cloning and expression of the multifunctional human fatty acid synthase and its subdomains in *Escherichia coli*",*PNAS* 93. 14509-14514 (1996).

Jiang, et al., "Inhibition of Fatty Acid Synthesis in *Escherichia coli* in the Absence of Phospholipid Synthesis and Release of Inhibition by Thioesterase Action" *J. Bacteriology* 176(10): 2814-2821 (1994).

Jones et al., "Palmitoyl-Acyl Carrier Protein (ACP) Thioesterase and the Evolutidnary-Origin of Plant ACyl-ACP Thioesterases", *Plant Cell*, vol. 7:359-371 (1995).

Joshi et al., "Flow properties of biodiesel blends at low temperatures", *Fuel* 86. 143-151 (2007).

Kalscheuer et al., "Microdiesel: *Escherichia coli* engineered for fuel production", *Microbiol.* 152(9): 2529-2536 (2006).

Kalscheuer et al., "Neutral Lipid Biosynthesis in Engineered *Escherichia coli*: Jojoba Oil-Like Wax Esters and Fatty Acid Butyl Esters", *Appl.Environ.Microbiol.* 72(2): 1373-1379 (2006).

Kalscheuer et al., "Analysis of Storage Lipid Accumulation in *Alcanivorax* borkumensis:Evidence for Alternative Triacylglycerol Biosynthesis Routes in Bacteria," *J.Bacteriology* 189(3): 918-923 (2007).

Keasling et al., "Metabolic engineering delivers next-generation biofuels", *Nature Biotechnology* 26(3):298-299 (2008).

Knoll et al., "Biochemical Studies of Three *Saccharomyces cerevisiae* Acyl-CoA Synthetases, Faalp, Faa2p, and Faa3p," *J. Biol. Chem.*, 269(23): 16348-16356 (1994).

Knothe et al., "Kinematic viscosity of biodiesel components (fatty acid alkyl esters) and related compounds at low temperatures", *Fuel* 86: 2560-2567 (2007).

Knothe, "Designer Biodiesel: Optimizing Fatty Ester Composition to Improve Fuel Properties," *Energy & Fuels*, 22: 1358-1364 (2008).

Knothe, G., "Dependence of Biodiesel Fuel Properties on the Structure of Fatty Acid Alkyl Esters," *Fuel Process. Technol.*, 86: 1059-1070 (2005).

Knothe et al., "Kinematic viscosity of biodiesel fuel components and related compounds. Influence of compound structure and comparison to petrodiesel fuel components", *Fuel* 84:1059-1065 (2005).

Knudsen et al., "Transacylation as a chain-termination mechanism in fatty acid synthesis by mammalian fatty acid synthetase. Synthesis of medium-chain-length ($C_8$-$C_{12}$) acyl-CoA esters by goat mammary-gland fatty acid synthetase", *Biochem. J.* 202: 139-143 (1982).

Koffas, M.A.G., "Expanding the repertoire of biofuel alternatives through metabolic pathway evolution", *PNAS* 106(4): 965-966 (2009).

Kumari et al., "Regulation of Acetyl Coenzyme A Synthetase in *Escherichia coli*", *J. Bacteriology* 182(15): 4173-4179 (2000).

Lang et al., "Preparation and characterization of bio-diesels from various bio-oils", *Bioresource Tech.* 80: 53-62 (2001).

Lee et al., "Enhanced preference for π-bond containing substrates is correlated to Pro110 in the substrate-binding tunnel of *Escherichia coli* thioesterase I/protease I/lysophospholipase $L_1$" *Biochim. et Biophys. Acta*, 1774: 959-967 (2007).

Lee et al., "Metabolic engineering of microorganisms for biofuels production: from bugs to synthetic biology to fuels", *Current Opinion in Biotechnology* 19: 556-563 (2008).

Li et al., "Growth Rate Regulation of *Escherichia coli* Acetyl Coenzyme A Carboxylase, Which Catalyzes the First Committed Step of Lipid Biosynthesis", *J. of Bacteriology* 175(2): 332-340 (1993(.

Lima et al., "Diesel-Like Fuel Obtained by Pyrolysis of Vegetable Oils," *J. Analyt. Appl. Pyrolysis* 45(5): 987-996 (2004).

Link et al., "Methods for Generating Precise Deletions and Insertions in the Genome of Wild-Type *Escherichia coli*: Application to Open Reading Frame Characterization", *J.Bacteriology* 179(20): 6228-6237 (1997).

Liu, et al., "Production and secretion of fatty acids in genetically engineered cyanobacteria" *PNAS Early Edition*: 1-6 (2010).

Lu et al., "Overproduction of free fatty acids in *E. coli*: Implications for biodiesel production", *Metabolic Engineering* 10: 333-339 (2008).

Lykidis et al., "Genomic Prospecting for Microbial Biodiesel Production," LBLN-301E, No. 10: 1-39 (2008).

Magnuson et al., "Regulation of Fatty Acid Biosynthesis in *Escherichia coli*" *Microbiol.Reviews* 57(3): 522-542 (1993).

Mayer et al., "Identification of amino acid residues involved in substrate specificity of plant acyl-ACP thioesterases using a bioinformatics-guided approach" *BMC Plant Biology* 7(1) (2007).

Metzgar et al., "*Acinetobacter* sp. ADP1: an ideal model organism for genetic analysis and genome engineering", *Nucleic Acid Res.* 32(19):5780-5790 (2004).

Miller et al., "A Highly Catalytic and Selective Conversion of Carboxylic Acids to 1-Alkenes of One Less Carbon Atom," *J. Org. Chem*, 58(1): 18-20 (1993).

Morgan-Kiss et al, "The *Escherichia coli fadK* (*ydiD*) Gene Encodes an Anerobically Regulated Short Chain Acyl-CoA Synthetase," *J. Biol. Chem.*, 279(36): 37324-37333 (2004).

Morgan-Kiss et al., "The *Lactococcus lactis* FabF Fatty Acid Synthetic Enzyme can Functionally Replace both the FabB and FabF Proteins of *Escherichia coli* and the FabH Protein of *Lactococcus lactis*," *Arch. Microbiol.* 190: 427-437 (2008).

Morrison et al., "Neutral Lipids in the Study of Relationships of Members of the Family *Micrococcaceae*", *J.Bacteriol.*: 108(1):353-358 (1971).

Peng et al., "Effect of *fadR* gene knockout on the metabolism of *Escherichia coli* based on analyses of protein expressions, enzyme activities and intracellular metabolite concentrations" *Enzyme and Microbial Tech.* 38: 512-520 (2006).

Pillai et al., "Functional characterization of β-ketoacyl-ACP reductase (FabG) from *Plasmodium falciparum*" *Biochem. and Biophysical Research Comm.* 303: 387-392 (2003).

(56) References Cited

OTHER PUBLICATIONS

Qiu et al., "Crystal structure and substrate specificity of the β-ketoacyl-acyl carrier protein synthase III (FabH) from *Staphylococcus aureus*", *Protein Science* 14: 2087-2094 (2005).

Rawlings et al., "Biosynthesis of fatty acids and related metabolites", *Natural Product Reports* 15: 275-308 (1998).

Ray et al., "Activation of long chain fatty acids with acyl carrier protein: Demonstration of a new enzyme, acyl-acyl carrier protein synthetase, in *Escherichia coli*" *PNAS* 73(12):4374-4378 (1976).

Rehm et al., "Heterologous expression of the acyl-acyl carrier protein thioesterase gene from the plant *Umbellularia californica* mediates polyhydroxyalkanoate biosynthesis in recombinant *Escherichia coli*", *Applied Microbiology and Biotechnology* 55: 205-209 (2001).

Romero et al., "Metabolic Engineering of *Bacillus subtilis* for Ethanol Production: Lactate Dehydrogenase Plays a Key Role in Fermentative Metabolism", *Applied & Environmental Microbiology*, 73(16): 5190-5198 (2007).

Rude et al., "New microbial fuels: a biotech perspective", *Current Opinion in Microbiology* 12: 274-281 (2009).

Rude et al., "Terminal Olefin (1-Alkene) Biosynthesis by a Novel P450 Fatty Acid Decarboxylase from *Jeotgalicoccus* Species", *Appl. Environ. Microbiol.* 77(5): 1718-1727 (2011).

Salas et al., "Characterization of substrate specificity of plant FatA and FatB acyl-ACP thioesterases", *Archives of Biochem. and Biophysics* 403: 25-34 (2002).

Schweizer et al., "Microbial Type I Fatty Acid Synthases (FAS): Major Players in a Network of Cellular FAS Systems", *Microbiol. Mol. Biol. Rev.* 68(3): 501-517 (2004).

Shahid et al., "A review of biodiesel as vehicular fuel", Renew. Sustain. Ener. Reviews 12: 2484-2494 (2008).

Spencer et al., "Thioesterases I and II of *Escherichia coli*. Hydrolysis of Native Acyl-Acyl Carrier Protein Thioesters," *J. Biol. Chem.*, 253(17): 5922-5926 (1978).

Stafford et al., "Optimizing bioconversion pathways through systems analysis and metabolic engineering", PNAS 99(4): 1801-1806 (2002).

Steen et al., "Microbial production of fatty-acid-derived fuels and chemicals from plant biomass", *Nature* 463:559-563 (2010).

Stöveken et al., "The Wax Ester Synthase/Acyl Coenzyme A:Diacylglycerol Acyltransferase from *Acinetobacter* sp. Strain ADP1: Characterization of a Novel Type of Acyltransferase", *J. Bacteriology* 187(4):1369-1376 (2005).

Subrahmanyam et al., "Overproduction of a Functional Fatty Acid Biosynthetic Enzyme Blocks Fatty Acid Synthesis in *Escherichia coli*" *J. Bacteriology* 180(17):4596-4602 (1998).

Thorpe et al., "Structure and mechanism of action of the Acyl-CoA dehydrogenases1", *FASEB J.* 9: 718-725 (1995).

Tong et al., "Acetyl-Coenzyme A Carboxylases: Versatile Targets for Drug Discovery", *J. Cellular Biochem.* 99: 1476-1488 (2006).

Toomey et al., "Studies on the Mechanism of Fatty Acid Synthesis XVI. Preparation and General Properties of Acyl-Malonyl Acyl Carrier Proteincondensing Enzyme From *Escherichia coli*", *J. Biol. Chem.* 241(5):1159-1165 (1996).

Tsay et al., "Isolation and Characterization of the β-Ketoacyl-acyl Carrier Protein Synthase I11 Gene (*fabH*) from *Escherichia coli* K-12", *J. Biol. Chem.* 267(10): 6807-6814 (1992).

Twaiq et al., "Performance of composite catalysts in palm oil cracking for the production of liquid fuels and chemicals", *Fuel Processing Technology*, 85: 1283-1300 (2004).

UniProt accession No. Q325A2 "Subname: Full=Acyl-CoA thioesterase I" (2005).

Vadali et al., "Cofactor engineering of intracellular CoA/acetyl-CoA and its effect on metabolic flux redistribution in *Escherichia coli*" *Metabolic Engineering* 6: 133-139 (2004).

Vanderhoeven et al., "Biosynthesis and Elongation of Short- and Medium-Chain-Length Fatty Acids", Plant Physiology 122: 275-282 (2000).

Wackett, "Microbial-based motor fuels: Science and technology", *Microbial Biotech*: 1-15 (2008).

Yoo et al., "Determination of the native form of FadD, the *Escherichia coli* fatty acyl-CoA synthetase, and characterization of limited proteolysis by outer membrane protease OmpT", *Biochem. J.* 360: 699-706 (2001).

Zhang, et al. "The FabR (YijC) Transcription Factor Regulates Unsaturated Fatty Acid Biosynthesis in *Escherichia coli*," *J. Biol. Chem.*, 277(18): 15558-15565 (2002).

Zhang et al., "Inhibiting Bacterial Fatty Acid Synthesis", *J. Biol. Chem.* 281(26): 17541-17544 (2006).

Zhang et al., "Structural Basis for Catalytic and Inhibitory Mechanisms of β-Hydroxyacyl-acyl Carrier Protein Dehydratase (FabZ)", *J. Biol. Chem.* 283(9):5370-5379 (2008).

Zhang, et al. "Molecular effect of FadD on the regulation and metabolism of fatty acid in *Escherichia coli*," *FEMS Microbiol. Lett.*, 259(2): 249-253 (2006).

Zhu et al., "Functions of the *Clostridium acetobutylicium* FabF and FabZ proteins in unsaturated fatty acid biosynthesis", *BMC Microbiology* 9:119 (2009).

Zimhony et al., "Characterization of *Mycobacterium smegmatis* Expressing the *Mycobacterium tuberculosis* Fatty Acid Synthase I (fas1) Gene", *J. Bacteriology* 186(13): 4051-4055 (2004).

ISR and WO from PCT/US2007/011923, mailed Feb. 22, 2008.
ISR and WO from PCT/US2008/058788, mailed Jan. 27, 2009.
ISR and WO from PCT/US2008/069075, mailed Jan. 30, 2009.
ISR from WO PCT/US2008/014209, mailed May 29, 2009.
ISR from WO PCT/US2009/054209, mailed Dec. 10, 2010.
ISR from WO PCT/US09/069356, mailed Jul. 29, 2010.
ISR from WO PCT/US2010/030655, mailed Jul. 14, 2010.
ISR from WO PCT/US2010/032580, mailed Jul. 6, 2010.
ISR from WO PCT/US2009/054213, mailed Oct. 6, 2009.
ISR from WO PCT/US2009/004734, mailed Nov. 17, 2009.
ISR from WO PCT/US2010/050026, mailed Jan. 6, 2011.
ISR from WO PCT/US2010/030656, mailed Jul. 23, 2010.

\* cited by examiner

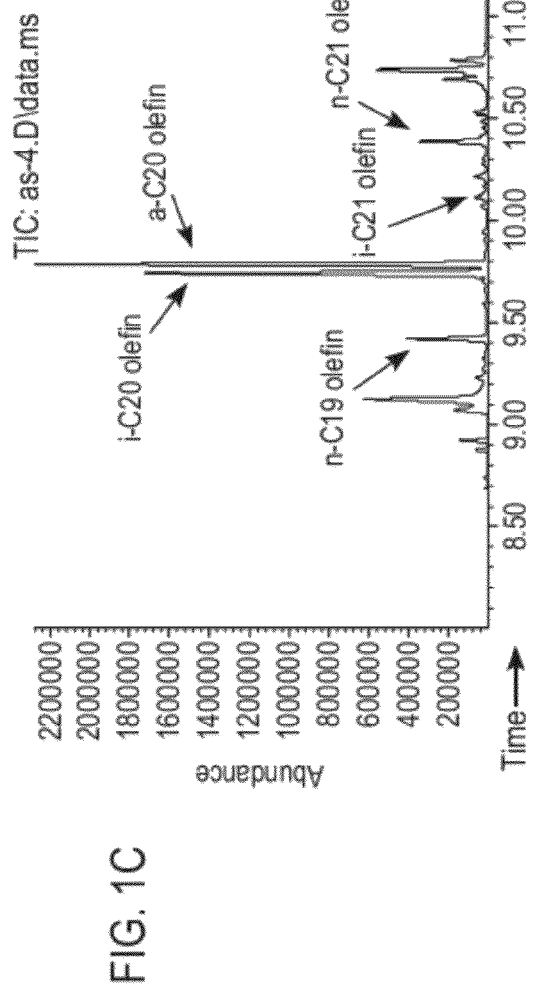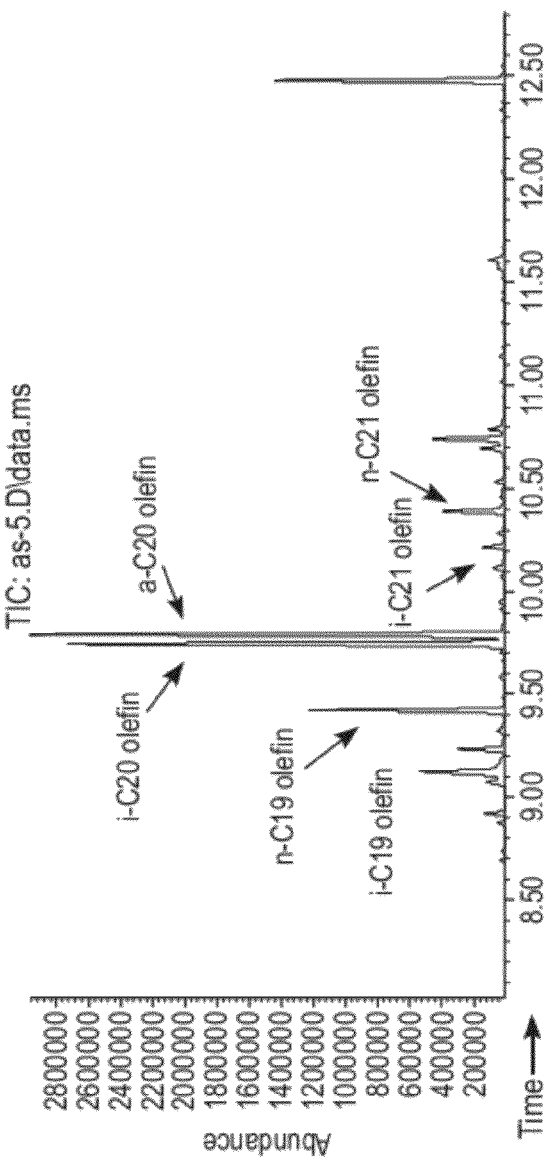
FIG. 1C
FIG. 1D

*Jeotgalicoccus sp.* ATCC8456 orf880 (SEQ ID NO:1)

```
  60   ATGCAACAC TTAAGAGGGA TAAGGGCTTA GATAATACTT TGAAAGTATT AAAGCAAGGT
 120   TATCTTTACA CAACAAATCA GAGAAATCGT CTAAACACAT CAGTTTTCCA AACTAAAGCA
 180   CTCGGTGGTA AACCATTCGT AGTTGTGACT GGTAAGGAAG GCGCTGAAAT GTTCTACAAC
 240   AATGATGTTG TTCAACGTGA AGGCATGTTA CCAAAACGTA TCGTTAATAC GCTTTTTGGT
 300   AAAGGTGCAA TCCATACGGT AGATGGTAAA AAACACGTAG ACAGAAAAGC ATTGTTCATG
 360   AGCTTGATGA CTGAAGGTAA CTTGAATTAT GTACGAGAAT TAACGCGTAC ATTATGGCAT
 420   GCGAACACAC AACGTATGGA AGTATGGAT GAGGTAAATA TTTACCGTGA ATCTATCGTA
 480   CTACTTACAA AAGTAGGAAC ACGTTGGGCA GGCGTTCAAG CACCACCTGA AGATATCGAA
 540   AGAATCGCAA CAGACATGGA CATCATGATC GATTCATTTA GAGCACTTGG TGGTGCCTTT
 600   AAAGGTTACA AGGCATCAAA AGAAGCACGT CGTCGTGTTG AAGATTGGTT AGAAGAACAA
 660   ATTATTGAGA CTCGTAAAGG GAATATTCAT CCACCAGAAG GTACAGCACT TTACGAATTT
 720   GCACATTGGG AAGACTACTT AGGTAACCCA ATGGACTCAA GAACTTGTGC GATTGACTTA
 780   ATGAACACAT TCCGCCCATT AATCGCAATC AACAGATTCG TTTCATTCGG TTTACACGCG
 840   ATGAACGAAA ACCCAATCAC ACGTGAAAAA ATTAAATCAG AACCTGACTA TGCATATAAA
 900   TTCGCTCAAG AAGTTCGTCG TTACTATCCA TTCGTTCCAT TCCTTCCAGG TAAAGCGAAA
 960   GTAGACATCG ACTTCCAAGG CGTTACAATT CCTGCAGGTG TAGGTCTTGC ATTAGATGTT
1020   TATGGTACAA CGCATGATGA ATCACTTTGG GACGATCCAA ATGAATTCCG CCCAGAAAGA
1080   TTCGAAACTT GGGACGGATC ACCATTTGAC CTTATTCCAC AAGGTGGTGG AGATTACTGG
1140   ACAAATCACC GTTGTGCAGG TGAATGGATC ACAGTAATCA TCATGGAAGA AACAATGAAA
1200   TACTTTGCAG AAAAAATAAC TTATGATGTT CCAGAACAAG ATTTAGAAGT GGACTTAAAC
1260   AGTATCCCAG GATACGTTAA GAGTGGCTTT GTAATCAAAA ATGTTCGCGA AGTTGTAGAC
1270   AGAACATAA
```

FIG. 7A

*Jeotgalicoccus sp.* ATCC8456 orf880 (SEQ ID NO:2)

```
 60   MATLKRDKGL DNTLKVLKQG YLYTTNQRNR LNTSVFQTKA LGGKPFVVVT GKEGAEMFYN
120   NDVVQREGML PKRIVNTLFG KGAIHTVDGK KHVDRKALFM SLMTEGNLNY VRELTRTLWH
180   ANTQRMESMD EVNIYRESIV LLTKVGTRWA GVQAPPEDIE RIATDMDIMI DSFRALGGAF
240   KGYKASKEAR RRVEDWLEEQ IIETRKGNIH PPEGTALYEF AHWEDYLGNP MDSRTCAIDL
300   MNTFRPLIAI NRFVSFGLHA MNENPITREK IKSEPDYAYK FAQEVRRYYP FVPFLPGKAK
360   VDIDFQGVTI PAGVGLALDV YGTTHDESLW DDPNEFRPER FETWDGSPFD LIPQGGGDYW
420   TNHRCAGEWI TVIIMEETMK YFAEKITYDV PEQDLEVDLN SIPGYVKSGF VIKNVREVVD
430   RT
```

FIG. 7B

*Jeotgalicoccus* sp. ATCC8456 16s rRNA (partial sequence) (SEQ ID NO:3)

```
  60  GGTTACCTTG TTACGACTTC ACCCCAATTA TCAATCCCAC CTTTGACGGC TACCTCCATT
 120  AAGGTTAGTC CACCGGCTTC AGGTGTTAYC GACTTTCGTG GTGTGACGGG CGGTGTGTAC
 180  AAGACCCGGG AACGTATTCA CCGTAGCATG CTGATCTACG ATTACTAGCG ATTCCAGCTT
 240  CATGGAGTCG AGTTGCAGAC TCCAATCCGA ACTGAGAACA GTTTTATGGG ATTCGCTTGG
 300  CCTCGCGGCT TCGCTGCCCT TTGTAACCTG CCCATTGTAG CACGTGTGTA GCCCAAATCA
 360  TAAGGGGCAT GATGATTTGA CGTCATCCCC ACCTTCCTCC GGTTTGTCAC CGGCAGTCAA
 420  TCTAGAGTGC CCAACTGAAT GATGGCAACT AAATTTAAGG GTTGCGCTCG TTGCGGGACT
 480  TAACCCAACA TCTCACGACA CGAGCTGACG ACAACCATGC ACCACCTGTC TCTCTGCCCA
 540  AAAGGGAAAC CATATCTCTR TGGCGATCAG AGGATGTCAA GATTTGGTAA GGTTCTTCGC
 600  GTTGCTTCGA ATTAAACCAC ATGCTCCACC GCTTGTGCGG GTCCCCGTCA ATTCCTTTGA
 660  GTTTCAACCT TGCGGTCGTA CTCCCCAGGC GGAGTGCTTA ATGCGTTAGC TGCAGCACTG
 720  AGGGGCGGAA ACCCCCCAAC ACTTAGCACT CATCGTTTAC GGCGTGGACT ACCAGGGTAT
 780  CTAATCCTGT TTGATCCCCA CGCTTTCGCA CCTCAGCGTC AGTTACAGAC CAGAGAGCCG
 840  CCTTCGCCCA CTGGTGTTCC TCCATATCTC TGCGCATTTC ACCGCTACAC ATGGAATTCC
 900  ACTCTCCTCT TCTGCACTCA AGTAAAACAG TTTCCAATGA CCCTCCCCGG TTGAGCCGGG
 960  GGCTTTCACA TCAGACTTAT TCTACCGCCT ACGCGCGCTT TACGCCCAAT AATTCCGGAT
1020  AACGCTTGCC ACCTACGTAT TACCGCGGCT GCTGGCACGT AGTTAGCCGT GGCTTTCTGG
1080  TTAAGTACCG TCATCTCTAG GCCAGTTACT ACCTAAAGTG TTCTTCCTTA CAACAGAGT
1140  TTTACGAGCC GAAACCCTTC TTCACTCACG CGGCGTTGCT CCGTCAGACT TGCGTYCATT
1200  GCGGAAGATT CCCTACTGCT GCCTCCGTA GGAGTCTGGG CCGTGTCTCA GTCCAGTGT
1260  GGCCGATCAC CCTCTCAGGT CGGCTATGCA TCGTTGCCTT GGTGAGCCAC TACCTCACCA
1320  ACTAGCTAAT GCACCGCAGG CCCATCCTTT AGTGACAGAT AAATCCGCCT TTCATTAAGA
1380  TTACTTGTGT AATCCAACTT ATCCGGTATT AGCTACCGTT TCCGGTAGTT ATCCAGTCT
1440  AAAGGGTAGG TTGCCCACGT GTTACTCACC CGTCCGCCGC TCGATTGTAA GGAGCAAGCT
1500  CCTTACGCTC GCGCTCGACT TGCATGTATT AGGCACGCCG CCAGCGTTCA TCCTGAGCCA
1510  GGATCAA
```

FIG. 7C

*Jeotgalicoccus sp. ATCC8456 orf880, codon-optimized DNA* (SEQ ID NO:4)

```
   1  ATGGCTACTC TGAAACGTGA CAAAGGTCTG GATAACACTC TGAAAGTTCT GAAACAAGGT
  61  TACCTGTACA CTACCAACCA GCGCAACCGT CTGAACACCA GCGTCTTTCA AACCAAAGCC
 121  CTGGGTGGCA AACCGTTCGT GGTTGTGACC GGCAAAGAAG GCGCAGAGAT GTTCTATAAC
 181  AACGATGTGG TGCAGCGTGA GGGCATGCTG CCGAAACGTA TTGTAAACAC CCTGTTCGGC
 241  AAGGGTGCGA TCCATACCGT GGATGGCAAG AAACACGTAG ACCGTAAAGC ACTGTTCATG
 301  TCTCTGATGA CTGAGGGCAA CCTGAACTAT GTACGTGAAC TGACCCGCAC CCTGTGGCAT
 361  GCGAACACGC AGCGTATGGA ATCTATGGAT GAGGTGAACA TCTACGTGA AAGCATCGTT
 421  CTGCTGACGA AGGTGGGCAC CCGCTGGGCA GGTGTTCAGG CACCGCCGGA GGACATTGAG
 481  CGCATCGCTA CCGATATGGA TATTATGATC GATAGCTTCC GTGCTCTGGG TGGCGCATTT
 601  ATCATCGAAA CCCGTAAAGG TAACATCCAC CCACCGGAAG GTACGGCTCT GTACGAATTT
 661  GCACACTGGG AGGATTATCT GGGTAATCCA ATGGACTCTC GTACCTGCGC GATCGATCTG
 721  ATGAACACGT TCGCCCGCT GATCGCTATC AACCGCTTTG TTTCTTTCGG TCTGCACGCG
 781  ATGAACGAAA ACCCGATCAC TCGTGAGAAG ATTAAGTCCG AGCCGGATTA CGCATACAAA
 841  TTCGCACAGG AGGTCCGTCG CTACTACCCG TTCGTTCCTT TCCTGCCGGG TAAAGCAAAG
 901  GTAGACATCG ACTTCCAGGG TGTAACCATC CCAGCCGGTG TGGGCCTGGC ACTGGATGTT
 961  TACGGTACCA CCCATGATGA AAGCCTGTGG GATGATCCGA ACGAATTTCG CCCGGAGCGT
1021  TTCGAGACTT GGGATGGTTC TCCATTTGAC CTGATTCCGC AAGGTGGTGG TGATTACTGG
1081  ACCAATCACC GCTGTGCCGG CGAGTGGATC ACCGTCATTA TCATGGAAGA AACGATGAAA
1141  TACTTCGCCG AGAAAATCAC TTATGACGTT CCAGAACAGG ACCTGGAAGT AGATCTGAAC
1201  TCCATCCCGG GCTATGTCAA AAGCGGCTTT GTTATCAAAA ACGTCCGTGA AGTAGTCGAT
1261  CGCACCTAA
```

FIG. 7D

*Jeotgalicoccus sp. ATCC8456 orf880, Protein* (SEQ ID NO:5)

```
  1  MATLKRDKGL DNTLKVLKQG YLYTTNQRNR LNTSVFQTKA LGGKPFVVVT GKEGAEMFYN
 61  NDVVQREGML PKRIVNTLFG KGAIHTVDGK KHVDRKALFM SLMTEGNLNY VRELTRTLWH
121  ANTQRMESMD EVNIYRESIV LLTKVGTRWA GVQAPPEDIE RIATDMDIMI DSFRALGGAF
181  KGYKASKEAR RRVEDWLEEQ IIETRKGNIH PPEGTALYEF AHWEDYLGNP MDSRTCAIDL
241  MNTFRPLIAI NRFVSFGLHA MNENPITREK IKSEPDYAYK FAQEVRRYYP FVPFLPGKAK
301  VDIDFQGVTI PAGVGLALDV YGTTHDESLW DDPNEFRPER FETWDSPFD LIPQGGGDYW
361  TNHRCAGEWI TVIIMEETMK YFAEKITYDV PEQDLEVDLN SIPGYVKSGF VIKNVREVVD
421  RT
```

FIG. 7E

*Corynebacterium efficiens orf_CE2459 (NP_739069) DNA (SEQ ID NO:6)*

```
   1 TCAGCGTTCC ACGCGCACCC GCATGCCGGT TTCGGAGCGG GTGAGCATCT GTGTCCAGGG
  61 GAAACGGGTA TCAGCCGGAT CCGTGGAGAG CACCACACCG GCCGGCATA AAGCCTCCAC
 121 CATGGCTGTG AGCGCGGCCA TGGCGATCTT CTCGCCCGGG CAGCGGTGAC CGGTGTACAC
 181 CCCGGCTCCG CCCTGGGGCA CGAAGCTGGT GAGCCTCTCA TAGTCCTCCT GGGTGCCAG
 241 GTCCTCCCGG GACAGGAAAC GCTCCGGTTG AAACGCACTC GGGTTCTCCC ACTCATTGGG
 301 GTCGGTGTTG GTGCCGTAGA TGTCGATGAT CACGCGTTCA CCCTCATGCA CGGGGCAGCC
 361 CTGGATTTCG GTGTCGGTGG TGGCGATGGC CGGCAGCATG GCACAAACG GATAGACGCG
 421 GCGGACCTCC TGGGCGAAGG CGAAGGCCAC GGGCTGTCCT CCCTCGCGGA TCTTCTCCAC
 481 CCACTCGGGG TGCTCGACCA GGGCGCTGCC GGCGAAGGAG GCGAACAGTG ATACTGCCAC
 541 GGTGGGACGG GTGAGGTTCT GTAATTCGAT GCCGGCGATG GAGGCGTCGA CAAGCTCCCC
 601 GTCCGGACCG ACCAACCGGG ACATGGCCTC CAGGGCGCTA CCCGGCGCCA CGTGCCGCTC
 661 CCCGGCGCGC GCCTGCCTGA TGAGCTTCAA GGCCCACCTG TTCAACCGCG CCCGGTTGAT
 721 CCAGCCCAGG GCGTGCCCTT TGAGGGGATG GCCGAACTGA TAGACCAGCT CGGCCATCTG
 781 ATGGGCGCGC CGGCTGGCTT CCTTCTGGCT AAGCTCAATG CCCGCCCAAC GGTAGGCCGC
 841 ACGCCCGAAG GCCAGCGCCG CACCGTCATA GACCGTCCCG GGTTCGCGGG CCCAGTCCTG
 901 CACCACACGG TCCACCTCAC GGCGGACGAG TGCATCGAAC TCGGCGACCT TGTCATCGTC
 961 ATAGGCGACA TCGGCGAGCT GACGTTTGCG CAGACGGTGC TCCTCGCCGT CCAGCGAATG
1021 CACCGCACCC TCACCGAACA GGGGATGCCG ATCACCGCG GCATGGCTC CGTCACGTTT
1081 CATCCGGTCA TTGTCATAGA ACAGCTCCAC TCCGGCTGAA CCGCGCACGA TGGTGACGGG
1141 TTTGAACAGC ATGCGCGACC GCAGCGGGT GTTGGCATCG GTGAGATAC CGGCCTTGCG
1201 GCGCAGACGG GAGAGAAAAA GGTAGCCGTG GCGCAGCAGG TTGGGGCCT GTTCGCCGGG
1261 GGCAAAGGGG CAGGAGGATG TCTGAGTCAT CGGTGGACC TCTTCCAA
```

FIG. 7F

*Corynebacterium efficiens orf_CE2459 (NP_739069) Protein (SEQ ID NO:7)*

```
  1 MEEVPPMTQT SSCPFAPGEQ APNLLRHGYL FLSRLRRKAG ISPDANTPLR SRMLFKPVTI
 61 VRGSAGVELF YDNDRMKRDG AMPAVIRIPL FGEGAVHSLD GEEHRLRKRQ LADVAYDDDK
121 VAEFDALVRR EVDRVVQDWA REPGTVYDGA ALAFGRAAYR WAGIELSQKE ASRRAHQMAE
181 LVYQFGHPLK GHALGWINRA RLNRWALKLI RQARAGERHV APGSALEAMS RLVGPDGELV
241 DASIAGIELQ NLTRPTVAVS LFASFAGSAL VEHPEWVEKI REGGQPVAFA FAQEVRRVYP
301 FVPMLPAIAT TDTEIQGCPV HEGERVIIDI YGTNTDPNEW ENPSAFQPER FLSREDLGTQ
361 EDYERLTSFV PQGGAGVYTG HRCPGEKIAM AALTAMVEAL CRPGVVLSTD PADTRFPWTQ
421 MLTRSETGMR VRVER
```

FIG. 7G

*Kokuria rhizophila orf_KRH21570 (YP_001856010)DNA* (SEQ ID NO:8)

```
   1 ATGACTTCAC CGTTCGGTCA GACCCGTTCC GAGCAGGGCC CGTCCCTACT CCGCTCCGGC
  61 TACCTCTTTG CCTCCCGCGC ACGACGCCGC GCGGGCCTCT CCTCCGACTC GGGGTGCCCC
 121 GTCCGCATGC CTCTGCTGGG CAAGCAGACC GTCCTGGTCC GCGGCGAGGA GGGCGTCAAG
 181 CTCTTCTACG ACACCTCCCG CGTGCGGCGC GACGGCGCCA TGCCCGGAGT CGTGCAGGGG
 241 CCGCTCTTCG GTGCGGGCGC CGTGCACGGG CTGGACGGCG AGGCCCACCG GGTGCGCAAG
 301 AACCAACTCG CGGACATGGC CTACGAGGAC GAGCGCGTGG CGGCCTACAA GCCCTTCGTG
 361 GCGGAGGAGC TCGAGAACCT CGTCGCGCGG TGAAGGACG GCGATAACGT CTACGACAGC
 421 ACCGCCATCG CCTTCGGCCG CGCGTCCTTC CGGTGGGCCG GTCTGCAGTG GGGCGTGCCG
 481 GAGATGGACC GCTGGGCCCG CCGCATGAGC CGCCTGCTGG ACACCTTCGG GCGCCCCGCC
 541 ACGCACCTGG TGTCCCGGCT GGACCGGATC GCCCTGGACC GCCGCTTCGC CGCGCTCATC
 601 AAGGACGTGC GCGCGGGCAA GGTCAACGCA CCCGAGGACT CCGTGCTCGC GCACATGGCC
 661 GCCCTGGTGG ACGAGCACGG CGAGCTGGTG GACGCGAAGA CCGCGGGCAT CGAGCTGCAG
 721 AACCTCACCC GCCCGAACGT GGCCGTGGCC CGCTTCGCCG CGTTCGCGGC CACCGCCCTG
 781 GTGGAGCACC CTGAGTGGGT CGAGCGCATC CGCGCCGCCT CCGAGCAGCG CGGCGGCACC
 841 CTGCTGGACG TCCCGAGGC CGTGGCCTTC GCGCAGGAGG TCCGCCGCGT CTACCCGTTC
 901 GTGCCCATGC TCCCCGCGGA GGTCACACAG GACACCGAGA TCCAGGGCTG CCCCGTGCAC
 961 AAGGGGAGC GCGTGGTCCT GGACATCCTG GGCACCAACA CGGATCCGAC GTCCTGGAC
1021 CGCGCGGCCA CGTTCGACCC CGAGCGCTTC CTGGGGGTCG AGGACGCCGA GGCGATCACC
1081 ACGTTCATCC CCAGGGCGG CGCTGAGGTC CGCACGGGCC ACCGCTGCCC CGGCGAGAAG
1141 ATCGCGGTCA CGTCCCTCTC CGCCGCCGTG GTGGCGCTGT GCCGGCCGGA GGTCCAGCTG
1201 CCGGGCGACC AGGACGACCT CACGTTCTCG TGGACCCACA TGCTGACCCG CCCGGTCACC
1261 GGGGTGCGGG TCCGCACCAC CCGCTGA
```

FIG. 7H

*Kokuria rhizophila orf_KRH21570 (YP_001856010) codon-optimized DNA (SEQ ID NO:9)*

```
   1 ATGACGAGCC CGTTCGGCCA GACCCGTAGC GAACAGGGCC CGAGCCTGCT GCGTTCGGGT
  61 TACTTGTTTG CAAGCCGCGC TCGCCGCCGT GCTGGCCTGA GCAGCGATAG CGGTTGTCCA
 121 GTTCGCATGC CGCTGCTGGG TAAGCAAACG GTTCTGGTGC GCGGCGAGGA AGGCGTCAAA
 181 CTGTTCTATG ATACCAGCCG TGTTCGTCGT GACGGCGCGA TGCCAGGCGT CGTGCAGGGC
 241 CCTCTGTTCG GTGCAGGTGC GGTTCACGGT CTGGACGGCG AAGCGCACCG CGTTCGCAAG
 301 AACCAACTGG CGGATATGGC TTATGAAGAT GAACGTGTGG CTGCGTACAA GCCGTTCGTT
 361 GCGGAAGAGT TGGAGAATCT GGTTGCACGT GGAAAGATG GTGACAACGT CTACGACAGC
 421 ACGGCAATTG CATTTGGCCG CGCATCTTTT CGTTGGGCCG GTCTGCAGTG GGGTGTGCCG
 481 GAGATGGATC GCTGGGCACG CCGCATGAGC CGTCTGTTGG ATACCTTCGG TCGTCCGGCC
 541 ACGCACCTGG TGAGCCGTTT GGACCGTATT GCTTTGGATC GCCGCTTTGC AGCATTGATT
 601 AAGGACGTGC GTGCCGGTAA AGTGAACGCT CCGGAAGACA GCGTCCTGGC CCACATGGCA
 661 GCTCTGGTCG ACGAGCATGG TGAATTGGTG GATGCTAAGA CGGCGGGTAT CGAACTGCAG
 721 AATTTGACCC GTCCGAATGT GGCGGTGGCT CGTTTTGCGG CCTTTGCGGC GACGGCACTG
 781 GTTGAGCATC CGGAGTGGGT CGAACGTATT CGTGCAGCCT CCGAACAGCG TGGCGGTACC
 841 TTGCTGGACG TTCCGGAGGC CGTGGCGTTC GCGCAGGAAG TTCGTCGCGT CTACCCGTTT
 901 GTCCCGATGC TGCCAGCTGA AGTTACCCAG GACACCGAGA TCCAGGGTTG TCCGGTTCAC
 961 AAGGGTGAGC GCGTGGTTCT GGATATTTTG GGTACCAATA CCGATCCGAC CAGCTGGGAC
1021 CGTGCGGCGA CCTTTGACCC GGAGCGCTTT CTGGGTGTTG AGGACGCGGA AGCCATCACC
1081 ACCTTTATCC CGCAGGGCGG TGCAGAGGTG CGTACGGGCC ATCGCTGTCC GGGTGAGAAG
1141 ATCGCCGTCA CCAGCCTGAG CGCTGCTGTC GTTGCGCTGT GTCGCCCGGA GGTGCAACTG
1201 CCGGGTGATC AGGATGATCT GACTTTTAGC TGGACCCACA TGCTGACGCG CCCTGTCACG
1261 GGTGTTCGCG TCCGCACCAC GCGCTAA
```

FIG. 7I

*Kokuria rhizophila orf_KRH21570 (YP_001856010) Protein (SEQ ID NO:10)*

```
  1 MTSPFGQTRS EQGPSLLRSG YLFASRARRR AGLSSDSGCP VRMPLLGKQT VLVRGEEGVK
 61 LFYDTSRVRR DGAMPGVVQG PLFGAGAVHG LDGEAHRVRK NQLADMAYED ERVAAYKPFV
121 AEELENLVAR WKDGDNVYDS TAIAFGRASF RWAGLQWGVP EMDRWARRMS RLLDTFGRPA
181 THLVSRLDRI ALDRRFAALI KDVRAGKVNA PEDSVLAHMA ALVDEHGELV DAKTAGIELQ
241 NLTRPNVAVA RFAAFAATAL VEHPEWVERI RAASEQRGGT LLDVPEAVAF AQEVRRVYPF
301 VPMLPAEVTQ DTEIQGCPVH KGERVVLDIL GTNTDPTSWD RAATFDPERF LGVEDAEAIT
361 TFIPQGGAEV RTGHRCPGEK IAVTSLSAAV VALCRPEVQL PGDQDDLTFS WTHMLTRPVT
421 GVRVRTTR
```

FIG. 7J

*Methylobacterium populi orf_Mpop1292 (YP_001923998) codon-optimized DNA* (SEQ ID NO:11)

```
   1 ATGCCGGCTG CCATTGCCAC CCACCGTTTC CGCAAAGCAC GCACCCTGCC GCGTGAGCCA
  61 GCTCCAGATA GCACGCTGGC GCTGCTGCGC GAGGGTTACG GTTTCATCCG TAACCGTTGT
 121 CGCCGTCACG ACAGCGACCT GTTCGCAGCC CGTTTGTTGC TGAGCCCGGT CATCTGCATG
 181 TCTGGCGCGG AGGCGGCACG CCACTTTTAC GACGGTCACC GCTTTACTCG TCGTCATGCA
 241 CTGCCGCCGA CCAGCTTCGC TCTGATCCAA GACCACGGTA GCGTTATGGT TCTGGATGGC
 301 GCCGCACACC TGGCACGTAA GGCTATGTTC CTGAGCCTGG TCGGTGAAGA GGCCCTGCAA
 361 CGTTTGGCGG GCCTGGCGGA ACGTCACTGG CGCGAAGCGG TGTCCGGCTG GGCACGTAAA
 421 GATACGGTGG TTCTGCTGGA CGAGGCACAT CGCGTGCTGA CCGCAGCGGT CTGCGAATGG
 481 GTGGGTTTGC CGCTGGGCCC GACCGAAGTG GATGCTCGCG CGCGTGAGTT CGCAGCGATG
 541 ATTGATGGCA CGGGTGCAGT GGGTCCGCGC AACTGGCGCG GTCACTTGTA TCGTGCACGC
 601 ACGGAGCGTT GGGTTCGCAA GGTTATCGAC GAGATCCGCT CCGGTCGTCG CGATGTCCCT
 661 CCGGGTGCCG CACGCACTAT CGCGGAGCAT CAAGATGCCG ACGGTCAACG TCTGGATCGT
 721 ACGGTCGCGG GTGTTGAACT GATCAACGTT CTGCGCCCGA CCGTTGCGAA CGCACGTTAC
 781 ATTGTCTTTG CAGCTATGGC GCTGCACGAT CACCCTCATC AGCGCGCTGC GTTGGCGGAC
 841 GGTGGTGAAG CTGCGGAACG CTTTACCGAT GAAGTGCGTC GCTTCTACCC ATTCATCCCG
 901 TTTATCGGCG GTCGTGTCCG TGCGCCGTTC CATTTTGGTG GCCACGACTT TCGCGAAGGT
 961 GAATGGGTGC TGATGGATCT GTATGGTACC AATCGTGACC CACGTCTGTG GCACGAGCCA
1021 GAACGTTTCG ACCCGGATCG TTTTGCTCGT GAAACCATCG ATCCGTTTAA TATGGTTTCT
1081 CATGGTGCGG GTAGCGCTCG CGATGGTCAC CGCTGTCCGG GTGAGGGTAT TACCCGCATC
1141 CTGTTGCGTA CGCTGAGCCG CCAACTGGCC GCGACGCGCT ACACGGTTCC GCCACAAGAC
1201 CTGACCCTGG ACCTGGCGCA TGTGCCTGCC CGTCCGCGCA GCGGTTTTGT TATGCGTGCT
1261 GTGCACGCGC CGTAA
```

FIG. 7K

*Methylobacterium populi orf_Mpop1292 (YP_001923998) Protein* (SEQ ID NO:12)

```
  1 MPAAIATHRF RKARTLPREP APDSTLALLR EGYGFIRNRC RRHDSDLFAA RLLLSPVICM
 61 SGAEAARHFY DGHRFTRRHA LPPTSFALIQ DHGSVMVLDG AAHLARKAMF LSLVGEEALQ
121 RLAGLAERHW REAVSGWARK DTVVLLDEAH RVLTAAVCEW VGLPLGPTEV DAREFAAM
181 IDGTGAVGPR NWRGHLYRAR TERWVRKVID EIRSGRRDVP PGAARTIAEH QDADGQRLDR
241 TVAGVELINV LRPTVANARY IVFAAMALHD HPHQRAALAD GGEAAERFTD EVRRFYPFIP
301 FIGGRVRAPF HFGGHDFREG EWVLMDLYGT NRDPRLWHEP ERFDPDRFAR ETIDPFNMVS
361 HGAGSARDGH RCPGEGITRI LLRTLSRQLA ATRYTVPPQD LTLDLAHVPA RPRSGFVMRA
421 VHAP
```

FIG. 7L

*Bacillus subtilis CYP152A1 (NP_388092) DNA* (SEQ ID NO:13)

```
   1 ATGAATGAGC AGATTCCACA TGACAAAAGT CTCGATAACA GTCTGACACT GCTGAAGGAA
  61 GGGTATTTAT TTATTAAAAA CAGAACAGAG CGCTACAATT CAGATCTGTT TCAGGCCCGT
 121 TTGTTGGGAA AAAACTTTAT TTGCATGACT GGCGCTGAGG CGGCGAAGGT GTTTTATGAT
 181 ACGGATCGAT TCCAGCGGCA GAACGCTTTG CCTAAGCGGG TGCAGAAATC GCTGTTTGGT
 241 GTTAATGCGA TTCAGGGAAT GGATGGCAGC GCGCATATCC ATCGGAAGAT GCTTTTTCTG
 301 TCATTGATGA CACCGCCGCA TCAAAAACGT TTGGCTGAGT TGATGACAGA GGAGTGGAAA
 361 GCAGCAGTCA CAAGATGGGA GAAGGCAGAT GAGGTTGTGT TATTTGAAGA AGCAAAAGAA
 421 ATCCTGTGCC GGGTAGCGTG CTATTGGGCA GGTGTTCCGT TGAAGGAAAC GGAAGTCAAA
 481 GAGAGAGCGG ATGACTTCAT TGACATGGTC GACGCGTTCG GTGCTGTGGG ACCGCGGCAT
 541 TGGAAAGGAA GAAGAGCAAG GCCGCGTGCG GAAGAGTGGA TTGAAGTCAT GATTGAAGAT
 601 GCTCGTGCCG GCTTGCTGAA AACGACTTCC GGAACAGCGC TGCATGAAAT GGCTTTTCAC
 661 ACACAAGAAG ATGGAAGCCA GCTGGATTCC CGCATGGCAG CCATTGAGCT GATTAATGTA
 721 CTGCGGCCTA TTGTCGCCAT TTCTTACTTT CTGGTGTTTT CAGCTTTGGC GCTTCATGAG
 781 CATCCGAAGT ATAAGGAATG GCTGCGGTCT GGAAACAGCC GGGAAGAGA AATGTTTGTG
 841 CAGGAGGTCC GCAGATATTA TCCGTTCGGC CGTTTTTAG GGGCGCTTGT CAAAAAAGAT
 901 TTTGTATGGA ATAACTGTGA GTTTAAGAAG GGCACATCGG TGCTGCTTGA TTTATATGGA
 961 ACGAACCACG ACCCTCGTCT ATGGGATCAT CCCGATGAAT TCCGGCCGGA ACGATTTGCG
1021 GAGCGGGAAG AAAATCTGTT TGATATGATT CCTCAAGGCG GGGGCACGC CGAGAAAGGC
1081 CACCGCTGTC CAGGGGAAGG CATTACAATT GAAGTCATGA AAGCGAGCCT GGATTTCCTC
1141 GTCCATCAGA TTGAATACGA TGTTCCGGAA CAATCACTGC ATTACAGTCT CGCCAGAATG
1201 CCATCATTGC CTGAAAGCGG CTTCGTAATG AGCGGAATCA GACGAAAAAG TTAA
```

FIG. 7M

*Bacillus subtilis CYP152A1 (NP_388092) Protein* (SEQ ID NO:14)

```
  1 MNEQIPHDKS LDNSLTLLKE GYLFIKNRTE RYNSDLFQAR LLGKNFICMT GAEAAKVFYD
 61 TDRFQRQNAL PKRVQKSLFG VNAIQGMDGS AHIHRKMLFL SLMTPPHQKR LAELMTEEWK
121 AAVTRWEKAD EVVLFEEAKE ILCRVACYWA GVPLKETEVK ERADDFIDMV DAFGAVGPRH
181 WKGRRARPRA EEWIEVMIED ARAGLLKTTS GTALHEMAFH TQEDGSQLDS RMAAIELINV
241 LRPIVAISYF LVFSALALHE HPKYKEWLRS GNSREREMFV QEVRRYYPFG PFLGALVKKD
301 FVWNNCEFKK GTSVLLDLYG TNHDPRLWDH PDEFRPERFA EREENLFDMI PQGGGHAEKG
361 HRCPGEGITI EVMKASLDFL VHQIEYDVPE QSLHYSLARM PSLPESGFVM SGIRRKS
```

Accession Numbers are from NCBI, GenBank, Release 159.0 as of April 15 2007
EC Numbers are from KEGG, Release 42.0 as of April 2007 (plus daily updates up to March, 2008)

| CATEGORY | GENE | NAME | ACCESSION | EC NUMBER | MODIFICATION | USE | ORGANISM |
|---|---|---|---|---|---|---|---|
| 1. Fatty Acid Production Increase / Product Production Increase | | | | | | | |
| increase acyl-CoA | | | | | | | |
| reduce catabolism of derivatives and intermediates | | | | | | | |
| reduce feedback inhibition | | | | | | | |
| attenuate other pathways that consume fatty acids | | | | | | | |
| | accA | Acetyl-CoA carboxylase, subunit A (carboxyltransferase alpha) | AAC73296, NP_414727 | 6.4.1.2 | Over-express | increase Malonyl-CoA production | Escherichia coli, Lactococci |
| | accB | Acetyl-CoA carboxylase, subunit B (BCCP: biotin carboxyl carrier protein) | NP_417721 | 6.4.1.2 | Over-express | increase Malonyl-CoA production | Escherichia coli, Lactococci |
| | accC | Acetyl-CoA carboxylase, subunit C (biotin carboxylase) | NP_417722 | 6.4.1.2, 6.3.4.14 | Over-express | increase Malonyl-CoA production | Escherichia coli, Lactococci |
| | accD | Acetyl-CoA carboxylase, subunit D (carboxyltransferase beta) | NP_416819 | 6.4.1.2 | Over-express | increase Malonyl-CoA production | Escherichia coli, Lactococci |

FIG. 10B

| | | | | | |
|---|---|---|---|---|---|
| aceE | pyruvate dehydrogenase, subunit E1 | NP_414656, AAC73226 | 1.2.4.1 | Over-express | increase Acetyl-CoA production | Escherichia coli |
| aceF | pyruvate dehydrogenase, subunit E2 | NP_414657 | 2.3.1.12 | Over-express | increase Acetyl-CoA production | Escherichia coli |
| ackA | acetate kinase | AAC75356, NP_416799 | 2.7.2.1 | Delete or reduce | increase Acetyl-CoA production | Escherichia coli |
| ackB | acetate kinase AckB | BAB81430 | 2.7.2.1 | Delete or reduce | increase Acetyl-CoA production | Escherichia coli |
| acpP | acyl carrier protein | AAC74178 | NONE | Over-express | increase Acetyl-CoA production | Escherichia coli |
| fadD | acyl-CoA synthase | AP_002424 | 2.3.1.86, 6.2.1.3 | Over-express | increase Fatty acid production | Escherichia coli W3110 |
| adhE | alcohol dehydrogenase | CAA47743 | 1.1.1.1, 1.2.1.10 | Delete or reduce | increase Acetyl-CoA production | Escherichia coli W3111 |
| cer1 | Aldehyde decarbonylase | BAA11024 | 4.1.99.5 | Over-express | increase Acetyl-CoA production | Arabidopsis thaliana |
| fabA | beta-hydroxydecanoyl thioester dehydrase | NP_415474 | 4.2.1.60 | express | fatty acyl-CoA production | E. coli K12 |
| fabD | [acyl-carrier-protein] S-malonyltransferase | AAC74176 | 2.3.1.39 | Over-express | increase Acetyl-CoA production | E. coli K12 |
| fabF | 3-oxoacyl-[acyl-carrier protein] synthase II | AAC74179 | 2.3.1.179 | Delete or OverExpress | increase Acetyl-CoA production | E. coli K12 |
| fabG | 3-oxoacyl-[acyl-carrier protein] reductase | AAC74177 | 1.1.1.100 | Over-express | increase Acetyl-CoA production | E. coli K12 |

FIG. 10C

| | | | | | |
|---|---|---|---|---|---|
| | fabH | 3-oxoacyl-[acyl-carrier-protein] synthase III | AAC74175 | 2.3.1.180 | Over-express | increase Acetyl-CoA production | E. coli K12, lactococci |
| | fabI | enoyl-[acyl-carrier-protein] reductase, NADH-dependent | NP_415804 | 1.3.1.9 | express | fatty acyl-CoA production | E. coli K12, lactococci |
| | fabR | Transcriptional Repressor | NP_418398 | NONE | Delete or reduce | modulate unsaturated fatty acid production | E. coli K12 |
| | fabZ | (3R)-hydroxymyristol acyl carrier protein dehydratase | NP_414722 | 4.2.1.- | | | E. coli K12 |
| | fadE | acyl-CoA dehydrogenase | AAC73325 | 1.3.99.3, 1.3.99.- | Delete or reduce | increase Acetyl-CoA production | E. coli K12 |
| | GST, gshB | Glutathione synthase | P04425 | 6.3.2.3 | Delete or reduce | increase Acyl-CoA | E. coli K12 |
| | gpsA | biosynthetic sn-glycerol 3-phosphate dehydrogenase | AAC76632, NP_418065 | EC: 1.1.1.94 | Delete or reduce | increase Acetyl-CoA production | E. coli K12 |
| | ldhA | lactate dehydrogenase | AAC74462, NP_415898 | EC: 1.1.1.27, 1.1.1.28 | Delete or reduce | increase Acetyl-CoA production | E. coli K12 |
| | Lipase | Triglyceride Lipase | CAA89087, CAA98876 | 3.1.1.3 | express | increase Fatty acid production | Saccharomyces cerevisiae |
| | | Malonyl-CoA decarboxylase | AAA26500 | 4.1.1.9, 4.1.1.41 | Over-express | | Saccharopolyspora erythraea |
| | panD | aspartate 1-decarboxylase | BAB96708 | 4.1.1.11 | Over-express | increase Acyl-CoA | Escherichia coli W3110 |

FIG. 10D

| | | | | | |
|---|---|---|---|---|---|
| panK a.k.a. coaA | pantothenate kinase | AAC76952 | 2.7.1.33 | Over-express | increase Acetyl-CoA production | E.coli |
| panK a.k.a. coaA, R106K | pantothenate kinase | AAC76952 | 2.7.1.33 | Express, Over-express, R106K mutation | increase Acetyl-CoA production | E. coli |
| pdh | Pyruvate dehydrogenase | BAB3480, AAC7322b, NP_415392 | 1.2.4.1 | Over-express | increase Acetyl-CoA production | |
| pflB | formate acetyltransferase (pyruvate formate lyase) | AAC73989, P09373 | EC: 2.3.1.54 | Delete or reduce | increase Acetyl-CoA production | |
| plsB | acyltransferase | AAC77011 | 2.3.1.15 | D311E mutation | reduce limits on Acyl-CoA pool | E. coli K12 |
| poxB | pyruvate oxidase | AAC73958, NP_415392 | 1.2.2.2 | Delete or reduce | increase Acetyl-CoA production | |
| pta | phosphotransacetylase | AAC75357, NP_416800 | 2.3.1.8 | Delete or reduce | increase Acetyl-CoA production | |
| udhA | pyridine nucleotide transhydrogenase | CAA46822 | 1.6.1.1 | Over-express | conversion NADH to NADPH or vice versa | |
| | fused 3-hydroxybutyryl-CoA epimerase/ delta(3)-cis-delta(2)-trans-enoyl-CoA isomerase/ enoyl-CoA hydratase and 3-hydroxyacyl-CoA dehydrogenase | | 4.2.1.17, 5.1.2.3, 5.3.3.8, 1.1.1.35 | | | |
| fadB | | AP_003956 | | Delete or reduce | Block fatty acid degradation | E. coli |

FIG. 10E

| | | | | | |
|---|---|---|---|---|---|
| | fadJ | 3-hydroxyacyl-CoA dehydrogenase; k01692 enoyl-CoA hydratase; k01782 3-hydroxybutyryl-CoA epimerase | AAC75401 | 1.1.1.35, 4.2.1.17, 5.1.2.3 | Delete or reduce | Block fatty acid degradation | E. coli |
| | fadA | 3-ketoacyl-CoA thiolase | BAE77458 | 2.3.1.16 | Delete or reduce | Block fatty acid degradation | E. coli |
| | fadI | beta-ketoacyl-CoA thiolase | AAC75402 | 2.3.1.16 | Delete or reduce | Block fatty acid degradation | E. coli |
| | YdiO | acyl-coA dehydrogenase | YP_852786 | 1.3.99.- | Delete or reduce | Block fatty acid degradation | E. coli |
| 2. Structure Control | | | | | | | |
| 2A. Chain Length Control | | | | | | | |
| 2 | tesA | thioesterase | P0ADA1 | 3.1.2.-, 3.1.1.5 | Delete and/or express | C18 Chain Length | |
| | tesA without leader sequence | thioesterase | AAC73596, NP_415027 | 3.1.2.-, 3.1.1.5 | express or overexpress | C18:1 | E.coli |
| | tesA without leader sequence:L109P | thioesterase | P0ADA1 | 3.1.2.-, 3.1.1.5 | Express and/or overexpress mutation L109P | <C18 Chain Length | E. coli |
| | fatB1 (umbellularia) | thioesterase | Q41635 | 3.1.2.14 | express or overexpress | C12:0 | Umbellularia californica |
| | fatB2 (umbellularia)DE LETE umbellularia | thioesterase | AAC49269 | 3.1.2.14 | express or overexpress | C8:0 - C10:0 | Cuphea hookeriana |
| | fatB3 | thioesterase | AAC72881 | 3.1.2.14 | express or overexpress | C14:0 - C16:0 | Cuphea hookeriana |

FIG. 10F

| | | | | | | | |
|---|---|---|---|---|---|---|---|
| | fatB (cinnamonum) | thioesterase | Q39473 | 3.1.2.14 | express or overexpress | C14:0 | Cinnamomum camphora |
| | fatB[M141T]* | thioesterase | CAA85388 | 3.1.2.14 | express or overexpress | C16:1 | Arabidopsis thaliana |
| | fatA1 (Helianthus) | thioesterase | AAL79361 | 3.1.2.14 | express or overexpress | C18:1 | Helianthus annuus |
| | atfata (ARABIDOPSIS FATA ACYL-ACP THIOESTERASE) | thioesterase | NP_189147, NP_193041 | 3.1.2.14 | express or overexpress | | Arabidopsis thaliana |
| | fatA | thioesterase | CAC39106 | 3.1.2.14 | express or overexpress | C18:1 | Arabidopsis thaliana |
| | fatA (cuphea) | thioesterase | AAC72883 | 3.1.2.14 | express or overexpress | C18:1 | Brassica juncea |
| | | | | | | C18:1 | Cuphea hookeriana |
| 2B. Branching Control | | | | | | | |
| | attenuate FabH express FabH from S. glaucescens or S. coelicolor and knock out endogenous FabH | | | | | increase branched chain fatty acid derivatives | |
| | express FabH from B. subtilis and knock out endogenous FabH | | | | | | |

FIG. 10G

| | | | | | | |
|---|---|---|---|---|---|---|
| bdk - E3 - dihydrolipoyl dehydrogenase subunit | | | | | | |
| bkd - E1 - alpha/beta subunit | decarboxylase subunits of branched-chain α-ketoacid dehydrogenase complex | | EC 1.2.4.4 | | | |
| bkd - E2 - dihydrolipoyl transacylase subunit | | | EC 1.2.4.4 | | | |
| | | | EC 1.2.4.4 | | | |
| bkdA1 | branched-chain α-ketoacid dehydrogenase α-subunit (E1a) | NP_628806 | EC 1.2.4.4 | express or Over-Express | make branched-chain acyl-CoA precursors | Streptomyces coelicolor |
| bkdB1 | branched-chain α-ketoacid dehydrogenase α-subunit (E1b) | NP_628805 | EC 1.2.4.4 | express or Over-Express | make branched-chain acyl-CoA precursors | Streptomyces coelicolor |
| bkdC1 | dihydrolipoyl transacetylase (E2) | NP_628804 | EC 2.3.1.168 | express or Over-Express | make branched-chain acyl-CoA precursors | Streptomyces coelicolor |
| bkdA2 | branched-chain α-ketoacid dehydrogenase α-subunit | NP_733618 | EC 1.2.4.4 | express or Over-Express | make branched-chain acyl-CoA precursors | Streptomyces coelicolor |

FIG. 10H

| | | | | | |
|---|---|---|---|---|---|
| bkdB2 | branched-chain a-ketoacid dehydrogenase b-subunit (E1b) | NP_628019 | EC 1.2.4.4 | express or Over-Express | make branched-chain acyl-CoA precursors | Streptomyces coelicolor |
| bkdC2 | dihydrolipoyl transacetylase (E2) | NP_628018 | EC 2.3.1.168 | express or Over-Express | make branched-chain acyl-CoA precursors | Streptomyces coelicolor |
| bkdA | branched-chain a-ketoacid dehydrogenase a-subunit (E1a) | BAC72074 | EC 1.2.4.4 | express or Over-Express | make branched-chain acyl-CoA precursors | Streptomyces avermitilis |
| bkdB | branched-chain a-ketoacid dehydrogenase b-subunit (E1b) | BAC72075 | EC 1.2.4.4 | express or Over-Express | make branched-chain acyl-CoA precursors | Streptomyces avermitilis |
| bkdC | dihydrolipoyl transacetylase (E2) | BAC72076 | EC 2.3.1.168 | express or Over-Express | make branched-chain acyl-CoA precursors | Streptomyces avermitilis |
| bkdF | branched-chain a-ketoacid dehydrogenase a-subunit (E1a) | BAC72088 | EC 1.2.4.4 | express or Over-Express | make branched-chain acyl-CoA precursors | Streptomyces avermitilis |
| bkdG | branched-chain a-ketoacid dehydrogenase b-subunit (E1b) | BAC72089 | EC 1.2.4.4 | express or Over-Express | make branched-chain acyl-CoA precursors | Streptomyces avermitilis |
| bkdH | dihydrolipoyl transacetylase (E2) | BAC72090 | EC 2.3.1.168 | express or Over-Express | | Streptomyces avermitilis |

FIG. 10I

| | | | | | |
|---|---|---|---|---|---|
| bkdAA | branched-chain α-ketoacid dehydrogenase α-subunit (E1a) | NP_390285 | EC 1.2.4.4 | express or Over-Express | make branched-chain acyl-CoA precursors | *Bacillus subtilis* |
| bkdAB | branched-chain α-ketoacid dehydrogenase b-subunit (E1b) | NP_390284 | EC 1.2.4.4 | express or Over-Express | make branched-chain acyl-CoA precursors | *Bacillus subtilis* |
| bkdB | dihydrolipoyl transacetylase (E2) | NP_390283 | EC 2.3.1.168 | express or Over-Express | make branched-chain acyl-CoA precursors | *Bacillus subtilis* |
| bkdA1 | branched-chain α-ketoacid dehydrogenase α-subunit (E1a) | AAA65614 | EC 1.2.4.4 | express or Over-Express | make branched-chain acyl-CoA precursors | *Pseudomonas putida* |
| bkdA2 | branched-chain α-ketoacid dehydrogenase b-subunit (E1b) | AAA65615 | EC 1.2.4.4 | express or Over-Express | make branched-chain acyl-CoA precursors | *Pseudomonas putida* |
| bkdC | dihydrolipoyl transacetylase (E2) | AAA65617 | EC 2.3.1.168 | express or Over-Express | make branched-chain acyl-CoA precursors | *Pseudomonas putida* |
| lpd | dihydrolipoamide dehydrogenase (E3) | NP_414658 | 1.8.1.4 | express or Over-Express | make branched-chain acyl-CoA precursors | *Escherichia coli* |
| IlvE | branched-chain amino acid aminotransferase | YP_026247 | 2.6.1.42 | express or Over-Express | make branched α-ketoacids | *Escherichia coli* |
| IlvE | branched-chain amino acid aminotransferase | AAF34406 | 2.6.1.42 | express or Over-Express | make branched α-ketoacids | *Lactococcus lactis* |

FIG. 10J

| | | | | | | |
|---|---|---|---|---|---|---|
| ilvE | branched-chain amino acid aminotransferase | NP_745648 | 2.6.1.42 | express or Over-Express | make branched a-ketoacids | *Pseudomonas putida* |
| ilvE | branched-chain amino acid aminotransferase | NP_629657 | 2.6.1.42 | express or Over-Express | make branched a-ketoacids | *Streptomyces coelicolor* |
| ccr | crotonyl-CoA reductase | NP_630556 | 1.6.5.5, 1.1.1.1 | express or Over-Express | Converting crotonyl-CoA to butyryl-CoA | *Streptomyces coelicolor* |
| ccr | crotonyl-CoA reductase | AAD53915 | 1.6.5.5, 1.1.1.1 | express or Over-Express | Converting crotonyl-CoA to butyryl-CoA | *Streptomyces cinnamonensis* |
| icmA, isobutyryl-CoA mutase | isobutyryl-CoA mutase, subunit A | NP_629554 | 5.4.99.2 | express or Over-Express | converting butyryl-CoA to isobutyryl-CoA | *Streptomyces coelicolor* |
| icmA, isobutyryl-CoA mutase | isobutyryl-CoA mutase, subunit A | AAC08713 | 5.4.99.2 | express or Over-Express | converting butyryl-CoA to isobutyryl-CoA | *Streptomyces cinnamonensis* |
| icmB, isobutyryl-CoA mutase | isobutyryl-CoA mutase, subunit B | NP_630904 | 5.4.99.2 | express or Over-Express | converting butyryl-CoA to isobutyryl-CoA | *Streptomyces coelicolor* |
| icmB, isobutyryl-CoA mutase | isobutyryl-CoA mutase, subunit B | CAB59633 | 5.4.99.2 | express or Over-Express | converting butyryl-CoA to isobutyryl-CoA | *Streptomyces cinnamonensis* |
| FabH, ACPs and fabF genes with specificity for branched chain acyl-CoAs | | | | | | |
| ilvE | branched-chain amino acid aminotransferase | CAC12788 | EC 2.6.1.42 | over express | branched chain amino acid amino transferase | *Staphylococcus carnosus* |

FIG. 10K

| | | | | | |
|---|---|---|---|---|---|
| FabH1 | beta-ketoacyl-ACP synthase III | NP_626634 | 2.3.1.180 | express or Over-Express | initiation of branched-chain fatty acid biosynthesis | Streptomyces coelicolor |
| ACP | acyl-carrier protein | NP_626635 | NONE | express or Over-Express | initiation and elongation of branched-chain fatty acid biosynthesis | Streptomyces coelicolor |
| FabF | beta-ketoacyl-ACP synthase II | NP_626636 | 2.3.1.179 | express or Over-Express | elongation of branched-chain fatty acid biosynthesis | Streptomyces coelicolor |
| FabH3 | beta-ketoacyl-ACP synthase III | NP_823466 | 2.3.1.180 | express or Over-Express | initiation of branched-chain fatty acid biosynthesis | Streptomyces avermitilis |
| FabC3 (ACP) | acyl-carrier protein | NP_823467 | NONE | express or Over-Express | initiation and elongation of branched-chain fatty acid biosynthesis | Streptomyces avermitilis |
| FabF | beta-ketoacyl-ACP synthase II | NP_823468 | 2.3.1.179 | express or Over-Express | elongation of branched-chain fatty acid biosynthesis | Streptomyces avermitilis |

FIG. 10L

| | | | | | |
|---|---|---|---|---|---|
| FabH_A | beta-ketoacyl-ACP synthase III | NP_389015 | 2.3.1.180 | express or Over-Express | initiation of branched-chain fatty acid biosynthesis | *Bacillus subtilis* |
| FabH_B | beta-ketoacyl-ACP synthase III | NP_388898 | 2.3.1.180 | express or Over-Express | initiation of branched-chain fatty acid biosynthesis | *Bacillus subtilis* |
| ACP | acyl-carrier protein | NP_389474 | NONE | express or Over-Express | initiation and elongation of branched-chain fatty acid biosynthesis | *Bacillus subtilis* |
| FabF | beta-ketoacyl-ACP synthase II | NP_389016 | 2.3.1.179 | express or Over-Express | elongation of branched-chain fatty acid biosynthesis | *Bacillus subtilis* |
| SmalDRAFT_0818 | beta-ketoacyl-ACP synthase III | ZP_01643059 | 2.3.1.180 | express or Over-Express | initiation of branched-chain fatty acid biosynthesis | *Stenotrophomonas maltophilia* |
| SmalDRAFT_0821 | acyl-carrier protein | ZP_01643063 | NONE | express or Over-Express | initiation and elongation of branched-chain fatty acid biosynthesis | *Stenotrophomonas maltophilia* |
| SmalDRAFT_0822 | beta-ketoacyl-ACP synthase II | ZP_01643064 | 2.3.1.179 | express or Over-Express | elongation of branched-chain fatty acid biosynthesis | *Stenotrophomonas maltophilia* |

FIG. 10M

| | | | | | | | |
|---|---|---|---|---|---|---|---|
| | FabH | beta-ketoacyl-ACP synthase III | YP_123672 | 2.3.1.180 | express or Over-Express | initiation of branched-chain fatty acid biosynthesis | *Legionella pneumophila* |
| | ACP | acyl-carrier protein | YP_123675 | NONE | express or Over-Express | initiation and elongation of branched-chain fatty acid biosynthesis | *Legionella pneumophila* |
| | FabF | beta-ketoacyl-ACP synthase II | YP_123676 | 2.3.1.179 | express or Over-Express | elongation of branched-chain fatty acid biosynthesis | *Legionella pneumophila* |
| | FabH | beta-ketoacyl-ACP synthase III | NP_415609 | 2.3.1.180 | delete or reduce | initiation of branched-chain fatty acid biosynthesis | *Escherichia coli* |
| | FabF | beta-ketoacyl-ACP synthase II | NP_415613 | 2.3.1.179 | delete or reduce | elongation of branched-chain fatty acid biosynthesis | *Escherichia coli* |
| *To Produce Cyclic Fatty Acids* | | | | | | | |
| | AnsJ | dehydratase (putative) | not available | not available | express or Over-Express | cyclohexylcarbonyl-CoA biosynthesis | *Streptomyces collinus* |
| | AnsK | CoA ligase (putative) | not available | not available | express or Over-Express | cyclohexylcarbonyl-CoA biosynthesis | *Streptomyces collinus* |
| | AnsL | dehydrogenase (putative) | not available | not available | express or Over-Express | cyclohexylcarbonyl-CoA biosynthesis | *Streptomyces collinus* |

FIG. 10N

| | | | | | |
|---|---|---|---|---|---|
| ChcA | enoyl-CoA reductase | U72144 | EC 1.3.1.34 | express or Over-Express | cyclohexylcarbonyl-CoA biosynthesis | Streptomyces collinus |
| AnsM | oxidorecutase (putative) | not available | not available | express or Over-Express | cyclohexylcarbonyl-CoA biosynthesis | Streptomyces collinus |
| PtmJ | dehydratase (putative) | AAQ84158 | not available | express or Over-Express | cyclohexylcarbonyl-CoA biosynthesis | Streptomyces sp. HK803 |
| PtmK | CoA ligase (putative) | AAQ84158 | not available | express or Over-Express | cyclohexylcarbonyl-CoA biosynthesis | Streptomyces sp. HK803 |
| PtmL | dehydrogenase (putative) | AAQ84159 | not available | express or Over-Express | cyclohexylcarbonyl-CoA biosynthesis | Streptomyces sp. HK803 |
| ChcA | enoyl-CoA reductase | AAQ84160 | EC 1.3.1.34 | express or Over-Express | cyclohexylcarbonyl-CoA biosynthesis | Streptomyces sp. HK803 |
| PtmM | oxidorecutase (putative) | AAQ84161 | not available | express or Over-Express | cyclohexylcarbonyl-CoA biosynthesis | Streptomyces sp. HK803 |
| ChcB | enoyl-CoA isomerase | AF268489 | not available | express or Over-Express | cyclohexylcarbonyl-CoA biosynthesis | Streptomyces collinus |
| ChcB/CaiD | enoyl-CoA isomerase | NP_629292 | 4.2.1.- | express or Over-Express | cyclohexylcarbonyl-CoA biosynthesis | Streptomyces coelicolor |
| ChcB/CaiD | enoyl-CoA isomerase | NP_824296 | 4.2.1.- | express or Over-Express | cyclohexylcarbonyl-CoA biosynthesis | Streptomyces avermitilis |

FIG. 10C

2C. Saturation Level Control

| | | | | | |
|---|---|---|---|---|---|
| Sfa | Suppressor of FabA | AAN79592, AAC4390 | NONE | Over-express | increase monounsaturated fatty acids | E.coli |
| also see FabA in sec. 1 | | | | express | produce unsaturated fatty acids | |
| also see section 2A - items with :0 are unsaturated (no double bonds) and with :1 are saturated (1 double bond) | | | | | | |
| fabB | 3-oxoacyl-[acyl-carrier-protein] synthase I | BAA16180 | EC.2.3.1.41 | overexpress | modulate unsaturated fatty acid production | Escherichia coli |
| fabK | trans-2-enoyl-ACP reductase II | AAF98273 | 1.3.1.9 | express | modulate unsaturated fatty acid production | Streptococcus pneumoniae |
| fabL | enoyl-(acyl carrier protein) reductase | AAU39821 | 1.3.1.9 | express | modulate unsaturated fatty acid production | Bacillus licheniformis DSM 13 |

FIG. 10P

| | | | 4.2.1.17 | Over-express | modulate unsaturated fatty acid production | |
|---|---|---|---|---|---|---|
| | fabM | trans-2, cis-3-decenoyl-ACP isomerase | DAA05501 | | | Streptococcus mutans |
| 3. Export | | | | | | |
| | ABC transport protein | putative alkane transporter | AAN73268 | NONE | express | export products | Rhodococcus erythropolis |
| | CER5 | wax transporter | At1g51500, AY734542, At3g21090, At1g51460 | NONE | express | export products | Arabidopsis thaliana |
| | AtMRP5 | Arabidopsis thaliana multidrug resistance-associated | NP_171908 | NONE | express | export products | Arabidopsis thaliana |
| | AmiS2 | ABC transporter AmiS2 | JC5491 | NONE | express | export products | Rhodococcus sp. |
| | AtPGP1 | ARABIDOPSIS THALIANA P GLYCOPROTEIN1 | NP_181228 | NONE | express | export products | Arabidopsis thaliana |
| | AcrA | putative multidrug-efflux transport protein acrA | CAF23274 | NONE | express | export products | Candidatus Protochlamydia amoebophila UWE25 |
| | AcrB | probable multidrug-efflux transport protein, acrB | CAF23275 | NONE | express | export products | Candidatus Protochlamydia amoebophila UWE25 |
| | TolC | Outer membrane protein [Cell envelope biogenesis, | ABD59001 | NONE | express | export products | Francisella tularensis subsp. novicida |

FIG. 10Q

| | | | | | | |
|---|---|---|---|---|---|---|
| | AcrE | transmembrane protein affects septum formation and cell membrane permeability | YP_312213 | NONE | express | export products | Shigella sonnei Ss046 |
| | AcrF | Acriflavine resistance protein F | P24181 | NONE | express | export products | Escherichia coli |
| | tll1618 | multidrug efflux transporter | NP_682408.1 | NONE | express | export products | Thermosynechococcus elongatus BP-1 |
| | tll1619 | multidrug efflux transporter | NP_682409.1 | NONE | express | export products | Thermosynechococcus elongatus BP-1 |
| | tll0139 | multidrug efflux transporter | NP_680930.1 | NONE | express | export products | Thermosynechococcus elongatus BP-1 |
| 4. Fermentation | | | | | | | |
| | replication checkpoint genes | | | | | | |
| | umuD | DNA polymerase V, subunit | YP_310132 | 3.4.21.- | Over-express | increase output efficiency | Shigella sonnei Ss046 |
| | umuC | DNA polymerase V, subunit | ABC42261 | 2.7.7.7 | Over-express | increase output efficiency | Escherichia coli |
| | NADH:NADPH transhydrogenase (alpha and beta subunits) (pntA, pntB) | | P07001, P0AB70 | 1.6.1.2 | express | increase output efficiency | Shigella flexneri |

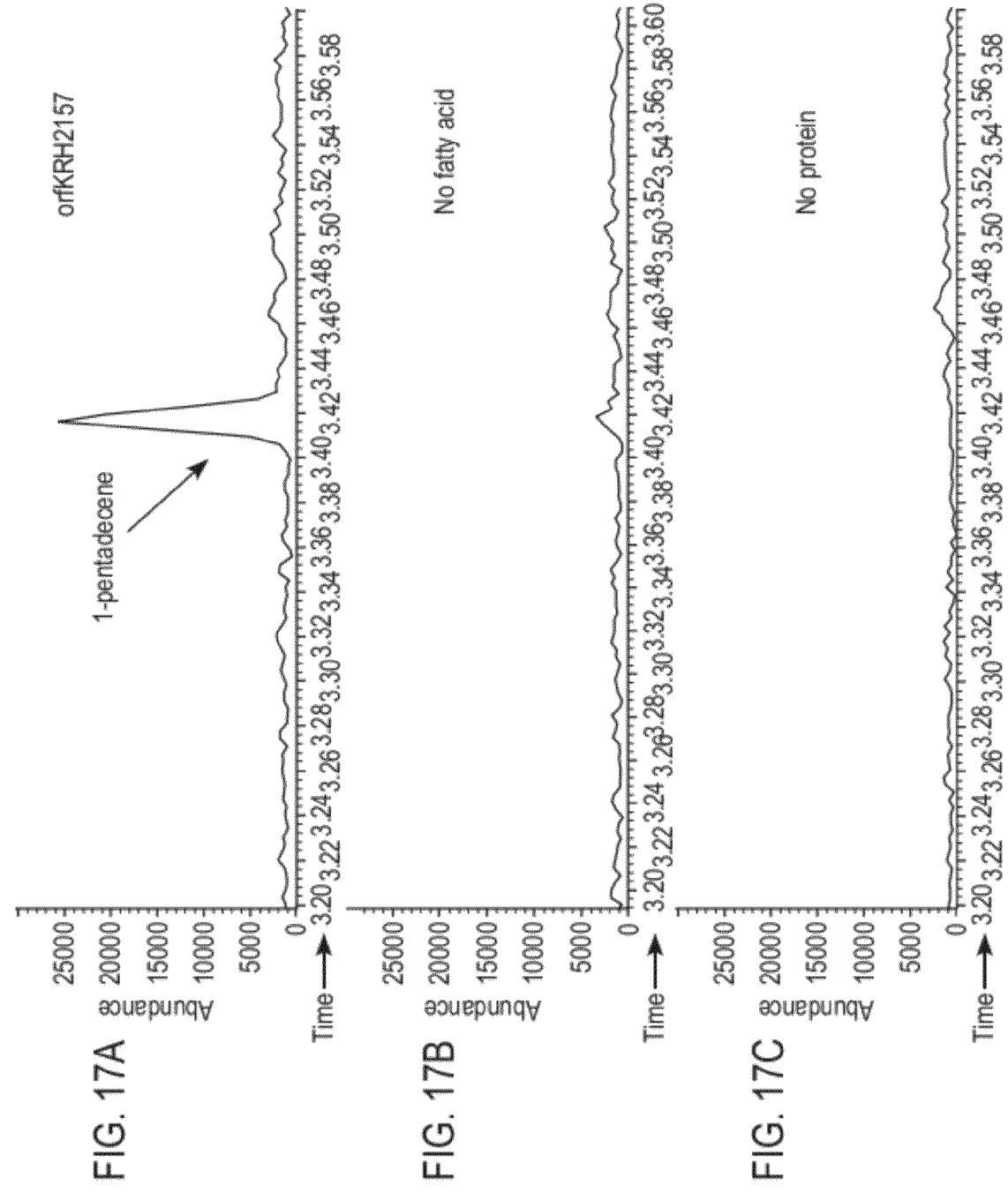

Additional Table: P450 Peroxygenase family (CYP152)

| Organism | GeneBank Acc. # | Pos. 85[1] | %ID[1] |
|---|---|---|---|
| Jeotgalicoccus sp. ATCC8456 | orf880 | His | 100 |
| Arthrobacter sp. FB24 | ZP_00413206 | Gln | 32.7 |
| Aurantimonas sp. SI85-9A1 | ZP_01227146 | Gln | 34.7 |
| Bacillus amyloliquefaciens FZB42 | ABS73471 | Gln | 40.8 |
| Bacillus clausii KSM-K16 | YP_176535 | Gln | 37.4 |
| Bacillus coahuilensis m4-4 | ZP_03227611 | Gln | 40.2 |
| Bacillus coagulans 36D1 | EAY45396 | Gln | 37.1 |
| Bacillus halodurans C-125 | NP_242623 | Gln | 35.9 |
| Bacillus subtilis str. 168 | NP_388092 | Gln | 41.2 |
| Bacillus sp. NRRLB-14911 | ZP_01169817 | Gln | 39.6 |
| Brevundimonas sp. BAL3 | EDX80366 | Gln | 32.4 |
| Clostridium acetobutylicum ATCC 824 | NP_349922 | Gln | 39.1 |
| Clostridium botulinum F str. Langeland | ABS41685 | Gln | 40.2 |
| Clostridium botulinum NCTC 2916 | ZP_02613119 | Gln | 40.7 |
| Clostridium botulinum A str. ATCC 19397 | ABS33032 | Gln | 40.0 |
| Clostridium botulinum Bf | ZP_02617555 | Gln | 40.7 |
| Clostridium botulinum A3 str. Loch Maree | YP_001786433 | Gln | 40.5 |
| Clostridium botulinum B1 str. Okra | YP_001780672 | Gln | 40.0 |
| Clostridium botulinum A str. ATCC 3502 | YP_001253569 | Gln | 40.0 |
| Clostridium phytofermentans ISDg | ZP_01354055 | Gln | 37.1 |
| Clostridium sporogenes ATCC 15579 | ZP_02994641 | Gln | 40.0 |
| Corynebacterium efficiens YS-314 | NP_739069 | His | 28.8 |
| Cyanothece sp. CCY0110 | EAZ92180 | Gln | 36.2 |
| Enterococcus faecium DO | ZP_00604550 | Gln | 28.4 |
| Exiguobacterium sp. AT1b | ZP_02991092 | Gln | 34.5 |
| Kocuria rhizophila DC2201 | YP_001856010 | His | 29.8 |
| Mesorhizobium sp. BNC1 | YP_665837 | Gln | 36.2 |
| Mesorhizobium sp. BNC1 | YP_676050 | Gln | 29.9 |
| Methylobacillus flagellatus KT | YP_545551 | Gln | 34.4 |
| Methylobacterium populi BJ001 | EDO73824 | Met | 31.3 |
| Methylobacterium sp. 4-46 | EDK95996 | Met | 35.2 |
| Oceanicola batsensis HTCC2597 | ZP_01000316 | Gln | 30.8 |
| Oceanobacillus iheyensis HTE831 | NP_694023 | Phe | 30.9 |
| Pseudomonas stutzeri A1501 | ABP80913 | Gln | 32.9 |
| Planctomyces maris DSM 8797 | EDL56759 | Gln | 32.0 |
| Rhodobacter sphaeroides 2.4.1 | YP_352437 | Gln | 30.9 |
| Rhodobacter sphaeroides ATCC 17025 | ZP_00915817 | Gln | 30.6 |
| Rhodobacter sphaeroides ATCC 17029 | ZP_00918496 | Gln | 31.1 |
| Sphingomonas paucimobilis | BAA22987 | Gln | 36.0 |
| Sphingopyxis alaskensis RB2256 | YP_617595 | Gln | 35.2 |
| Streptomyces albus | ABS90483 | His | 34.6 |
| Streptomyces pristinaespiralis ATCC 25486 | YP_002196443 | His | 33.2 |
| Streptomyces sp. Mg1 | ZP_03175040 | His | 34.9 |
| Sulfitobacter sp. NAS-14.1 | ZP_00964321 | Gln | 34.1 |
| Xanthomonas campestris str. 8004 | YP_243267 | Gln | 27.4 |

1: in relation to Jeotgalicoccus orf880

FIG. 22

SEQUENCE LISTING

<160> NUMBER OF SEQ ID NOS: 14

<210> SEQ ID NO 1
<211> LENGTH: 1269
<212> TYPE: DNA
<213> ORGANISM: Jeotgalicoccus sp. ATCC8456

<400> SEQUENCE: 1
atggcaacac ttaagaggga taagggctta gataatactt tgaaagtatt aaagcaaggt      60
tatctttaca caacaaatca gagaaatcgt ctaaacacat cagttttcca aactaaagca     120
ctcggtggta aaccattcgt agttgtgact ggtaaggaag gcgctgaaat gttctacaac     180

```
aatgatgttg ttcaacgtga aggcatgtta ccaaaacgta tcgttaatac gcttttggt      240
aaaggtgcaa tccatacggt agatggtaaa aaacacgtag acagaaaagc attgttcatg     300
agcttgatga ctgaaggtaa cttgaattat gtacgagaat taacgcgtac attatggcat     360
gcgaacacac aacgtatgga agtatggat gaggtaaata tttaccgtga atctatcgta      420
ctacttacaa aagtaggaac acgttgggca ggcgttcaag caccacctga agatatcgaa     480
agaatcgcaa cagacatgga catcatgatc gattcattta gagcacttgg tggtgccttt     540
aaaggttaca aggcatcaaa agaagcacgt cgtcgtgttg aagattggtt agaagaacaa     600
attattgaga ctcgtaaagg gaatattcat ccaccagaag gtacagcact ttacgaattt     660
gcacattggg aagactactt aggtaaccca atggactcaa gaacttgtgc gattgactta     720
atgaacacat tccgcccatt aatcgcaatc aacagattcg tttcattcgg tttacacgcg     780
atgaacgaaa acccaatcac acgtgaaaaa attaaatcag aacctgacta tgcatataaa     840
ttcgctcaag aagttcgtcg ttactatcca ttcgttccat tccttccagg taaagcgaaa     900
gtagacatcg acttccaagg cgttacaatt cctgcaggtg taggtcttgc attagatgtt     960
tatggtacaa cgcatgatga atcactttgg gacgatccaa tgaattccg cccagaaaga    1020
ttcgaaactt gggacggatc accatttgac cttattccac aaggtggtgg agattactgg    1080
acaaatcacc gttgtgcagg tgaatggatc acagtaatca tcatggaaga aacaatgaaa    1140
tactttgcag aaaaaataac ttatgatgtt ccagaacaag atttagaagt ggacttaaac    1200
agtatcccag gatacgttaa gagtggcttt gtaatcaaaa atgttcgcga agttgtagac    1260
agaacataa                                                             1269

<210> SEQ ID NO 2
<211> LENGTH: 422
<212> TYPE: PRT
<213> ORGANISM: Jeotgalicoccus sp. ATCC8456

<400> SEQUENCE: 2

Met Ala Thr Leu Lys Arg Asp Lys Gly Leu Asp Asn Thr Leu Lys Val
1               5                   10                  15

Leu Lys Gln Gly Tyr Leu Tyr Thr Thr Asn Gln Arg Asn Arg Leu Asn
            20                  25                  30

Thr Ser Val Phe Gln Thr Lys Ala Leu Gly Gly Lys Pro Phe Val Val
        35                  40                  45

Val Thr Gly Lys Glu Gly Ala Glu Met Phe Tyr Asn Asn Asp Val Val
    50                  55                  60

Gln Arg Glu Gly Met Leu Pro Lys Arg Ile Val Asn Thr Leu Phe Gly
65                  70                  75                  80

Lys Gly Ala Ile His Thr Val Asp Gly Lys His Val Asp Arg Lys
                85                  90                  95

Ala Leu Phe Met Ser Leu Met Thr Glu Gly Asn Leu Asn Tyr Val Arg
            100                 105                 110

Glu Leu Thr Arg Thr Leu Trp His Ala Asn Thr Gln Arg Met Glu Ser
        115                 120                 125

Met Asp Glu Val Asn Ile Tyr Arg Glu Ser Ile Val Leu Leu Thr Lys
    130                 135                 140

Val Gly Thr Arg Trp Ala Gly Val Gln Ala Pro Pro Glu Asp Ile Glu
145                 150                 155                 160

Arg Ile Ala Thr Asp Met Asp Ile Met Ile Asp Ser Phe Arg Ala Leu
                165                 170                 175

Gly Gly Ala Phe Lys Gly Tyr Lys Ala Ser Lys Glu Ala Arg Arg Arg
```

```
                180                185                190
Val Glu Asp Trp Leu Glu Glu Gln Ile Ile Glu Thr Arg Lys Gly Asn
        195                200                205

Ile His Pro Pro Glu Gly Thr Ala Leu Tyr Glu Phe Ala His Trp Glu
        210                215                220

Asp Tyr Leu Gly Asn Pro Met Asp Ser Arg Thr Cys Ala Ile Asp Leu
225                230                235                240

Met Asn Thr Phe Arg Pro Leu Ile Ala Ile Asn Arg Phe Val Ser Phe
                245                250                255

Gly Leu His Ala Met Asn Glu Asn Pro Ile Thr Arg Glu Lys Ile Lys
            260                265                270

Ser Glu Pro Asp Tyr Ala Tyr Lys Phe Ala Gln Glu Val Arg Arg Tyr
        275                280                285

Tyr Pro Phe Val Pro Phe Leu Pro Gly Lys Ala Lys Val Asp Ile Asp
        290                295                300

Phe Gln Gly Val Thr Ile Pro Ala Gly Val Gly Leu Ala Leu Asp Val
305                310                315                320

Tyr Gly Thr Thr His Asp Glu Ser Leu Trp Asp Asp Pro Asn Glu Phe
                325                330                335

Arg Pro Glu Arg Phe Glu Thr Trp Asp Gly Ser Pro Phe Asp Leu Ile
            340                345                350

Pro Gln Gly Gly Gly Asp Tyr Trp Thr Asn His Arg Cys Ala Gly Glu
        355                360                365

Trp Ile Thr Val Ile Ile Met Glu Glu Thr Met Lys Tyr Phe Ala Glu
        370                375                380

Lys Ile Thr Tyr Asp Val Pro Glu Gln Asp Leu Glu Val Asp Leu Asn
385                390                395                400

Ser Ile Pro Gly Tyr Val Lys Ser Gly Phe Val Ile Lys Asn Val Arg
                405                410                415

Glu Val Val Asp Arg Thr
            420

<210> SEQ ID NO 3
<211> LENGTH: 1507
<212> TYPE: DNA
<213> ORGANISM: Jeotgalicoccus sp. ATCC8456

<400> SEQUENCE: 3
ggttaccttg ttacgacttc accccaatta tcaatcccac ctttgacggc tacctccatt      60
aaggttagtc caccggcttc aggtgttayc gactttcgtg gtgtgacggg cggtgtgtac     120
aagacccggg aacgtattca ccgtagcatg ctgatctacg attactagcg attccagctt     180
catggagtcg agttgcagac tccaatccga actgagaaca gttttatggg attcgcttgg     240
cctcgcggct tcgctgccct tgtaacctgc ccattgtag cacgtgtgta gcccaaatca     300 taagggcat gatgatttga cgtcatcccc accttcctcc ggtttgtcac cggcagtcaa     360
tctagagtgc ccaactgaat gatggcaact aaatttaagg gttgcgctcg ttgcgggact     420
taacccaaca tctcacgaca cgagctgacg acaaccatgc accacctgtc tctctgccca     480
aaagggaaac catatctctr tggcgatcag aggatgtcaa gatttggtaa ggttcttcgc     540
gttgcttcga attaaaccac atgctccacc gcttgtgcgg gtccccgtca attcctttga     600
gtttcaacct gcggtcgta ctccccaggc ggagtgctta atgcgttagc tgcagcactg     660 agggggcggaa accccccaac acttagcact catcgtttac ggcgtggact accagggtat     720
ctaatcctgt ttgatcccca cgctttcgca cctcagcgtc agttacagac cagagagccg     780
```

```
ccttcgccca ctggtgttcc tccatatctc tgcgcatttc accgctacac atggaattcc      840
actctcctct tctgcactca agtaaaacag tttccaatga ccctcccgg  ttgagccggg      900 ggctttcaca tcagacttat tctaccgcct acgcgcgctt tacgcccaat aattccggat      960
aacgcttgcc acctacgtat taccgcggct gctggcacgt agttagccgt ggctttctgg     1020
ttaagtaccg tcatctctag gccagttact acctaaagtg ttcttcctta acaacagagt     1080
tttacgagcc gaaacccttc ttcactcacg cggcgttgct ccgtcagact tgcgtycatt     1140
gcggaagatt ccctactgct gcctcccgta ggagtctggg ccgtgtctca gtcccagtgt     1200
ggccgatcac cctctcaggt cggctatgca tcgttgcctt ggtgagccac tacctcacca     1260
actagctaat gcaccgcagg cccatccttt agtgacagat aaatccgcct tcattaaga     1320 ttacttgtgt aatccaactt atccggtatt agctaccgtt tccggtagtt atcccagtct     1380
aaagggtagg ttgcccacgt gttactcacc cgtccgccgc tcgattgtaa ggagcaagct     1440
ccttacgctc gcgctcgact tgcatgtatt aggcacgccg ccagcgttca tcctgagcca     1500
ggatcaa                                                               1507

<210> SEQ ID NO 4
<211> LENGTH: 1209
<212> TYPE: DNA
<213> ORGANISM: Jeotgalicoccus sp. ATCC8456

<400> SEQUENCE: 4
atggctactc tgaaacgtga caaaggtctg gataacactc tgaaagttct gaaacaaggt       60
tacctgtaca ctaccaacca gcgcaaccgt ctgaacacca gcgtctttca aaccaaagcc      120
ctgggtggca aaccgttcgt ggttgtgacc ggcaaagaag gcgcagagat gttctataac      180
aacgatgtgg tgcagcgtga gggcatgctg ccgaaacgta ttgtaaacac cctgttcggc      240
aagggtgcga tccataccgt ggatggcaag aaacacgtag accgtaaagc actgttcatg      300
tctctgatga ctgagggcaa cctgaactat gtacgtgaac tgacccgcac cctgtggcat      360
gcgaacacgc agcgtatgga atctatggat gaggtgaaca tctaccgtga aagcatcgtt      420
ctgctgacga aggtgggcac ccgctgggca ggtgttcagg caccgccgga ggacattgag      480
cgcatcgcta ccgatatgga tattatgatc gatagcttcc gtgctctggg tggcgcattt      540
atcatcgaaa cccgtaaagg taacatccac ccaccggaag gtacggctct gtacgaattt      600
gcacactggg aggattatct gggtaatcca atggactctc gtacctgcgc gatcgatctg      660
atgaacacgt ttcgcccgct gatcgctatc aaccgctttg tttctttcgg tctgcacgcg      720
atgaacgaaa acccgatcac tcgtgagaag attaagtccg agccggatta cgcatacaaa      780
ttcgcacagg aggtccgtcg ctactacccg ttcgttcctt tcctgccggg taaagcaaag      840
gtagacatcg acttccaggg tgtaaccatc ccagccggtg tgggcctggc actggatgtt      900
tacggtacca cccatgatga aagcctgtgg gatgatccga acgaatttcg cccggagcgt      960
ttcgagactt gggatggttc tccatttgac ctgattccgc aaggtggtgg tgattactgg     1020
accaatcacc gctgtgccgg cgagtggatc accgtcatta tcatggaaga aacgatgaaa     1080
tacttcgccg agaaaatcac ttatgacgtt ccagaacagg acctggaagt agatctgaac     1140
tccatcccgg gctatgtcaa aagcggcttt gttatcaaaa acgtccgtga agtagtcgat     1200
cgcacctaa                                                            1209

<210> SEQ ID NO 5
<211> LENGTH: 422
```

-continued

```
<212> TYPE: PRT
<213> ORGANISM: Jeotgalicoccus sp. ATCC8456

<400> SEQUENCE: 5
```

Met Ala Thr Leu Lys Arg Asp Lys Gly Leu Asp Asn Thr Leu Lys Val
1               5                   10                  15

Leu Lys Gln Gly Tyr Leu Tyr Thr Thr Asn Gln Arg Asn Arg Leu Asn
            20                  25                  30

Thr Ser Val Phe Gln Thr Lys Ala Leu Gly Gly Lys Pro Phe Val Val
        35                  40                  45

Val Thr Gly Lys Glu Gly Ala Glu Met Phe Tyr Asn Asn Asp Val Val
    50                  55                  60

Gln Arg Glu Gly Met Leu Pro Lys Arg Ile Val Asn Thr Leu Phe Gly
65                  70                  75                  80

Lys Gly Ala Ile His Thr Val Asp Gly Lys His Val Asp Arg Lys
                85                  90                  95

Ala Leu Phe Met Ser Leu Met Thr Glu Gly Asn Leu Asn Tyr Val Arg
            100                 105                 110

Glu Leu Thr Arg Thr Leu Trp His Ala Asn Thr Gln Arg Met Glu Ser
        115                 120                 125

Met Asp Glu Val Asn Ile Tyr Arg Glu Ser Ile Val Leu Leu Thr Lys
130                 135                 140

Val Gly Thr Arg Trp Ala Gly Val Gln Ala Pro Pro Glu Asp Ile Glu
145                 150                 155                 160

Arg Ile Ala Thr Asp Met Asp Ile Met Ile Asp Ser Phe Arg Ala Leu
                165                 170                 175

Gly Gly Ala Phe Lys Gly Tyr Lys Ala Ser Lys Glu Ala Arg Arg Arg
            180                 185                 190

Val Glu Asp Trp Leu Glu Glu Gln Ile Ile Glu Thr Arg Lys Gly Asn
        195                 200                 205

Ile His Pro Pro Glu Gly Thr Ala Leu Tyr Glu Phe Ala His Trp Glu
210                 215                 220

Asp Tyr Leu Gly Asn Pro Met Asp Ser Arg Thr Cys Ala Ile Asp Leu
225                 230                 235                 240

Met Asn Thr Phe Arg Pro Leu Ile Ala Ile Asn Arg Phe Val Ser Phe
                245                 250                 255

Gly Leu His Ala Met Asn Glu Asn Pro Ile Thr Arg Glu Lys Ile Lys
            260                 265                 270

Ser Glu Pro Asp Tyr Ala Tyr Lys Phe Ala Gln Glu Val Arg Arg Tyr
        275                 280                 285

Tyr Pro Phe Val Pro Phe Leu Pro Gly Lys Ala Lys Val Asp Ile Asp
290                 295                 300

Phe Gln Gly Val Thr Ile Pro Ala Gly Val Gly Leu Ala Leu Asp Val
305                 310                 315                 320

Tyr Gly Thr Thr His Asp Glu Ser Leu Trp Asp Pro Asn Glu Phe
                325                 330                 335

Arg Pro Glu Arg Phe Glu Thr Trp Asp Gly Ser Pro Phe Asp Leu Ile
            340                 345                 350

Pro Gln Gly Gly Gly Asp Tyr Trp Thr Asn His Arg Cys Ala Gly Glu
        355                 360                 365

Trp Ile Thr Val Ile Ile Met Glu Glu Thr Met Lys Tyr Phe Ala Glu
370                 375                 380

Lys Ile Thr Tyr Asp Val Pro Glu Gln Asp Leu Glu Val Asp Leu Asn
385                 390                 395                 400

Ser Ile Pro Gly Tyr Val Lys Ser Gly Phe Val Ile Lys Asn Val Arg
        405                 410                 415

Glu Val Val Asp Arg Thr
        420

<210> SEQ ID NO 6
<211> LENGTH: 1308
<212> TYPE: DNA
<213> ORGANISM: Corynebacterium efficiens

<400> SEQUENCE: 6

| | | | | | |
|---|---|---|---|---|---|
| tcagcgttcc | acgcgcaccc | gcatgccggt | ttcggagcgg | gtgagcatct | gtgtccaggg | 60 |
| gaaacgggta | tcagccggat | ccgtggagag | caccacaccg | ggccggcata | aagcctccac | 120 |
| catggctgtg | agcgcggcca | tggcgatctt | ctcgcccggg | cagcggtgac | cggtgtacac | 180 |
| cccggctccg | ccctggggca | cgaagctggt | gagcctctca | tagtcctcct | gggtgcccag | 240 |
| gtcctcccgg | gacaggaaac | gctccggttg | aaacgcactc | gggttctccc | actcattggg | 300 |
| gtcggtgttg | gtgccgtaga | tgtcgatgat | cacgcgttca | ccctcatgca | cggggcagcc | 360 |
| ctggatttcg | gtgtcggtgg | tggcgatggc | cggcagcatg | gcacaaacg | gatagacgcg | 420 |
| gcggacctcc | tgggcgaagg | cgaaggccac | gggctgtcct | ccctcgcgga | tcttctccac | 480 |
| ccactcgggg | tgctcgacca | gggcgctgcc | ggcgaaggag | gcgaacagtg | atactgccac | 540 |
| ggtgggacgg | gtgaggttct | gtaattcgat | gccggcgatg | gaggcgtcga | caagctcccc | 600 |
| gtccggaccg | accaaccggg | acatggcctc | cagggcgcta | ccggcgcca | cgtgccgctc | 660 |
| cccggcgcgc | gcctgcctga | tgagcttcaa | ggcccacctg | ttcaaccgcg | cccggttgat | 720 |
| ccagcccagg | gcgtgccctt | tgaggggatg | gccgaactga | tagaccagct | cggccatctg | 780 |
| atgggcgcgc | cggctggctt | ccttctggct | aagctcaatg | cccgcccaac | ggtaggccgc | 840 |
| acgcccgaag | ccagcgccg | caccgtcata | gaccgtcccg | ggttcgcggg | cccagtcctg | 900 |
| caccacacgg | tccacctcac | ggcggacgag | tgcatcgaac | tcggcgacct | tgtcatcgtc | 960 |
| ataggcgaca | tcggcgagct | gacgtttgcg | cagacggtgc | tcctcgccgt | ccagcgaatg | 1020 |
| caccgcaccc | tcaccgaaca | gggggatgcg | gatcaccgcg | ggcatggctc | cgtcacgttt | 1080 |
| catccggtca | ttgtcataga | acagctccac | tccggctgaa | ccgcgcacga | tggtgacggg | 1140 |
| tttgaacagc | atgcgcgacc | gcagcggggt | gttggcatcg | ggtgagatac | cggccttgcg | 1200 |
| gcgcagacgg | gagagaaaaa | ggtagccgtg | gcgcagcagg | ttgggggcct | gttcgccggg | 1260 |
| ggcaaagggg | caggaggatg | tctgagtcat | cggtgggacc | tcttccaa | | 1308 |

<210> SEQ ID NO 7
<211> LENGTH: 435
<212> TYPE: PRT
<213> ORGANISM: Corynebacterium efficiens

<400> SEQUENCE: 7

Met Glu Glu Val Pro Pro Met Thr Gln Thr Ser Ser Cys Pro Phe Ala
1               5                   10                  15

Pro Gly Glu Gln Ala Pro Asn Leu Leu Arg His Gly Tyr Leu Phe Leu
            20                  25                  30

Ser Arg Leu Arg Arg Lys Ala Gly Ile Ser Pro Asp Ala Asn Thr Pro
        35                  40                  45

Leu Arg Ser Arg Met Leu Phe Lys Pro Val Thr Ile Val Arg Gly Ser
    50                  55                  60

Ala Gly Val Glu Leu Phe Tyr Asp Asn Asp Arg Met Lys Arg Asp Gly
65                  70                  75                  80

Ala Met Pro Ala Val Ile Arg Ile Pro Leu Phe Gly Glu Gly Ala Val
            85                  90                  95

His Ser Leu Asp Gly Glu His Arg Leu Arg Lys Arg Gln Leu Ala
            100                 105                 110

Asp Val Ala Tyr Asp Asp Lys Val Ala Glu Phe Asp Ala Leu Val
            115                 120                 125

Arg Arg Glu Val Asp Arg Val Val Gln Asp Trp Ala Arg Glu Pro Gly
130                 135                 140

Thr Val Tyr Asp Gly Ala Ala Leu Ala Phe Gly Arg Ala Ala Tyr Arg
145                 150                 155                 160

Trp Ala Gly Ile Glu Leu Ser Gln Lys Glu Ala Ser Arg Arg Ala His
                165                 170                 175

Gln Met Ala Glu Leu Val Tyr Gln Phe Gly His Pro Leu Lys Gly His
            180                 185                 190

Ala Leu Gly Trp Ile Asn Arg Ala Arg Leu Asn Arg Trp Ala Leu Lys
            195                 200                 205

Leu Ile Arg Gln Ala Arg Ala Gly Glu Arg His Val Ala Pro Gly Ser
210                 215                 220

Ala Leu Glu Ala Met Ser Arg Leu Val Gly Pro Asp Gly Glu Leu Val
225                 230                 235                 240

Asp Ala Ser Ile Ala Gly Ile Glu Leu Gln Asn Leu Thr Arg Pro Thr
                245                 250                 255

Val Ala Val Ser Leu Phe Ala Ser Phe Ala Gly Ser Ala Leu Val Glu
            260                 265                 270

His Pro Glu Trp Val Glu Lys Ile Arg Glu Gly Gln Pro Val Ala
            275                 280                 285

Phe Ala Phe Ala Gln Glu Val Arg Arg Val Tyr Pro Phe Val Pro Met
290                 295                 300

Leu Pro Ala Ile Ala Thr Thr Asp Thr Glu Ile Gln Gly Cys Pro Val
305                 310                 315                 320

His Glu Gly Glu Arg Val Ile Ile Asp Ile Tyr Gly Thr Asn Thr Asp
                325                 330                 335

Pro Asn Glu Trp Glu Asn Pro Ser Ala Phe Gln Pro Glu Arg Phe Leu
            340                 345                 350

Ser Arg Glu Asp Leu Gly Thr Gln Glu Asp Tyr Glu Arg Leu Thr Ser
            355                 360                 365

Phe Val Pro Gln Gly Gly Ala Gly Val Tyr Thr Gly His Arg Cys Pro
370                 375                 380

Gly Glu Lys Ile Ala Met Ala Ala Leu Thr Ala Met Val Glu Ala Leu
385                 390                 395                 400

Cys Arg Pro Gly Val Val Leu Ser Thr Asp Pro Ala Asp Thr Arg Phe
                405                 410                 415

Pro Trp Thr Gln Met Leu Thr Arg Ser Glu Thr Gly Met Arg Val Arg
            420                 425                 430

Val Glu Arg
        435

<210> SEQ ID NO 8
<211> LENGTH: 1287
<212> TYPE: DNA
<213> ORGANISM: Kokuria rhizophila

<400> SEQUENCE: 8
atgacttcac cgttcggtca gacccgttcc gagcagggcc cgtccctact ccgctccggc     60

```
tacctctttg cctcccgcgc acgacgccgc gcgggcctct cctccgactc ggggtgcccc      120
gtccgcatgc ctctgctggg caagcagacc gtcctggtcc gcggcgagga gggcgtcaag      180
ctcttctacg acacctcccg cgtgcggcgc gacggcgcca tgcccggagt cgtgcagggg      240
ccgctcttcg gtgcgggcgc cgtgcacggg ctggacggcg aggcccaccg ggtgcgcaag      300
aaccaactcg cggacatggc ctacgaggac gagcgcgtgg cggcctacaa gcccttcgtg      360
gcggaggagc tcgagaacct cgtcgcgcgg tggaaggacg cgataacgt ctacgacagc       420 accgccatcg ccttcggccg cgcgtccttc cggtgggccg gtctgcagtg gggcgtgccg      480
gagatggacc gctgggcccg ccgcatgagc cgcctgctgg acaccttcgg cgcccccgcc      540
acgcacctgg tgtcccggct ggaccggatc gccctggacc gccgcttcgc cgcgctcatc      600
aaggacgtgc gcgcgggcaa ggtcaacgca cccgaggact ccgtgctcgc gcacatggcc      660
gccctggtgg acgagcacgg cgagctggtg gacgcgaaga ccgcgggcat cgagctgcag      720
aacctcaccc gcccgaacgt ggccgtggcc cgcttcgccg cgttcgcggc caccgccctg      780
gtggagcacc ctgagtgggt cgagcgcatc cgcgccgcct ccgagcagcg cggcggcacc      840
ctgctggacg tccccgaggc cgtggccttc gcgcaggagg tccgccgcgt ctacccgttc      900
gtgcccatgc tccccgcgga ggtcacacag gacaccgaga tccagggctg ccccgtgcac      960 aaggggagc gcgtggtcct ggacatcctg gcaccaaca cggatccgac gtcctgggac       1020
cgcgcggcca cgttcgaccc cgagcgcttc ctggggtcg aggacgccga ggcgatcacc       1080
acgttcatcc cccagggcgg cgctgaggtc cgcacgggcc accgctgccc cggcgagaag      1140
atcgcggtca cgtccctctc cgccgccgtg gtggcgctgt gccggccgga ggtccagctg      1200
ccgggcgacc aggacgacct cacgttctcg tggacccaca tgctgacccg cccggtcacc      1260
ggggtgcggg tccgcaccac ccgctga                                         1287
```

<210> SEQ ID NO 9
<211> LENGTH: 1287
<212> TYPE: DNA
<213> ORGANISM: Kokuria rhizophila

<400> SEQUENCE: 9

```
atgacgagcc cgttcggcca gacccgtagc gaacagggcc cgagcctgct gcgttcgggt       60
tacttgtttg caagccgcgc tcgccgccgt gctggcctga gcagcgatag cggttgtcca      120
gttcgcatgc cgctgctggg taagcaaacg gttctggtgc gcggcgagga aggcgtcaaa      180
ctgttctatg ataccagccg tgttcgtcgt gacggcgcga tgccaggcgt cgtgcagggc      240
cctctgttcg gtgcaggtgc ggttcacggt ctggacggcg aagcgcaccg cgttcgcaag      300
aaccaactgg cggatatggc ttatgaagat gaacgtgtgg ctgcgtacaa gccgttcgtt      360
gcggaagagt tggagaatct ggttgcacgt tggaaagatg gtgacaacgt ctacgacagc      420
acggcaattg catttggccg cgcatctttt cgttgggccg gtctgcagtg gggtgtgccg      480
gagatggatc gctgggcacg ccgcatgagc cgtctgttgg ataccttcgg tcgtccggcc      540
acgcacctgg tgagccgttt ggaccgtatt gctttggatc gccgctttgc agcattgatt      600
aaggacgtgc gtgccggtaa agtgaacgct ccggaagaca gcgtcctggc ccacatggca      660
gctctggtcg acgagcatgg tgaattggtg gatgctaaga cggcgggtat cgaactgcag      720
aatttgaccc gtccgaatgt ggcggtggct cgttttgcgg cctttgcggc gacggcactg      780
gttgagcatc cggagtgggt cgaacgtatt cgtcagcct ccgaacagcg tggcggtacc       840
ttgctggacg ttccggaggc cgtggcgttc gcgcaggaag ttcgtcgcgt ctacccgttt      900
```

```
gtcccgatgc tgccagctga agttacccag gacaccgaga tccagggttg tccggttcac    960
aagggtgagc gcgtggttct ggatattttg ggtaccaata ccgatccgac cagctgggac   1020
cgtgcggcga cctttgaccc ggagcgcttt ctgggtgttg aggacgcgga agccatcacc   1080
acctttatcc gcagggcggt gcagaggtg cgtacgggcc atcgctgtcc gggtgagaag   1140
atcgccgtca ccagcctgag cgctgctgtc gttgcgctgt gtcgcccgga ggtgcaactg   1200
ccgggtgatc aggatgatct gactttagc tggaccccaca tgctgacgcg ccctgtcacg   1260
ggtgttcgcg tccgcaccac gcgctaa                                        1287

<210> SEQ ID NO 10
<211> LENGTH: 428
<212> TYPE: PRT
<213> ORGANISM: Kokuria rhizophila

<400> SEQUENCE: 10
```

Met Thr Ser Pro Phe Gly Gln Thr Arg Ser Glu Gln Gly Pro Ser Leu
1               5                   10                  15

Leu Arg Ser Gly Tyr Leu Phe Ala Ser Arg Ala Arg Arg Ala Gly
            20                  25                  30

Leu Ser Ser Asp Ser Gly Cys Pro Val Arg Met Pro Leu Leu Gly Lys
        35                  40                  45

Gln Thr Val Leu Val Arg Gly Glu Gly Val Lys Leu Phe Tyr Asp
    50                  55                  60

Thr Ser Arg Val Arg Arg Asp Gly Ala Met Pro Gly Val Val Gln Gly
65                  70                  75                  80

Pro Leu Phe Gly Ala Gly Ala Val His Gly Leu Asp Gly Glu Ala His
                85                  90                  95

Arg Val Arg Lys Asn Gln Leu Ala Asp Met Ala Tyr Glu Asp Glu Arg
            100                 105                 110

Val Ala Ala Tyr Lys Pro Phe Val Ala Glu Glu Leu Glu Asn Leu Val
        115                 120                 125

Ala Arg Trp Lys Asp Gly Asp Asn Val Tyr Asp Ser Thr Ala Ile Ala
    130                 135                 140

Phe Gly Arg Ala Ser Phe Arg Trp Ala Gly Leu Gln Trp Gly Val Pro
145                 150                 155                 160

Glu Met Asp Arg Trp Ala Arg Arg Met Ser Arg Leu Leu Asp Thr Phe
                165                 170                 175

Gly Arg Pro Ala Thr His Leu Val Ser Arg Leu Asp Arg Ile Ala Leu
            180                 185                 190

Asp Arg Arg Phe Ala Ala Leu Ile Lys Asp Val Arg Ala Gly Lys Val
        195                 200                 205

Asn Ala Pro Glu Asp Ser Val Leu Ala His Met Ala Ala Leu Val Asp
    210                 215                 220

Glu His Gly Glu Leu Val Asp Ala Lys Thr Ala Gly Ile Glu Leu Gln
225                 230                 235                 240

Asn Leu Thr Arg Pro Asn Val Ala Val Ala Arg Phe Ala Ala Phe Ala
                245                 250                 255

Ala Thr Ala Leu Val Glu His Pro Glu Trp Val Glu Arg Ile Arg Ala
            260                 265                 270

Ala Ser Glu Gln Arg Gly Gly Thr Leu Leu Asp Val Pro Glu Ala Val
        275                 280                 285

Ala Phe Ala Gln Glu Val Arg Arg Val Tyr Pro Phe Val Pro Met Leu
    290                 295                 300

Pro Ala Glu Val Thr Gln Asp Thr Glu Ile Gln Gly Cys Pro Val His

```
                305                 310                 315                 320
Lys Gly Glu Arg Val Val Leu Asp Ile Leu Gly Thr Asn Thr Asp Pro
                    325                 330                 335

Thr Ser Trp Asp Arg Ala Ala Thr Phe Asp Pro Glu Arg Phe Leu Gly
                340                 345                 350

Val Glu Asp Ala Glu Ala Ile Thr Thr Phe Ile Pro Gln Gly Gly Ala
            355                 360                 365

Glu Val Arg Thr Gly His Arg Cys Pro Gly Glu Lys Ile Ala Val Thr
        370                 375                 380

Ser Leu Ser Ala Ala Val Val Ala Leu Cys Arg Pro Glu Val Gln Leu
385                 390                 395                 400

Pro Gly Asp Gln Asp Asp Leu Thr Phe Ser Trp Thr His Met Leu Thr
                405                 410                 415

Arg Pro Val Thr Gly Val Arg Val Arg Thr Thr Arg
                420                 425

<210> SEQ ID NO 11
<211> LENGTH: 1275
<212> TYPE: DNA
<213> ORGANISM: Methylobacterium populi

<400> SEQUENCE: 11
atgccggctg ccattgccac ccaccgtttc gcaaagcac  gcaccctgcc gcgtgagcca      60
gctccagata gcacgctggc gctgctgcgc gagggttacg gtttcatccg taaccgttgt     120
cgccgtcacg acagcgacct gttcgcagcc cgtttgttgc tgagcccggt catctgcatg     180
tctggcgcgg aggcggcacg ccacttttac gacggtcacc gctttactcg tcgtcatgca     240
ctgccgccga ccagcttcgc tctgatccaa gaccacggta gcgttatggt tctggatggc     300
gccgcacacc tggcacgtaa ggctatgttc ctgagcctgg tcggtgaaga ggccctgcaa     360
cgtttggcgg gcctggcgga acgtcactgg gcgaagcgg  tgtccggctg ggcacgtaaa     420
gatacggtgg ttctgctgga cgaggcacat cgcgtgctga ccgcagcggt ctgcgaatgg     480
gtgggtttgc cgctgggccc gaccgaagtg gatgctcgcg cgcgtgagtt cgcagcgatg     540
attgatggca cgggtgcagt gggtccgcgc aactggcgcg gtcacttgta tcgtgcacgc     600
acggagcgtt gggttcgcaa ggttatcgac gagatccgct ccggtcgtcg cgatgtccct     660
ccgggtgccg cacgcactat cgcggagcat caagatgccg acggtcaacg tctggatcgt     720
acggtcgcgg tgttgaact  gatcaacgtt ctgcgcccga ccgttgcgaa cgcacgttac     780
attgtctttg cagctatggc gctgcacgat cacccctcatc agcgcgctgc gttggcggac     840
ggtggtgaag ctgcggaacg ctttaccgat gaagtgcgtc gcttctaccc attcatcccg     900
tttatcggcg gtcgtgtccg tgcgccgttc cattttggtg ccacgacttt cgcgaaggt      960
gaatgggtgc tgatggatct gtatggtacc aatcgtgacc cacgtctgtg gcacgagcca    1020
gaacgtttcg acccggatcg ttttgctcgt gaaaccatcg atccgtttaa tatggtttct    1080
catggtgcgg gtagcgctcg cgatggtcac gctgtccgg  gtgagggtat acccgcatc     1140
ctgttgcgta cgctgagccg ccaactggcc gcgacgcgct acacggttcc gccacaagac    1200
ctgaccctgg acctggcgca tgtgcctgcc cgtccgcgca gcggttttgt tatgcgtgct    1260
gtgcacgcgc cgtaa                                                     1275

<210> SEQ ID NO 12
<211> LENGTH: 424
<212> TYPE: PRT
<213> ORGANISM: Methylobacterium populi
```

<400> SEQUENCE: 12

Met Pro Ala Ala Ile Ala Thr His Arg Phe Arg Lys Ala Arg Thr Leu
1               5                   10                  15

Pro Arg Glu Pro Ala Pro Asp Ser Thr Leu Ala Leu Leu Arg Glu Gly
            20                  25                  30

Tyr Gly Phe Ile Arg Asn Arg Cys Arg Arg His Asp Ser Asp Leu Phe
                35                  40                  45

Ala Ala Arg Leu Leu Leu Ser Pro Val Ile Cys Met Ser Gly Ala Glu
        50                  55                  60

Ala Ala Arg His Phe Tyr Asp Gly His Arg Phe Thr Arg His Arg Ala
65                  70                  75                  80

Leu Pro Pro Thr Ser Phe Ala Leu Ile Gln Asp His Gly Ser Val Met
                85                  90                  95

Val Leu Asp Gly Ala Ala His Leu Ala Arg Lys Ala Met Phe Leu Ser
            100                 105                 110

Leu Val Gly Glu Glu Ala Leu Gln Arg Leu Ala Gly Leu Ala Glu Arg
                115                 120                 125

His Trp Arg Glu Ala Val Ser Gly Trp Ala Arg Lys Asp Thr Val Val
        130                 135                 140

Leu Leu Asp Glu Ala His Arg Val Leu Thr Ala Ala Val Cys Glu Trp
145                 150                 155                 160

Val Gly Leu Pro Leu Gly Pro Thr Glu Val Asp Ala Arg Ala Arg Glu
                165                 170                 175

Phe Ala Ala Met Ile Asp Gly Thr Gly Ala Val Gly Pro Arg Asn Trp
            180                 185                 190

Arg Gly His Leu Tyr Arg Ala Arg Thr Glu Arg Trp Val Arg Lys Val
        195                 200                 205

Ile Asp Glu Ile Arg Ser Gly Arg Arg Asp Val Pro Pro Gly Ala Ala
    210                 215                 220

Arg Thr Ile Ala Glu His Gln Asp Ala Asp Gly Gln Arg Leu Asp Arg
225                 230                 235                 240

Thr Val Ala Gly Val Glu Leu Ile Asn Val Leu Arg Pro Thr Val Ala
                245                 250                 255

Asn Ala Arg Tyr Ile Val Phe Ala Ala Met Ala Leu His Asp His Pro
            260                 265                 270

His Gln Arg Ala Ala Leu Ala Asp Gly Gly Glu Ala Ala Glu Arg Phe
        275                 280                 285

Thr Asp Glu Val Arg Arg Phe Tyr Pro Phe Ile Pro Phe Ile Gly Gly
    290                 295                 300

Arg Val Arg Ala Pro Phe His Phe Gly Gly His Asp Phe Arg Glu Gly
305                 310                 315                 320

Glu Trp Val Leu Met Asp Leu Tyr Gly Thr Asn Arg Asp Pro Arg Leu
                325                 330                 335

Trp His Glu Pro Glu Arg Phe Asp Pro Asp Arg Phe Ala Arg Glu Thr
            340                 345                 350

Ile Asp Pro Phe Asn Met Val Ser His Gly Ala Gly Ser Ala Arg Asp
        355                 360                 365

Gly His Arg Cys Pro Gly Glu Gly Ile Thr Arg Ile Leu Leu Arg Thr
    370                 375                 380

Leu Ser Arg Gln Leu Ala Ala Thr Arg Tyr Thr Val Pro Pro Gln Asp
385                 390                 395                 400

Leu Thr Leu Asp Leu Ala His Val Pro Ala Arg Pro Arg Ser Gly Phe
                405                 410                 415

Val Met Arg Ala Val His Ala Pro
            420

<210> SEQ ID NO 13
<211> LENGTH: 1254
<212> TYPE: DNA
<213> ORGANISM: Bacillus subtilis

<400> SEQUENCE: 13

```
atgaatgagc agattccaca tgacaaaagt ctcgataaca gtctgacact gctgaaggaa      60
gggtatttat ttattaaaaa cagaacagag cgctacaatt cagatctgtt tcaggcccgt     120
ttgttgggaa aaaactttat ttgcatgact ggcgctgagg cggcgaaggt gttttatgat     180
acggatcgat tccagcggca gaacgctttg cctaagcggg tgcagaaatc gctgtttggt     240
gttaatgcga ttcagggaat ggatggcagc gcgcatatcc atcggaagat gcttttttctg    300
tcattgatga caccgccgca tcaaaaacgt ttggctgagt tgatgacaga ggagtggaaa     360
gcagcagtca agatgggaa gaaggcagat gaggttgtgt atttgaaga agcaaaagaa       420
atcctgtgcc gggtagcgtg ctattgggca ggtgttccgt tgaaggaaac ggaagtcaaa     480
gagagagcgg atgacttcat tgacatggtc gacgcgttcg gtgctgtggg accgcggcat     540
tggaaaggaa gaagagcaag gccgcgtgcg gaagagtgga ttgaagtcat gattgaagat     600
gctcgtgccg gcttgctgaa aacgacttcc ggaacagcgc tgcatgaaat ggcttttcac     660
acacaagaag atggaagcca gctggattcc cgcatggcag ccattgagct gattaatgta     720
ctgcggccta ttgtcgccat ttcttacttt ctggtgtttt cagctttggc gcttcatgag     780
catccgaagt ataaggaatg gctgcggtct ggaaacagcc gggaaagaga aatgtttgtg     840
caggaggtcc gcagatatta tccgttcggc ccgttttttag gggcgcttgt caaaaaagat    900
tttgtatgga ataactgtga gtttaagaag gcacatcgg tgctgcttga tttatatgga     960
acgaaccacg accctcgtct atgggatcat cccgatgaat tccggccgga cgatttgcg    1020
gagcgggaag aaaatctgtt tgatatgatt cctcaaggcg gggggcacgc cgagaaaggc   1080
caccgctgtc caggggaagg cattacaatt gaagtcatga agcgagcct ggatttcctc    1140
gtccatcaga ttgaatacga tgttccggaa caatcactgc attacagtct cgccagaatg   1200
ccatcattgc ctgaaagcgg cttcgtaatg agcggaatca gacgaaaaag ttaa          1254
```

<210> SEQ ID NO 14
<211> LENGTH: 417
<212> TYPE: PRT
<213> ORGANISM: Bacillus subtilis

<400> SEQUENCE: 14

Met Asn Glu Gln Ile Pro His Asp Lys Ser Leu Asp Asn Ser Leu Thr
1               5                   10                  15

Leu Leu Lys Glu Gly Tyr Leu Phe Ile Lys Asn Arg Thr Glu Arg Tyr
            20                  25                  30

Asn Ser Asp Leu Phe Gln Ala Arg Leu Leu Gly Lys Asn Phe Ile Cys
        35                  40                  45

Met Thr Gly Ala Glu Ala Ala Lys Val Phe Tyr Asp Thr Asp Arg Phe
    50                  55                  60

Gln Arg Gln Asn Ala Leu Pro Lys Arg Val Gln Lys Ser Leu Phe Gly
65                  70                  75                  80

Val Asn Ala Ile Gln Gly Met Asp Gly Ser Ala His Ile His Arg Lys
                85                  90                  95

-continued

```
Met Leu Phe Leu Ser Leu Met Thr Pro Pro His Gln Lys Arg Leu Ala
            100                 105                 110
Glu Leu Met Thr Glu Glu Trp Lys Ala Ala Val Thr Arg Trp Glu Lys
            115                 120                 125
Ala Asp Glu Val Val Leu Phe Glu Glu Ala Lys Glu Ile Leu Cys Arg
130                 135                 140
Val Ala Cys Tyr Trp Ala Gly Val Pro Leu Lys Glu Thr Glu Val Lys
145                 150                 155                 160
Glu Arg Ala Asp Asp Phe Ile Asp Met Val Asp Ala Phe Gly Ala Val
                165                 170                 175
Gly Pro Arg His Trp Lys Gly Arg Arg Ala Arg Pro Arg Ala Glu Glu
            180                 185                 190
Trp Ile Glu Val Met Ile Glu Asp Ala Arg Ala Gly Leu Leu Lys Thr
            195                 200                 205
Thr Ser Gly Thr Ala Leu His Glu Met Ala Phe His Thr Gln Glu Asp
    210                 215                 220
Gly Ser Gln Leu Asp Ser Arg Met Ala Ala Ile Glu Leu Ile Asn Val
225                 230                 235                 240
Leu Arg Pro Ile Val Ala Ile Ser Tyr Phe Leu Val Phe Ser Ala Leu
                245                 250                 255
Ala Leu His Glu His Pro Lys Tyr Lys Glu Trp Leu Arg Ser Gly Asn
            260                 265                 270
Ser Arg Glu Arg Glu Met Phe Val Gln Glu Val Arg Arg Tyr Tyr Pro
            275                 280                 285
Phe Gly Pro Phe Leu Gly Ala Leu Val Lys Lys Asp Phe Val Trp Asn
            290                 295                 300
Asn Cys Glu Phe Lys Lys Gly Thr Ser Val Leu Leu Asp Leu Tyr Gly
305                 310                 315                 320
Thr Asn His Asp Pro Arg Leu Trp Asp His Pro Asp Glu Phe Arg Pro
                325                 330                 335
Glu Arg Phe Ala Glu Arg Glu Glu Asn Leu Phe Asp Met Ile Pro Gln
            340                 345                 350
Gly Gly Gly His Ala Glu Lys Gly His Arg Cys Pro Gly Glu Gly Ile
            355                 360                 365
Thr Ile Glu Val Met Lys Ala Ser Leu Asp Phe Leu Val His Gln Ile
    370                 375                 380
Glu Tyr Asp Val Pro Glu Gln Ser Leu His Tyr Ser Leu Ala Arg Met
385                 390                 395                 400
Pro Ser Leu Pro Glu Ser Gly Phe Val Met Ser Gly Ile Arg Arg Lys
                405                 410                 415
Ser
```

METHODS AND COMPOSITIONS FOR PRODUCING OLEFINS

CROSS-REFERENCE TO RELATED APPLICATIONS

This application is a divisional of copending U.S. patent application Ser. No. 12/673,752, filed Apr. 14, 2011, as the U.S. National phase of Patent Cooperation Treaty Application No. PCT/US08/14029, filed Dec. 22, 2008, which claims priority to U.S. Provisional Application No. 61/092,278, filed on Aug. 27, 2008; U.S. Provisional Application No. 61/051,886, filed on May 9, 2008; and U.S. Provisional Application No. 61/016,183, filed on Dec. 21, 2007, all of which are herein expressly incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 40,960 Byte ASCII (Text) file named "LS00011 PCT_ST25_Sequence Lstg_03.12.09" created on Mar. 11, 2009. It is understood that the Patent and Trademark Office will make the necessary changes in application number and filing date for the instant application.

BACKGROUND OF THE INVENTION

Petroleum is a limited, natural resource found in the Earth in liquid, gaseous, or solid forms. Petroleum is primarily composed of hydrocarbons, which are comprised mainly of carbon and hydrogen. It also contains significant amounts of other elements, such as, nitrogen, oxygen, or sulfur, in different forms.

Petroleum is a valuable resource, but petroleum products are developed at considerable costs, both financial and environmental. First, sources of petroleum must be discovered. Petroleum exploration is an expensive and risky venture. The cost of exploring deep water wells can exceed $100 million. Moreover, there is no guarantee that these wells will contain petroleum. It is estimated that only 40% of drilled wells lead to productive wells generating commercial hydrocarbons. In addition to the economic cost, petroleum exploration carries a high environmental cost. For example, offshore exploration disturbs the surrounding marine environments.

After a productive well is discovered, the petroleum must be extracted from the Earth at great expense. During primary recovery, the natural pressure underground is sufficient to extract about 20% of the petroleum in the well. As this natural pressure falls, secondary recovery methods are employed, if economical. Generally, secondary recovery involves increasing the well's pressure by, for example, water injection, natural gas injection, or gas lift. Using secondary recovery methods, an additional 5% to 15% of petroleum is recovered. Once secondary recovery methods are exhausted, tertiary recovery methods can be used, if economical. Tertiary methods involve reducing the viscosity of the petroleum to make it easier to extract. Using tertiary recovery methods, an additional 5% to 15% of petroleum is recovered. Hence, even under the best circumstances, only 50% of the petroleum in a well can be extracted. Petroleum extraction also carries an environmental cost. For example, petroleum extraction can result in large seepages of petroleum rising to the surface. Moreover, offshore drilling involves dredging the seabed which disrupts or destroys the surrounding marine environment. Since petroleum deposits are not found uniformly throughout the Earth, petroleum must be transported over great distances from petroleum producing regions to petroleum consuming regions. In addition to the shipping costs, there is also the environmental risk of devastating oil spills.

In its natural form, crude petroleum extracted from the Earth has few commercial uses. It is a mixture of hydrocarbons (e.g., paraffins (or alkanes), olefins (or alkenes), alkynes, napthenes (or cylcoalkanes), aliphatic compounds, aromatic compounds, etc.) of varying length and complexity. In addition, crude petroleum contains other organic compounds (e.g., organic compounds containing nitrogen, oxygen, sulfur, etc.) and impurities (e.g., sulfur, salt, acid, metals, etc.).

Hence, crude petroleum must be refined and purified before it can be used commercially. Due to its high energy density and its easy transportability, most petroleum is refined into fuels, such as transportation fuels (e.g., gasoline, diesel, aviation fuel, etc.), heating oil, liquefied petroleum gas, etc.

Crude petroleum is also a primary source of raw materials for producing petrochemicals. The two main classes of raw materials derived from petroleum are short chain olefins (e.g., ethylene and propylene) and aromatics (e.g., benzene and xylene isomers). These raw materials are derived from longer chain hydrocarbons in crude petroleum by cracking it at considerable expense using a variety of methods, such as catalytic cracking, steam cracking, or catalytic reforming. These raw materials are used to make petrochemicals, which cannot be directly refined from crude petroleum, such as monomers, solvents, detergents, or adhesives.

One example of a raw material derived from crude petroleum is ethylene. Ethylene is used to produce petrochemicals such as, polyethylene, ethanol, ethylene oxide, ethylene glycol, polyester, glycol ether, ethoxylate, vinyl acetate, 1,2-dichloroethane, trichloroethylene, tetrachloroethylene, vinyl chloride, and polyvinyl chloride. An additional example of a raw material is propylene, which is used to produce isopropyl alcohol, acrylonitrile, polypropylene, propylene oxide, propylene glycol, glycol ethers, butylene, isobutylene, 1,3-butadiene, synthetic elastomers, polyolefins, alpha-olefins, fatty alcohols, acrylic acid, acrylic polymers, allyl chloride, epichlorohydrin, and epoxy resins.

These petrochemicals can then be used to make specialty chemicals, such as plastics, resins, fibers, elastomers, pharmaceuticals, lubricants, or gels. Particular specialty chemicals which can be produced from petrochemical raw materials are: fatty acids, hydrocarbons (e.g., long chain, branched chain, saturated, unsaturated, etc.), fatty alcohols, esters, fatty aldehydes, ketones, lubricants, etc.

Specialty chemicals have many commercial uses. Hydrocarbons have many commercial uses. For example, shorter chain alkanes are used as fuels. Methane and ethane are the main constituents of natural gas. Longer chain alkanes (e.g., from five to sixteen carbons) are used as transportation fuels (e.g., gasoline, diesel, or aviation fuel). Alkanes having more than sixteen carbon atoms are important components of fuel oils and lubricating oils. Even longer alkanes, which are solid at room temperature, can be used, for example, as a paraffin wax. Alkanes that contain approximately thirty-five carbons are found in bitumen, which is used for road surfacing. In addition, longer chain alkanes can be cracked to produce commercially useful shorter chain hydrocarbons.

Like short chain alkanes, short chain olefins, or alkenes, are used in transportation fuels. Longer chain olefins are used in plastics, lubricants, and synthetic lubricants. In addition, olefins are used as a feedstock to produce alcohols, esters, plasticizers, surfactants, tertiary amines, enhanced oil recovery agents, fatty acids, thiols, alkenylsuccinic anhydrides, polymers, textiles, solvents, adhesives epoxides, chlorinated alkanes, chlorinated olefins, waxes, fuel additives, and drag flow reducers. In addition, long chain olefins can be cracked to produce fuels.

Olefins have traditionally been produced from petroleum sources through the process of steam or catalytic cracking. Because of the limited availability and high cost of petroleum sources, the cost of producing olefins from such petroleum sources has been steadily increasing.

Olefins are the largest volume of chemical intermediates produced in the chemical industry, with global annual production previously estimated at over 300 billion lbs per year. Olefins are produced almost exclusively from ethane or other light alkanes (naphtha) in a process called cracking. This process involves heating the ethane or other light olefins to approximately 750-1000° C. in a cracker. It has been estimated that 30% of all pollution from chemical plants comes from cracking owing to emissions and unburned hydrocarbons in the flame required to heat the cracker. Approximately 10% of petroleum is consumed in the production of olefins and related chemicals.

In addition, crude petroleum is a source of lubricants. Lubricants derived petroleum are typically composed of olefins, particularly polyolefins and terminal olefins. Lubricants can either be refined from crude petroleum or manufactured using raw materials refined from crude petroleum.

Obtaining these specialty chemicals from crude petroleum requires a significant financial investment as well as a great deal of energy. It is also an inefficient process because frequently the long chain hydrocarbons in crude petroleum are cracked to produce smaller monomers. These monomer are then used as the raw material to manufacture the more complex specialty chemicals.

In addition to the problems with exploring, extracting, transporting, and refining petroleum, petroleum is a limited and dwindling resource. One estimate of world petroleum consumption is 30 billion barrels per year. By some estimates, it is predicted that at current production levels, the world's petroleum reserves could be depleted before the year 2050.

Finally, the burning of petroleum based fuels releases greenhouse gases (e.g., carbon dioxide) and other forms of air pollution (e.g., carbon monoxide, sulfur dioxide, etc.). As the world's demand for fuel increases, the emission of greenhouse gases and other forms of air pollution also increases. The accumulation of greenhouse gases in the atmosphere leads to an increase global warming. Hence, in addition to damaging the environment locally (e.g., oil spills, dredging of marine environments, etc.), burning petroleum also damages the environment globally.

Due to the inherent challenges posed by petroleum, there is a need for a renewable petroleum source which does not need to be explored, extracted, transported over long distances, or substantially refined like petroleum. There is also a need for a renewable petroleum source which can be produced economically without creating the type of environmental damage produced by the petroleum industry and the burning of petroleum based fuels. For similar reasons, there is also a need for a renewable source of chemicals which are typically derived from petroleum.

One method of producing renewable petroleum is by engineering microorganisms to produce renewable petroleum products. Some microorganims have a natural ability to produce chemicals. For example, yeast has been used for centuries to produce ethanol (e.g., beer, wine, etc.). In recent years, through the development of advanced biotechnologies, it is possible to metabolically engineer an organism to produce biochemicals that were never previously produced. Chemicals derived from these cellular activities are known as biochemicals. Fuels produced these cellular activities are known as biofuels. Biofuels are a renewable alternative to petroleum based fuels. Biofuels can be substituted for any petroleum based fuel (e.g., gasoline, diesel, aviation fuel, heating oil, etc.). Biofuels can be derived from renewable sources, such as plant matter, animal matter, or even waste products. These renewable sources are collectively known as biomass. One advantage of biofuels over petroleum based fuels is that they do not require expensive and risky exploration or extraction. In addition, biofuels can be locally produced. Hence, they do not require transportation over long distances. Moreover, biofuels can be made directly without the need for expensive and energy intensive refining as is needed with refining crude petroleum. In other circumstances, the biofuel may require a limited and cost-effective level of refining. Furthermore, the use of biofuels improves the environment by reducing the amount of environmentally harmful emissions (e.g., green house gases, air pollution, etc.) released during combustion. Finally, biofuels maintain a balanced carbon cycle because biofuels are produced from biomass, a renewable, natural resource. While the burning of biofuels will release carbon (e.g., as carbon dioxide), this carbon will be recycled during the production of biomass (e.g., the cultivation of crops) thereby balancing the carbon cycle unlike petroleum based fuels.

For similar reasons, biologically derived chemicals offer the same advantages as biofuels over petroleum based fuels. Biologically derived chemicals are a renewable alternative to petrochemicals. Biologically derived chemicals, such as hydrocarbons (e.g., alkanes, alkenes, or alkynes), fatty alcohols, esters, fatty acids, fatty aldehydes, and ketones are superior to petrochemicals because they are produced directly without extensive refining. Unlike petrochemicals, biologically derived chemicals do not need to be refined like crude petroleum to recover raw materials which must then be further processed to make more complex petrochemicals. Biologically derived chemicals are directly converted from biomass to the desired chemical product.

To reduce our reliance on petroleum based fuels, it would be desirable to produce olefins from other sources.

SUMMARY OF THE INVENTION

The invention is based, at least in part, on the discovery of a novel gene, orf880, which encodes an olefin-producing enzyme. Accordingly, in one aspect, the invention features an isolated polynucleotide comprising a nucleotide sequence having at least 70% sequence identity to SEQ ID NO:1, 4, 6, 8, 9, 11, or 13. In some embodiments, the nucleotide sequence has at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1, 4, 6, 8, 9, 11, or 13. In some embodiments, the polynucleotide comprises the nucleotide sequence of SEQ ID NO:1, 4, 6, 8, 9, 11, or 13. In other embodiments, the polynucleotide consists of the nucleotide sequence of SEQ ID NO:1, 4, 6, 8, 9, 11, or 13.

In another aspect, the invention features an isolated polynucleotide comprising a nucleotide sequence that hybridizes to a complement of SEQ ID NO:1, 4, 6, 8, 9, 11, or 13 or to a fragment thereof. In some embodiments, the nucleotide sequence hybridizes to a complement of SEQ ID NO:1, 4, 6, 8, 9, 11, or 13 or to a fragment thereof under low stringency, medium stringency, high stringency, or very high stringency conditions.

In another aspect, the invention features an isolated polynucleotide comprising a sequence encoding a polypeptide comprising (i) the amino acid sequence of SEQ ID NO:2, 5, 7, 10, 12, or 14 or (ii) the amino acid sequence of SEQ ID NO:2, 5, 7, 10, 12, or 14 with one or more amino acid substitutions, additions, insertions, or deletions. In some embodiments, the polypeptide comprises the amino acid sequence of SEQ ID NO:2, 5, 7, 10, 12, or 14 with one or more conservative amino acid substitutions. For example, the polypeptide comprises one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the polypeptide has about 1, 2, 3, 4, 5, 6, 7, 8, 9, 10, 15, 20, 30, 40, 50, 60, 70, 80, 90, 100 or more amino acid substitutions, additions, insertions, or deletions.

In some embodiments, the polypeptide has fatty acid decarboxylase activity.

In another aspect, the invention features an isolated polynucleotide comprising a nucleotide sequence encoding a polypeptide having the same biological activity as a polypeptide comprising the amino acid sequence of SEQ ID NO:2, 5, 7, 10, 12, or 14, wherein the polynucleotide comprises: (i) the nucleotide sequence of SEQ ID NO:1, 4, 6, 8, 9, 11, or 13 or a fragment thereof, or (ii) a nucleotide sequence that hybridizes to a complement of SEQ ID NO:1, 4, 6, 8, 9, 11, or 13 or to a fragment thereof. In some embodiments, the biological activity is fatty acid decarboxylase activity. In some embodiments, the nucleotide sequence hybridizes to a complement of SEQ ID NO:1, 4, 6, 8, 9, 11, or 13 or to a fragment thereof under low stringency, medium stringency, high stringency, or very high stringency conditions.

In some embodiments, the polynucleotide comprises a sequence encoding a polypeptide comprising the amino acid sequence of SEQ ID NO:2, 5, 7, 10, 12, or 14.

In other embodiments, a polynucleotide described herein is isolated from a bacterium, plant, insect, yeast, fungus, or mammal. In some embodiments, the polynucleotide is isolated from a bacterium, for example, a Gram positive or Gram negative bacterium. In specific embodiments, the bacterium is a member of the genus *Jeotgalicoccus, Corynebacterium, Kokuria, Methylobacterium*, or *Bacillus*. For example, the bacterium is selected from the group consisting of *Jeotgalicoccus halotolerans, Jeotgalicoccus psychrophilus, Jeotgalicoccus* sp. ATCC 8456, *Jeotgalicoccus pinnipedalis, Corynebacterium efficiens, Kokuria rhizophila, Methylobacterium populi*, and *Bacillus subtilis*.

In other embodiments, the isolated polynucleotide includes an operably linked promoter.

In another aspect, the invention features an isolated polypeptide that includes the amino acid sequence of SEQ ID NO:2, 5, 7, 10, 12, or 14, or a biologically active fragment thereof. In some embodiments, the polypeptide consists of the amino acid sequence of SEQ ID NO:2, 5, 7, 10, 12, or 14 or a biologically active fragment thereof. In some embodiments, the fragment is at least about 25 amino acids in length, for example, at least about 30, at least about 40, at least about 50, at least about 75, at least about 100, at least about 150, at least about 200, or at least about 250 amino acids in length. In certain embodiments, the fragment has fatty acid decarboxylase activity.

In yet another aspect, the invention features an isolated polypeptide that includes the amino acid sequence of SEQ ID NO:2, 5, 7, 10, 12, or 14 with one or more amino acid substitutions, additions, insertions, or deletions. In some embodiments, the polypeptide includes the amino acid sequence of SEQ ID NO:2, 5, 7, 10, 12, or 14 with one or more conservative amino acid substitutions. For example, the polypeptide includes one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

In some embodiments, the polypeptide has about 1, 2, 3, 4, 5, 6, 7, 8, 9, 10, 15, 20, 30, 40, 50, 60, 70, 80, 90, 100 or more amino acid substitutions, additions, insertions, or deletions. In some embodiments, the isolated polypeptide has fatty acid decarboxylase activity.

In another aspect, the invention features an isolated polypeptide that includes the amino acid sequence F-X-X-E-[VI]-[RK]-R-X-Y-P-F-{F}-P-X-[LIV], where X is any amino acid and {F} stands for any amino acid except Phe; and wherein the polypeptide has fatty acid decarboxylase activity. In an alternate embodiment, the invention features an isolated polypeptide that includes the amino acid sequence P-X(6)-[LI]-X(4)-{G}-[VI]-[HQM]-X-[MLV]-D-G-X(2)-H-X(2)-R-K, where X is any amino acid and {G} stands for any amino acid except Gly; and wherein the polypeptide has fatty acid decarboxylase activity. In another embodiment, the invention features an isolated polypeptide that includes the amino acid sequence [AC]-[AG]-[IV]-[DE]-[IL]-X-N-X(2)-R-P-X-[VI]-A-X(3)-[FY]-X(2)-F-X(3)-A-[LMV]-X-[DE] where X is any amino acid; and wherein the polypeptide has fatty acid decarboxylase activity. In another embodiment, the invention features an isolated polypeptide that includes the amino acid sequence {RK}-X(6)-[LMV]-X(4)-[AC]-[AG]-[IV]-[DE]-[IL]-X-N-X(2)-R-P-X-[VI]-A-X(3)-[FY]-X(2)-F-X(3)-A-[LMV]-X-[DE] where X is any amino acid and {RK} stands for any amino acid except Arg and Lys; and wherein the polypeptide has fatty acid decarboxylase activity.

In another aspect, the invention features a recombinant vector that includes a polynucleotide described herein. In some embodiments, the vector is a plasmid. In other embodiments, the vector further includes a promoter operably linked to the polynucleotide, for example, a developmentally-regulated, an organelle-specific, a tissue-specific, an inducible, a constitutive, or a cell-specific promoter.

In some embodiments, the vector includes at least one sequence selected from the group consisting of: (a) a regulatory sequence operatively coupled to the polynucleotide; (b) a selection marker operatively coupled to the polynucleotide; (c) a marker sequence operatively coupled to the polynucleotide; (d) a purification moiety operatively coupled to the polynucleotide; (e) a secretion sequence operatively coupled to the polynucleotide; and (f) a targeting sequence operatively coupled to the polynucleotide.

In another aspect, the invention features a host cell comprising a recombinant vector described herein, for example, a recombinant vector that includes a polynucleotide sequence described herein. In some embodiments, the host cell expresses a polypeptide encoded by the recombinant vector, for example, encoded by a polynucleotide sequence included in the recombinant vector. In some embodiments, the polynucleotide sequence is stably incorporated into the genomic DNA of the host cell. In particular embodiments, the expression of the polynucleotide sequence is under the control of a regulated promoter region.

In some embodiments, the host cell is a mammalian cell, plant cell, insect cell, yeast cell, fungus cell, a filamentous fungi cell, or bacterial cell.

In some embodiments, the host cell is a Gram positive bacterial cell. In other embodiments, the host cell is a Gram negative bacterial host cell.

In some embodiments, the host cell is from a member of the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophomonas, Schizosaccharomyces, Yarrowia,* or *Streptomyces.*

In particular embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell.

In yet other embodiments, the host cell is a *Streptomyces lividans* cell or a *Streptomyces murinus* cell. In other embodiments, the host cell is an *Actinomycetes* cell.

In some embodiments, the host cell is a CHO cell, a COS cell, a VERO cell, a BHK cell, a HeLa cell, a Cv1 cell, an MDCK cell, a 293 cell, a 3T3 cell, or a PC12 cell.

In particular embodiments, the host cell is an *E. coli* cell, such as a strain B, a strain C, a strain K, or a strain W *E. coli* cell.

In certain embodiments, the host cell produces an olefin, for example, a terminal olefin. In some embodiments, the olefin is secreted by the host cell.

In other embodiments, the host cell expresses a reduced level of an acyl-CoA synthase relative to a corresponding wild type host cell. In some embodiments, a gene encoding an acyl-CoA synthase is attenuated or deleted in the host cell. In certain embodiments, the gene is fadD, fadK, BH3103, yhfL, Pfl-4354, EAV15023, fadD1, fadD2, RPC_4074, fadDD35, fadDD22, faa1p, faa3p, lcfA, or the gene encoding the protein having the amino acid sequence Accession No. ZP_01644857. In particular embodiments, the gene is fadD.

In another aspect, the invention features a genetically engineered microorganism comprising an exogenous control sequence stably incorporated into the genomic DNA of the microorganism. In one embodiment, the control sequence is integrated upstream of a polynucleotide comprising a nucleotide sequence having at least about 70% sequence identity to SEQ ID NO:1, 4, 6, 8, 9, 11, or 13. In some embodiments, the nucleotide sequence has at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1, 4, 6, 8, 9, 11, or 13. In some embodiments, the nucleotide sequence is SEQ ID NO:1, 4, 6, 8, 9, 11, or 13.

In some embodiments, the polynucleotide is endogenous to the microorganism. In some embodiments, the microorganism expresses an increased level of a polypeptide encoded by the polynucleotide relative to a wild-type microorganism. In other embodiments, the microorganism produces an increased level of an olefin relative to a wild-type microorganism. In some embodiments, the microorganism is a bacterium, such as a *Jeotgalicoccus* bacterium.

In other embodiments, the microorganism expresses a reduced level of an acyl-CoA synthase relative to a corresponding wild type microorganism. In some embodiments, a gene encoding an acyl-CoA synthase is attenuated or deleted in the microorganism. In certain embodiments, the gene is fadD, fadK, BH3103, yhfL, Pfl-4354, EAV15023, fadD1, fadD2, RPC_4074, fadDD35, fadDD22, faa1p, faa3p, lcfA, or the gene encoding the protein having the amino acid sequence Accession No. ZP_01644857. In particular embodiments, the gene is fadD.

In another aspect, the invention features a polypeptide produced by a host cell described herein.

In yet another aspect, the invention features a method of producing an olefin. The method comprises culturing a host cell described herein, for example, a host cell comprising a nucleotide sequence described herein, under conditions sufficient to allow expression of a polypeptide encoded by the nucleotide sequence.

In some embodiments, the nucleotide sequence has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1, 4, 6, 8, 9, 11, or 13. In some embodiments, the nucleotide sequence is SEQ ID NO:1, 4, 6, 8, 9, 11, or 13.

In other embodiments, the nucleotide sequence hybridizes to a complement of SEQ ID NO:1, 4, 6, 8, 9, 11, or 13 or to a fragment thereof, for example, under low stringency, medium stringency, high stringency, or very high stringency conditions.

In other embodiments, the nucleotide sequence encodes a polypeptide comprising: (i) the amino acid sequence of SEQ ID NO:2, 5, 7, 10, 12, or 14; or (ii) the amino acid sequence of SEQ ID NO:2, 5, 7, 10, 12, or 14 with one or more amino acid substitutions, additions, insertions, or deletions. In some embodiments, the polypeptide comprises the amino acid sequence of SEQ ID NO:2, 5, 7, 10, 12, or 14 with one or more conservative amino acid substitutions. For example, the polypeptide comprises one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. In some embodiments, the polypeptide has fatty acid decarboxylase activity.

In other embodiments, the nucleotide sequence encodes a polypeptide having the same biological activity as a polypeptide comprising the amino acid sequence of SEQ ID NO:2, 5, 7, 10, 12, or 14. In some embodiments, the nucleotide sequence is SEQ ID NO:1, 4, 6, 8, 9, 11, or 13 or a fragment thereof. In other embodiments, the nucleotide sequence hybridizes to a complement of SEQ ID NO:1, 4, 6, 8, 9, 11, or 13 or to a fragment thereof, for example, under low stringency, medium stringency, high stringency, or very high stringency conditions. In some embodiments, the biological activity is fatty acid decarboxylase activity.

In some embodiments, the nucleotide sequence encodes a polypeptide comprising the amino acid sequence of SEQ ID NO:2, 5, 7, 10, 12, or 14.

In some embodiments, the host cell is selected from the group consisting of a mammalian cell, plant cell, insect cell, yeast cell, fungus cell, filamentous fungi cell, and bacterial cell.

In some embodiments, the host cell is a Gram positive bacterial cell. In other embodiments, the host cell is a Gram negative bacterial cell.

In some embodiments, the host cell is selected from the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces*, and *Stenotrophamonas*, In particular embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell.

In yet other embodiments, the host cell is a *Streptomyces lividans* cell or a *Streptomyces murinus* cell. In other embodiments, the host cell is an *Actinomycetes* cell.

In some embodiments, the host cell is a CHO cell, a COS cell, a VERO cell, a BHK cell, a HeLa cell, a Cv1 cell, an MDCK cell, a 293 cell, a 3T3 cell, or a PC12 cell.

In particular embodiments, the host cell is an *E. coli* cell, such as a strain B, a strain C, a strain K, or a strain W *E. coli* cell.

In some embodiments, the olefin is a terminal olefin. In some embodiments, the terminal olefin is a $C_3$-$C_{25}$ terminal olefin. For example, the terminal olefin is a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ terminal olefin. In some embodiments, the terminal olefin is nonadecene, methylnonadecene, heptadecene, methylheptadecene, or pentadecene.

In some embodiments, the terminal olefin is an unsaturated terminal olefin or a monounsaturated terminal olefin. In yet other embodiments, the terminal olefin is a straight chain terminal olefin, a branched chain terminal olefin, or a terminal olefin that includes a cyclic moiety.

In certain embodiments, the host cell overexpresses a fatty acid substrate. In some embodiments, the method further includes transforming the host cell with a nucleic acid that encodes a fatty acid enzyme (e.g., a fatty acid enzyme described herein) and the host cell overexpresses a fatty acid substrate. In other embodiments, the method further includes culturing the host cell in the presence of at least one fatty acid substrate.

In certain embodiments, the fatty acid substrate is a $C_6$-$C_{26}$ fatty acid substrate. For example, the fatty acid substrate is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty acid substrate. In particular embodiments, the fatty acid substrate is methyl eicosanoic acid, eicosanoic acid, methyl octadecanoic acid, stearic acid, or palmitic acid.

In some embodiments, the fatty acid substrate is an unsaturated fatty acid substrate, a monounsaturated fatty acid substrate, or a saturated fatty acid substrate. In other embodiments, the fatty acid substrate is a straight chain fatty acid substrate, a branched chain fatty acid substrate, or a fatty acid substrate that includes a cyclic moiety.

In other embodiments, the host cell expresses a reduced level of an acyl-CoA synthase relative to a corresponding wild type host cell. In some embodiments, a gene encoding an acyl-CoA synthase is attenuated or deleted in the host cell. In certain embodiments, the gene is fadD, fadK, BH3103, yhfL, Pfl-4354, EAV15023, fadD1, fadD2, RPC_4074, fadDD35, fadDD22, faa1p, faa3p, lcfA, or the gene encoding the protein having the amino acid sequence Accession No. ZP_01644857. In particular embodiments, the gene is fadD.

In some embodiments, the method further includes isolating the olefin from the host cell or from the culture medium. In other embodiments, the method further includes cracking or refining the olefin.

In another aspect, the invention features a method of making an olefin. The method includes contacting a biological substrate with an isolated polypeptide having the same biological activity as a polypeptide comprising the amino acid sequence of SEQ ID NO:2, 5, 7, 10, 12, or 14.

In some embodiments, the olefin is a terminal olefin. In some embodiments, the terminal olefin is a $C_3$-$C_{25}$ terminal olefin. For example, the terminal olefin is a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ terminal olefin. In some embodiments, the terminal olefin is nonadecene, methylnonadecene, heptadecene, methylheptadecene, or pentadecene.

In some embodiments, the terminal olefin is an unsaturated terminal olefin or a monounsaturated terminal olefin. In yet other embodiments, the terminal olefin is a straight chain terminal olefin, a branched chain terminal olefin, or a terminal olefin that includes a cyclic moiety.

In some embodiments, the biological substrate is a fatty acid substrate. In certain embodiments, the fatty acid substrate is a $C_6$-$C_{26}$ fatty acid substrate. For example, the fatty acid substrate is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty acid substrate. In particular embodiments, the fatty acid substrate is methyl eicosanoic acid, eicosanoic acid, methyl octadecanoic acid, stearic acid, or palmitic acid.

In some embodiments, the fatty acid substrate is an unsaturated fatty acid substrate, a monounsaturated fatty acid substrate, or a saturated fatty acid substrate. In other embodiments, the fatty acid substrate is a straight chain fatty acid substrate, a branched chain fatty acid substrate, or a fatty acid substrate that includes a cyclic moiety.

In another aspect, the invention features a method of making an olefin. The method includes contacting a biological substrate with an isolated polypeptide encoded by a nucleotide sequence described herein. In some embodiments, the nucleotide sequence has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1, 4, 6, 8, 9, 11, or 13. In some embodiments, the nucleotide sequence is SEQ ID NO:1, 4, 6, 8, 9, 11, or 13.

In other embodiments, the nucleotide sequence hybridizes to a complement of SEQ ID NO:1, 4, 6, 8, 9, 11, or 13 or to a fragment thereof, for example, under low stringency, medium stringency, high stringency, or very high stringency conditions.

In some embodiments, the olefin is a terminal olefin. In some embodiments, the terminal olefin is a $C_3$-$C_{25}$ terminal olefin. For example, the terminal olefin is a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ terminal olefin. In some embodiments, the terminal olefin is nonadecene, methylnonadecene, heptadecene, methylheptadecene, or pentadecene.

In some embodiments, the terminal olefin is an unsaturated terminal olefin or a monounsaturated terminal olefin. In yet other embodiments, the terminal olefin is a straight chain terminal olefin, a branched chain terminal olefin, or a terminal olefin that includes a cyclic moiety.

In some embodiments, the biological substrate is a fatty acid substrate. In certain embodiments, the fatty acid substrate is a $C_6$-$C_{26}$ fatty acid substrate. For example, the fatty acid substrate is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty acid substrate. In particular embodiments, the fatty acid substrate is methyl eicosanoic acid, eicosanoic acid, methyl octadecanoic acid, stearic acid, or palmitic acid.

In some embodiments, the fatty acid substrate is an unsaturated fatty acid substrate, a monounsaturated fatty acid substrate, or a saturated fatty acid substrate. In other embodiments, the fatty acid substrate is a straight chain fatty acid substrate, a branched chain fatty acid substrate, or a fatty acid substrate that includes a cyclic moiety.

In another aspect, the invention features a method of making an olefin. The method includes contacting a biological substrate with an isolated polypeptide described herein. In some embodiments, the polypeptide includes the amino acid sequence of SEQ ID NO:2, 5, 7, 10, 12, or 14 or a biologically active fragment thereof. In some embodiments, the polypeptide consists of the amino acid sequence of SEQ ID NO:2, 5, 7, 10, 12, or 14 or a biologically active fragment thereof. In some embodiments, the fragment is at least about 25 amino acids in length, for example, at least about 30, at least about 40, at least about 50, at least about 75, at least about 100, at least about 150, at least about 200, or at least about 250 amino acids in length. In certain embodiments, the fragment has fatty acid decarboxylase activity.

In other embodiments, the polypeptide includes the amino acid sequence of SEQ ID NO:2, 5, 7, 10, 12, or 14 with one or more amino acid substitutions, additions, insertions, or deletions. In some embodiments, the polypeptide includes the amino acid sequence of SEQ ID NO:2, 5, 7, 10, 12, or 14 with one or more conservative amino acid substitutions. For example, the polypeptide includes one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. In some embodiments, the isolated polypeptide has fatty acid decarboxylase activity.

In other embodiments, the polypeptide includes the amino acid sequence F-X-X-E-[VI]-[RK]-R-X-Y-P-F-{F}-P-X-[LIV]; and wherein the polypeptide has fatty acid decarboxylase activity. In an alternate embodiment, the polypeptide includes the amino acid sequence P-X(6)-[LI]-X(4)-{G}-[VI]-[HQM]-X-[MLV]-D-G-X(2)-H-X(2)-R-K; and wherein the polypeptide has fatty acid decarboxylase activity. In another embodiment, the polypeptide includes the amino acid sequence [AC]-[AG]-[IV]-[DE]-[IL]-X-N-X(2)-R-P-X-[VI]-A-X(3)-[FY]-X(2)-F-X(3)-A-[LMV]-X-[DE]; and wherein the polypeptide has fatty acid decarboxylase activity. In another embodiment, the polypeptide includes the amino acid sequence {RK}-X(6)-[LMV]-X(4)-[AC]-[AG]-[IV]-[DE]-[IL]-X-N-X(2)-R-P-X-[VI]-A-X(3)-[FY]-X(2)-F-X(3)-A-[LMV]-X-[DE]; and wherein the polypeptide has fatty acid decarboxylase activity. In the sequences described herein, X is any amino acid, [AB] is A or B (e.g., [VI] is valine or isoleucine), {A} is any amino acid except A (e.g., {F} stands for any amino acid except Phe), X is any amino acid, and X(n) is X repeated n times (e.g., X(4) is X-X-X-X).

In some embodiments, the olefin is a terminal olefin. In some embodiments, the terminal olefin is a $C_3$-$C_{25}$ terminal olefin. For example, the terminal olefin is a $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ terminal olefin. In some embodiments, the terminal olefin is nonadecene, methylnonadecene, heptadecene, methylheptadecene, or pentadecene.

In some embodiments, the terminal olefin is an unsaturated terminal olefin or a monounsaturated terminal olefin. In yet other embodiments, the terminal olefin is a straight chain terminal olefin, a branched chain terminal olefin, or a terminal olefin that includes a cyclic In some embodiments, the biological substrate is a fatty acid substrate. In certain embodiments, the fatty acid substrate is a $C_6$-$C_{26}$ fatty acid substrate. For example, the fatty acid substrate is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty acid substrate. In particular embodiments, the fatty acid substrate is methyl eicosanoic acid, eicosanoic acid, methyl octadecanoic acid, stearic acid, or palmitic acid.

In some embodiments, the fatty acid substrate is an unsaturated fatty acid substrate, a monounsaturated fatty acid substrate, or a saturated fatty acid substrate. In other embodiments, the fatty acid substrate is a straight chain fatty acid substrate, a branched chain fatty acid substrate, or a fatty acid substrate that includes a cyclic moiety.

In another aspect, the invention features an olefin produced by any of the methods described herein. In particular embodiments, the olefin has a $\delta^{13}C$ of about −15.4 or greater. For example, the olefin has a $\delta^{13}C$ of about −15.4 to about −10.9, for example, about −13.92 to about −13.84. In other embodiments, the olefin has an $f_M{}^{14}C$ of at least about 1.003. For example, the olefin has an $f_M{}^{14}C$ of at least about 1.01 or at least about 1.5. In some embodiments, the olefin has an $f_M{}^{14}C$ of about 1.111 to about 1.124.

In another aspect, the invention features a biofuel that includes an olefin produced by any of the methods described herein. In particular embodiments, the olefin has a $\delta^{13}C$ of about −15.4 or greater. For example, the olefin has a $\delta^{13}C$ of about −15.4 to about −10.9, for example, about −13.92 to about −13.84. In other embodiments, the olefin has an $f_M{}^{14}C$ of at least about 1.003. For example, the olefin has an $f_M{}^{14}C$ of at least about 1.01 or at least about 1.5. In some embodiments, the olefin has an $f_M{}^{14}C$ of about 1.111 to about 1.124. In some embodiments, the biofuel is a biodiesel, gasoline, or jet fuel.

DEFINITIONS

Throughout the specification, a reference may be made using an abbreviated gene name or polypeptide name, but it is understood that such an abbreviated gene or polypeptide name represents the genus of genes or polypeptides. Such gene names include all genes encoding the same polypeptide and homologous polypeptides having the same physiological function. Polypeptide names include all polypeptides that have the same activity (e.g., that catalyze the same fundamental chemical reaction).

The accession numbers referenced herein are derived from the NCBI database (National Center for Biotechnology Information) maintained by the National Institute of Health, U.S.A. The accession numbers are as provided in the database as of Aug. 28, 2008.

EC numbers are established by the Nomenclature Committee of the International Union of Biochemistry and Molecular Biology (NC-IUBMB). The EC numbers referenced herein are derived from the KEGG Ligand database, maintained by the Kyoto Encyclopedia of Genes and Genomics, sponsored in part by the University of Tokyo. The EC numbers are as provided in the database as of March, 2008.

The articles "a" and "an" are used herein to refer to one or to more than one (i.e., to at least one) of the grammatical object of the article. By way of example, "an element" means one element or more than one element.

The term "about" is used herein to mean a value±20% of a given numerical value. Thus, "about 60%" means a value of between 60±(20% of 60) (i.e., between 48 and 70).

As used herein, the term "attenuate" means to weaken, reduce or diminish. For example, a polypeptide can be attenuated by modifying the polypeptide to reduce its activity (e.g., by modifying a nucleotide sequence that encodes the polypeptide).

As used herein, the term "biodiesel" means a biofuel that can be a substitute of diesel, which is derived from petroleum. Biodiesel can be used in internal combustion diesel engines in either a pure form, which is referred to as "neat" biodiesel, or as a mixture in any concentration with petroleum-based diesel. Biodiesel can include esters or hydrocarbons, such as olefins (e.g., terminal olefins).

As used therein, the term "biofuel" refers to any fuel derived from biomass. Biofuels can be substituted for petroleum based fuels. For example, biofuels are inclusive of transportation fuels (e.g., gasoline, diesel, jet fuel, etc.), heating fuels, and electricity-generating fuels. Biofuels are a renewable energy source.

As used herein, the term "biomass" refers to a carbon source derived from biological material. Biomass can be converted into a biofuel. One exemplary source of biomass is plant matter. For example, corn, sugar cane, or switchgrass can be used as biomass. Another non-limiting example of biomass is animal matter, for example cow manure. Biomass also includes waste products from industry, agriculture, forestry, and households. Examples of such waste products that can be used as biomass are fermentation waste, straw, lumber, sewage, garbage, and food leftovers. Biomass also includes sources of carbon, such as carbohydrates (e.g., monosaccharides, disaccharides, or polysaccharides).

As used herein, the phrase "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). These include, for example, various monosaccharides, such as glucose, fructose, mannose, and galactose; oligosaccharides, such as fructo-oligosaccharide and galacto-oligosaccharide; polysaccharides such as xylose and arabinose; disaccharides, such as sucrose, maltose, and turanose; cellulosic material, such as methyl cellulose and sodium carboxymethyl cellulose; saturated or unsaturated fatty acid esters, such as succinate, lactate, and acetate; alcohols, such as ethanol or mixtures thereof. The carbon source can also be a product of photosynthesis, including, but not limited to, glucose. A preferred carbon source is biomass. Another preferred carbon source is glucose.

As used herein, a "cloud point lowering additive" is an additive added to a composition to decrease or lower the cloud point of a solution.

As used herein, the phrase "cloud point of a fluid" means the temperature at which dissolved solids are no longer completely soluble. Below this temperature, solids begin precipitating as a second phase giving the fluid a cloudy appearance. In the petroleum industry, cloud point refers to the temperature below which a solidified material or other heavy hydrocarbon crystallizes in a crude oil, refined oil, or fuel to form a cloudy appearance. The presence of solidified materials influences the flowing behavior of the fluid, the tendency of the fluid to clog fuel filters, injectors, etc., the accumulation of solidified materials on cold surfaces (e.g., a pipeline or heat exchanger fouling), and the emulsion characteristics of the fluid with water.

A nucleotide sequence is "complementary" to another nucleotide sequence if each of the bases of the two sequences matches (i.e., is capable of forming Watson Crick base pairs). The term "complementary strand" is used herein interchangeably with the term "complement". The complement of a nucleic acid strand can be the complement of a coding strand or the complement of a non-coding strand.

As used herein, the term "conditions sufficient to allow expression" means any conditions that allow a host cell to produce a desired product, such as a polypeptide or olefin described herein. Suitable conditions include, for example, fermentation conditions. Fermentation conditions can comprise many parameters, such as temperature ranges, levels of aeration, and media composition. Each of these conditions, individually and in combination, allows the host cell to grow. Exemplary culture media include broths or gels. Generally, the medium includes a carbon source, such as glucose, fructose, cellulose, or the like, that can be metabolized by a host cell directly. In addition, enzymes can be used in the medium to facilitate the mobilization (e.g., the depolymerization of starch or cellulose to fermentable sugars) and subsequent metabolism of the carbon source.

To determine if conditions are sufficient to allow expression, a host cell can be cultured, for example, for about 4, 8, 12, 24, 36, or 48 hours. During and/or after culturing, samples can be obtained and analyzed to determine if the conditions allow expression. For example, the host cells in the sample or the medium in which the host cells were grown can be tested for the presence of a desired product. When testing for the presence of a product, assays, such as, but not limited to, TLC, HPLC, GC/FID, GC/MS, LC/MS, MS, can be used.

It is understood that the polypeptides described herein may have additional conservative or non-essential amino acid substitutions, which do not have a substantial effect on the polypeptide functions. Whether or not a particular substitution will be tolerated (i.e., will not adversely affect desired biological properties, such as decarboxylase activity) can be determined as described in Bowie et al., *Science* (1990) 247: 1306-1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

As used herein, "control element" means a transcriptional control element. Control elements include promoters and enhancers. The term "promoter element," "promoter," or "promoter sequence" refers to a DNA sequence that functions as a switch that activates the expression of a gene. If the gene is activated, it is said to be transcribed or participating in transcription. Transcription involves the synthesis of mRNA from the gene. A promoter, therefore, serves as a transcriptional regulatory element and also provides a site for initiation of transcription of the gene into mRNA. Control elements interact specifically with cellular proteins involved in transcription (Maniatis et al., *Science* 236:1237, 1987).

As used herein, the term "fatty acid" means a carboxylic acid having the formula RCOOH. R represents an aliphatic group, preferably an alkyl group. R can comprise between about 4 and about 22 carbon atoms. Fatty acids can be saturated, monounsaturated, or polyunsaturated. In a preferred embodiment, the fatty acid is made from a fatty acid biosynthetic pathway.

As used herein, the term "fatty acid biosynthetic pathway" means a biosynthetic pathway that produces fatty acids. The fatty acid biosynthetic pathway includes fatty acid enzymes that can be engineered, as described herein, to produce fatty acids, and in some embodiments can be expressed with additional enzymes to produce fatty acids having desired carbon chain characteristics.

As used herein, "fatty acid enzyme" means any enzyme involved in fatty acid biosynthesis. Fatty acid enzymes can be expressed or overexpressed in host cells to produce fatty acids. Non-limiting examples of fatty acid enzymes include fatty acid synthases and thioesterases.

As used herein, "fraction of modern carbon" or "$f_M$" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence that is aligned for comparison purposes is at least about 30%, preferably at least about 40%, more preferably at least about 50%, even more preferably at least about 60%, and even more preferably at least about 70%, at least about 80%, at least about 90%, or about 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), *J. Mol. Biol.* 48:444-453, algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5.

As used herein, a "host cell" is a cell used to produce a product described herein (e.g., an olefin described herein). A host cell can be modified to express or overexpress selected genes or to have attenuated expression of selected genes. Non-limiting examples of host cells include plant, animal, human, bacteria, yeast, or filamentous fungi cells.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either method can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions unless otherwise specified.

The term "isolated" as used herein with respect to nucleic acids, such as DNA or RNA, refers to molecules separated from other DNAs or RNAs, respectively, that are present in the natural source of the nucleic acid. Moreover, by an "isolated nucleic acid" is meant to include nucleic acid fragments, which are not naturally occurring as fragments and would not be found in the natural state. The term "isolated" is also used herein to refer to polypeptides, which are isolated from other cellular proteins and is meant to encompass both purified and recombinant polypeptides. The term "isolated" as used herein also refers to a nucleic acid or peptide that is substantially free of cellular material, viral material, or culture medium when produced by recombinant DNA techniques. The term "isolated" as used herein also refers to a nucleic acid or peptide that is substantially free of chemical precursors or other chemicals when chemically synthesized.

As used herein, the "level of expression of a gene in a cell" refers to the level of mRNA, pre-mRNA nascent transcript(s), transcript processing intermediates, mature mRNA(s), and degradation products encoded by the gene in the cell.

As used herein, the term "microorganism" means prokaryotic and eukaryotic microbial species from the domains Archaea, Bacteria and Eucarya, the latter including yeast and filamentous fungi, protozoa, algae, or higher Protista. The terms "microbial cells" (i.e., cells from microbes) and "microbes" are used interchangeably and refer to cells or small organisms that can only be seen with the aid of a microscope.

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides, ESTs, chromosomes, cDNAs, mRNAs, and rRNAs.

"Olefin" and "alkene" are used interchangeably herein, and "terminal olefin," "α-olefin," and "terminal alkene" are used interchangeably herein.

As used herein, the term "operably linked" means that selected nucleotide sequence (e.g., encoding a polypeptide described herein) is in proximity with a promoter to allow the promoter to regulate expression of the selected DNA. In addition, the promoter is located upstream of the selected nucleotide sequence in terms of the direction of transcription and translation. By "operably linked" is meant that a nucleotide sequence and a regulatory sequence(s) are connected in such a way as to permit gene expression when the appropriate molecules (e.g., transcriptional activator proteins) are bound to the regulatory sequence(s).

The term "or" is used herein to mean, and is used interchangeably with, the term "and/or," unless context clearly indicates otherwise.

As used herein, "overexpress" means to express or cause to be expressed a nucleic acid, polypeptide, or hydrocarbon in a cell at a greater concentration than is normally expressed in a corresponding wild-type cell. For example, a polypeptide can be "overexpressed" in a recombinant host cell when the polypeptide is present in a greater concentration in the recombinant host cell compared to its concentration in a non-recombinant host cell of the same species.

As used herein, "partition coefficient" or "P," is defined as the equilibrium concentration of a compound in an organic phase divided by the concentration at equilibrium in an aqueous phase (e.g., fermentation broth). In one embodiment of a bi-phasic system described herein, the organic phase is formed by the olefin during the production process. However, in some examples, an organic phase can be provided, such as by providing a layer of octane, to facilitate product separation. When describing a two phase system, the partition characteristics of a compound can be described as log P. For example, a compound with a log P of 1 would partition 10:1 to the organic phase. A compound with a log P of −1 would partition 1:10 to the organic phase. By choosing an appropriate fermentation broth and organic phase, an olefin with a high log P value can separate into the organic phase even at very low concentrations in the fermentation vessel.

As used herein, the term "purify," "purified," or "purification" means the removal or isolation of a molecule from its environment by, for example, isolation or separation. "Substantially purified" molecules are at least about 60% free, preferably at least about 75% free, and more preferably at least about 90% free from other components with which they are associated. As used herein, these terms also refer to the removal of contaminants from a sample. For example, the removal of contaminants can result in an increase in the percentage of olefins in a sample. For example, when olefins are produced in a host cell, the olefins can be purified by the removal of host cell proteins. After purification, the percentage of olefins in the sample is increased.

The terms "purify," "purified," and "purification" do not require absolute purity. They are relative terms. Thus, for example, when olefins are produced in host cells, a purified olefin is one that is substantially separated from other cellular components (e.g., nucleic acids, polypeptides, lipids, carbohydrates, or other hydrocarbons). In another example, a purified olefin preparation is one in which the olefin is substantially free from contaminants, such as those that might be present following fermentation. In some embodiments, an olefin is purified when at least about 50% by weight of a sample is composed of the olefin. In other embodiments, an olefin is purified when at least about 60%, 70%, 80%, 85%, 90%, 92%, 95%, 98%, or 99% or more by weight of a sample is composed of the olefin.

As used herein, the term "recombinant polypeptide" refers to a polypeptide that is produced by recombinant DNA techniques, wherein generally DNA encoding the expressed protein or RNA is inserted into a suitable expression vector and that is in turn used to transform a host cell to produce the polypeptide or RNA.

As used herein, the term "substantially identical" (or "substantially homologous") is used to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities.

As used herein, the term "transfection" means the introduction of a nucleic acid (e.g., via an expression vector) into a recipient cell by nucleic acid-mediated gene transfer.

As used herein, "transformation" refers to a process in which a cell's genotype is changed as a result of the cellular uptake of exogenous DNA or RNA. This may result in the transformed cell expressing a recombinant form of an RNA or polypeptide. In the case of antisense expression from the transferred gene, the expression of a naturally-occurring form of the polypeptide is disrupted.

As used herein, a "transport protein" is a polypeptide that facilitates the movement of one or more compounds in and/or out of a cellular organelle and/or a cell.

As used herein, a "variant" of polypeptide X refers to a polypeptide having the amino acid sequence of peptide X in which one or more amino acid residues is altered. The variant may have conservative changes or nonconservative changes. Guidance in determining which amino acid residues may be substituted, inserted, or deleted without affecting biological activity may be found using computer programs well known in the art, for example, LASERGENE software (DNASTAR).

The term "variant," when used in the context of a polynucleotide sequence, may encompass a polynucleotide sequence related to that of a gene or the coding sequence thereof. This definition may also include, for example, "allelic," "splice," "species," or "polymorphic" variants. A splice variant may have significant identity to a reference polynucleotide, but will generally have a greater or lesser number of polynucleotides due to alternative splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species.

As used herein, the term "vector" refers to a nucleic acid molecule capable of transporting another nucleic acid to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids," which refer generally to circular double stranded DNA loops that, in their vector form, are not bound to the chromosome. In the present specification, "plasmid" and "vector" are used interchangeably, as the plasmid is the most commonly used form of vector. However, also included are such other forms of expression vectors that serve equivalent functions and that become known in the art subsequently hereto.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

BRIEF DESCRIPTION OF THE DRAWINGS

FIGS. 1A, 1B, 1C and 1D are GC/MS traces of olefins produced by *Jeotgalicoccus* sp. ATCC 8456 cells, *Jeotgalicoccus halotolerans* DSMZ 17274 cells, *Jeotgalicoccus pinnipedalis* DSMZ 17030 cells, and *Jeotgalicoccus psychrophilus* DSMZ 19085 cells, respectively.

FIGS. 7A, 7B, and 7D-7N are orf880 and orf880 homolog nucleotide and amino acid sequences.

FIG. 7C is the partial 16s rRNA sequence of *Jeotgalicoccus* sp. ATCC8456.

FIG. 10 is a table identifying various genes that can be expressed, overexpressed or attenuated to increase production of particular fatty acid substrates.

FIGS. 17A, 17B, and 17C are GC/MS traces of α-olefins produced in vitro by purified *Kokuria rhizophila* orf_KRH21570 with hexadecanoic acid as substrate (FIG. 17A), by purified *Kokuria rhizophila* orf_KRH21579 with no substrate (FIG. 17B), and with no enzyme (FIG. 17C).

FIG. 22 is a table identifying various P450 peroxygenases that can be expressed or overexpressed to produce α-olefins.

DETAILED DESCRIPTION

Figure 1A:
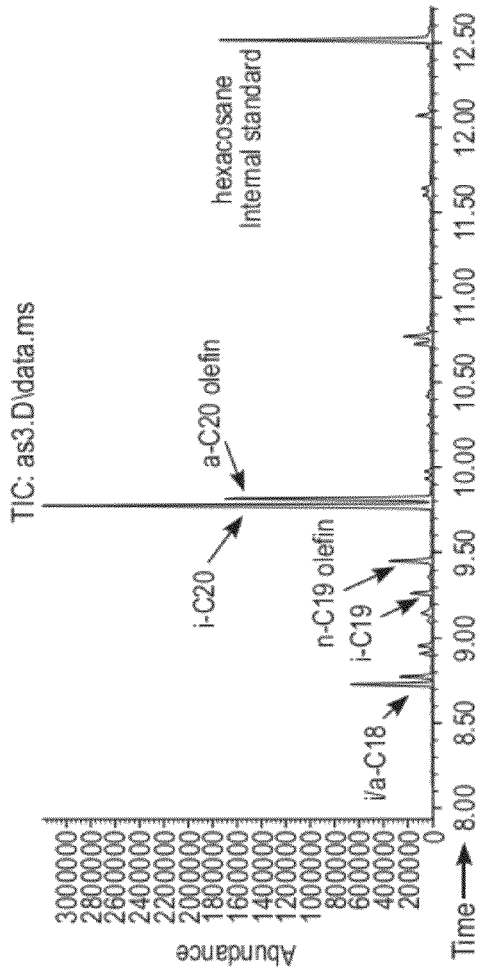

The invention provides compositions and methods of producing olefins from fatty acid substrates, in particular, terminal olefins. Such olefins are useful as a biofuel (e.g., substitutes for gasoline, diesel, jet fuel, etc.), specialty chemicals (e.g., lubricants, fuel additive, etc.), or feedstock for further chemical conversion (e.g., fuels, polymers, plastics, textiles, solvents, adhesives, etc.). The invention is based on the discovery of a novel gene, orf880, which encodes an olefin-producing enzyme. The polynucleotide sequence of orf880 and homologs of orf880 are presented as SEQ ID NO:1, 4, 6, 8, 9, 11, or 13 in FIG. 7, and the corresponding amino acid sequences are presented as SEQ ID NO:2, 5, 7, 10, 12, or 14 in FIG. 7. Using the methods described herein, olefins can be prepared using orf880, orf880 homologs, or variants thereof utilizing host cells or cell-free methods.

ORF880 Polynucleotide Variants

The methods and compositions described herein include the orf880 polynucleotide sequence (SEQ ID NO:1) as well as orf880 homologs depicted in FIG. 7 (SEQ ID NO: 4, 6, 8, 9, 11, or 13) and polynucleotide variants thereof. The variants can be naturally occurring or created in vitro. In particular, such variants can be created using genetic engineering techniques, such as site directed mutagenesis, random chemical mutagenesis, Exonuclease III deletion procedures, and standard cloning techniques. Alternatively, such variants, fragments, analogs, or derivatives can be created using chemical synthesis or modification procedures.

Methods of making variants are well known in the art. These include procedures in which nucleic acid sequences obtained from natural isolates are modified to generate nucleic acids that encode polypeptides having characteristics that enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants can be created using error prone PCR (see, e.g., Leung et al., *Technique* 1:11-15, 1989; and Caldwell et al., *PCR Methods Applic.* 2:28-33, 1992). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized (e.g., an orf880 polynucleotide sequence), are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized (e.g., an orf880 polynucleotide sequence), 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector and the activities of the polypeptides encoded by the mutagenized nucleic acids are evaluated.

Variants can also be created using oligonucleotide directed mutagenesis to generate site-specific mutations in any cloned DNA of interest. Oligonucleotide mutagenesis is described in, for example, Reidhaar-Olson et al., *Science* 241:53-57, 1988. Briefly, in such procedures a plurality of double stranded oligonucleotides bearing one or more mutations to be introduced into the cloned DNA are synthesized and inserted into the cloned DNA to be mutagenized (e.g., an orf880 polynucleotide sequence). Clones containing the mutagenized DNA are recovered, and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408.

Still another method of generating variants is sexual PCR mutagenesis. In sexual PCR mutagenesis, forced homologous recombination occurs between DNA molecules of different, but highly related, DNA sequence in vitro as a result of random fragmentation of the DNA molecule based on sequence homology. This is followed by fixation of the crossover by primer extension in a PCR reaction. Sexual PCR mutagenesis is described in, for example, Stemmer, PNAS, USA 91:10747-10751, 1994.

Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence (e.g., an orf880 polynucleotide sequence) in one of these strains will eventually generate random mutations within the DNA. Mutator strains suitable for use for in vivo mutagenesis are described in, for example, PCT Publication No. WO 91/16427.

Variants can also be generated using cassette mutagenesis. In cassette mutagenesis, a small region of a double stranded DNA molecule is replaced with a synthetic oligonucleotide "cassette" that differs from the native sequence. The oligonucleotide often contains a completely and/or partially randomized native sequence.

Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., *PNAS, USA* 89:7811-7815, 1992.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., *Biotech. Res.*

11:1548-1552, 1993. Random and site-directed mutagenesis are described in, for example, Arnold, *Curr. Opin. Biotech.* 4:450-455, 1993.

In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250.

Polynucleotide variants also include nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. (See, e.g., Summerton et al., *Antisense Nucleic Acid Drug Dev.* (1997) 7:187-195; and Hyrup et al., *Bioorgan. Med. Chem.* (1996) 4:5-23.) In addition, the deoxyphosphate backbone can be replaced with, for example, a phosphorothioate or phosphorodithioate backbone, a phosphoroamidite, or an alkyl phosphotriester backbone.

ORF880 Polypeptide Variants

The methods and compositions described herein also include the ORF880 amino acid sequence (SEQ ID NO:2) depicted in FIG. 7, homologs of ORF880 (SEQ ID NO:5, 7, 10, 12, or 14) depicted in FIG. 7, and variants thereof. ORF880 polypeptide variants can be variants in which one or more amino acid residues are substituted with a conserved or non-conserved amino acid residue (preferably a conserved amino acid residue). Such substituted amino acid residue may or may not be one encoded by the genetic code.

Conservative substitutions are those that substitute a given amino acid in a polypeptide by another amino acid of similar characteristics. Typical conservative substitutions are the following replacements: replacement of an aliphatic amino acid, such as alanine, valine, leucine, and isoleucine, with another aliphatic amino acid; replacement of a serine with a threonine or vice versa; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

Other polypeptide variants are those in which one or more amino acid residues include a substituent group. Still other polypeptide variants are those in which the polypeptide is associated with another compound, such as a compound to increase the half-life of the polypeptide (e.g., polyethylene glycol).

Additional polypeptide variants are those in which additional amino acids are fused to the polypeptide, such as a leader sequence, a secretory sequence, a proprotein sequence, or a sequence which facilitates purification, enrichment, or stabilization of the polypeptide.

In some instances, the polypeptide variants retain the same biological function as ORF880 (e.g., retain decarboxylase activity) and have amino acid sequences substantially identical thereto.

In other instances, the polypeptide variants have at least about 50%, at least about 55%, at least about 60%, at least about 65%, at least about 70%, at least about 75%, at least about 80%, at least about 85%, at least about 90%, at least about 95%, or more than about 95% homology to the amino acid sequence depicted in FIG. 7 (SEQ ID NO:2, 5, 7, 10, 12, or 14). In another embodiment, the polypeptide variants include a fragment comprising at least about 5, 10, 15, 20, 25, 30, 35, 40, 50, 75, 100, or 150 consecutive amino acids thereof.

The polypeptide variants or fragments thereof can be obtained by isolating nucleic acids encoding them using techniques described herein or by expressing synthetic nucleic acids encoding them. Alternatively, polypeptide variants or fragments thereof can be obtained through biochemical enrichment or purification procedures. The sequence of polypeptide variants or fragments can be determined by proteolytic digestion, gel electrophoresis, and/or microsequencing. The sequence of the polypeptide variants or fragments can then be compared to the amino acid sequence depicted in FIG. 7 (SEQ ID NO:2, 5, 7, 10, 12, or 14) using any of the programs described herein.

The polypeptide variants and fragments thereof can be assayed for olefin-producing activity using routine methods. For example, the polypeptide variants or fragment can be contacted with a substrate (e.g., a fatty acid substrate) under conditions that allow the polypeptide variant to function. A decrease in the level of the substrate or an increase in the level of an olefin can be measured to determine olefin-producing activity.

ORF880 Motifs

By using bioinformatics, amino acid motifs can be designed by identifying conserved regions of the fatty acid decarboxylase (e.g., *Jeotgalicoccus* sp. 8456 orf880). These amino acid motifs can be designed by methods well known in the art, such as bioinformatics, phylogenetic study, and/or protein alignments followed by visual inspection of the protein sequences. These amino acid motifs can then be used to identify proteins that have similar biological functions as the fatty acid decarboxylase. Several programs well known in the art can use the amino acid motifs to identify proteins that belong to the family of functional proteins.

Based on the experimental data, it was predicted that organisms that contain polypeptide sequences containing these amino acid motifs may be functional fatty acid decarboxylases (1) F-X-X-E-[VI]-[RK]-R-X-Y-P-F-{F}-P-X-[LIV];
(2) P-X(6)-[LI]-X(4)-{G}-[VI]-[HQM]-X-[MLV]-D-G-X(2)-H-X(2)-R-K;
(3) [AC]-[AG]-[IV]-[DE]-[IL]-X-N-X(2)-R-P-X-[VI]-A-X(3)-[FY]-X(2)-F-X(3)-A-[LMV]-X-[DE];
(4) {RK}-X(6)-[LMV]-X(4)-[AC]-[AG]-[IV]-[DE]-[IL]-X-N-X(2)-R-P-X-[VI]-A-X(3)-[FY]-X(2)-F-X(3)-A-[LMV]-X-[DE].

In the sequences described herein, [AB] is A or B (e.g., [VI] is valine or isoleucine), {A} is any amino acid except A (e.g., {F} stands for any amino acid except Phe), X represents any amino acid (e.g., any naturally occurring amino acid), and X(n) is X repeated n times (e.g., X(4) is X-X-X-X).

The invention is directed to an isolated nucleic acid encoding a polypeptide comprising a fatty acid decarboxylase amino acid motif sequence. For example, the isolated nucleic acid can encode a polypeptide comprising an amino acid sequence selected from the motifs described herein.

Preferably, the isolated nucleic acid encodes a polypeptide of no more than about 700, 650, 600, 550, 500, or 450 amino acid residues comprising a fatty acid decarboxylase amino acid motif sequence.

Anti-Orf880 Antibodies

The Orf880 polypeptides described herein can also be used to produce antibodies directed against Orf880 polypeptides. Such antibodies can be used, for example, to detect the expression of an Orf880 polypeptide using methods known in the art. The antibody can be, e.g., a polyclonal antibody; a monoclonal antibody or antigen binding fragment thereof; a modified antibody such as a chimeric antibody, reshaped antibody, humanized antibody, or fragment thereof (e.g., Fab', Fab, F(ab')$_2$); or a biosynthetic antibody, e.g., a single chain antibody, single domain antibody (DAB), Fv, single chain Fv (scFv), or the like.

Methods of making and using polyclonal and monoclonal antibodies are described, e.g., in Harlow et al., *Using Antibodies: A Laboratory Manual: Portable Protocol I*. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')$_2$ fragments); or biosynthetic antibodies (e.g., single chain antibodies, single domain antibodies (DABs), Fv, single chain Fv (scFv), and the like), are known in the art and can be found, e.g., in Zola, *Monoclonal Antibodies: Preparation and Use of Monoclonal Antibodies and Engineered Antibody Derivatives*, Springer Verlag (Dec. 15, 2000; 1st edition).

Fatty Acid Substrates

The compositions and methods described herein can be used to produce olefins (e.g., terminal olefins) from fatty acid substrates. While not wishing to be bound by theory, it is believed that the polypeptides described herein produce olefins from fatty acid substrates via a decarboxylation mechanism. Thus, olefins having particular branching patterns, levels of saturation, and carbon chain length can be produced from fatty acid substrates having those particular characteristics. Accordingly, each step within a fatty acid biosynthetic pathway can be modified to produce or overproduce a fatty acid substrate of interest. For example, known genes involved in the fatty acid biosynthetic pathway can be expressed, overexpressed, or attenuated in host cells to produce a desired fatty acid substrate (see, e.g., PCT/US08/058,788). Exemplary genes are provided in FIG. 10. It is recognized, however, that the carbon chain of an olefin produced using the methods described herein will have one less carbon than the fatty acid substrate from which it was produced.

Synthesis of Fatty Acid Substrates

Fatty acid synthase (FAS) is a group of polypeptides that catalyze the initiation and elongation of acyl chains (Marrakchi et al., *Biochemical Society*, 30:1050-1055, 2002). The acyl carrier protein (ACP) along with the enzymes in the FAS pathway control the length, degree of saturation, and branching of the fatty acids produced. The fatty acid biosynthetic pathway involves the precursors acetyl-CoA and malonyl-CoA. The steps in this pathway are catalyzed by enzymes of the fatty acid biosynthesis (fab) and acetyl-CoA carboxylase (acc) gene families (see, e.g., Heath et al., *Prog. Lipid Res.* 40(6):467-97 (2001)).

Host cells can be engineered to express fatty acid substrates by recombinantly expressing or overexpressing acetyl-CoA and/or malonyl-CoA synthase genes. For example, to increase acetyl-CoA production, one or more of the following genes can be expressed in a host cell: pdh, panK, aceEF (encoding the E1p dehydrogenase component and the E2p dihydrolipoamide acyltransferase component of the pyruvate and 2-oxoglutarate dehydrogenase complexes), fabH, fabD, fabG, acpP, and fabF. Exemplary GenBank accession numbers for these genes are: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179). Additionally, the expression levels of fadE, gpsA, ldhA, pflb, adhE, pta, poxB, ackA, and/or ackB can be attenuated or knocked-out in an engineered host cell by transformation with conditionally replicative or non-replicative plasmids containing null or deletion mutations of the corresponding genes or by substituting promoter or enhancer sequences. Exemplary GenBank accession numbers for these genes are: fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430). The resulting host cells will have increased acetyl-CoA production levels when grown in an appropriate environment.

Malonyl-CoA overexpression can be effected by introducing accABCD (e.g., accession number AAC73296, EC 6.4.1.2) into a host cell. Fatty acids can be further overexpressed in host cells by introducing into the host cell a DNA sequence encoding a lipase (e.g., accession numbers CAA89087, CAA98876).

In addition, inhibiting PlsB can lead to an increase in the levels of long chain acyl-ACP, which will inhibit early steps in the pathway (e.g., accABCD, fabH, and fabI). The plsB (e.g., accession number AAC77011) D311E mutation can be used to increase the amount of available acyl-CoA.

In addition, a host cell can be engineered to overexpress a sfa gene (suppressor of fabA, e.g., accession number AAN79592) to increase production of monounsaturated fatty acids (Rock et al., *J. Bacteriology* 178:5382-5387, 1996).

In some instances, host cells can be engineered to express, overexpress, or attenuate expression of a thioesterase to increase fatty acid substrate production. The chain length of a fatty acid substrate is controlled by thioesterase. In some instances, a tes or fat gene can be overexpressed. In other instances, $C_{10}$ fatty acids can be produced by attenuating thioesterase $C_{18}$ (e.g., accession numbers AAC73596 and P0ADA1), which uses $C_{18:1}$-ACP, and expressing thioesterase $C_{10}$ (e.g., accession number Q39513), which uses $C_{1-10}$-ACP. This results in a relatively homogeneous population of fatty acids that have a carbon chain length of 10. In yet other instances, $C_{14}$ fatty acids can be produced by attenuating endogenous thioesterases that produce non-$C_{14}$ fatty acids and expressing the thioesterases, that use $C_{14}$-ACP (for example, accession number Q39473). In some situations, $C_{12}$ fatty acids can be produced by expressing thioesterases that use $C_{12}$-ACP (for example, accession number Q41635) and attenuating thioesterases that produce non-$C_{12}$ fatty acids. Acetyl-CoA, malonyl-CoA, and fatty acid overproduction can be verified using methods known in the art, for example, by using radioactive precursors, HPLC, and GC-MS subsequent to cell lysis. Non-limiting examples of thioesterases that can be used in the methods described herein are listed in Table 1.

TABLE 1

Thioesterases

| Accession Number | Source Organism | Gene | Preferential product produced |
|---|---|---|---|
| AAC73596 | E. coli | tesA without leader sequence | $C_{18:1}$ |
| AAC73555 | E. coli | tesB | |
| Q41635, AAA34215 | Umbellularia california | fatB | $C_{12:0}$ |
| Q39513; AAC49269 | Cuphea hookeriana | fatB2 | $C_{8:0}$-$C_{10:0}$ |
| AAC49269; AAC72881 | Cuphea hookeriana | fatB3 | $C_{14:0}$-$C_{16:0}$ |
| Q39473, AAC49151 | Cinnamonum camphorum | fatB | $C_{14:0}$ |
| CAA85388 | Arabidopsis thaliana | fatB [M141T]* | $C_{16:1}$ |
| NP 189147; NP 193041 | Arabidopsis thaliana | fatA | $C_{18:1}$ |
| CAC39106 | Bradyrhiizobium japonicum | fatA | $C_{18:1}$ |
| AAC72883 | Cuphea hookeriana | fatA | $C_{18:1}$ |
| AAL79361 | Helianthus annus | fatA1 | |

*Mayer et al., BMC Plant Biology 7: 1-11, 2007

Formation of Branched Olefins

Olefins can be produced that contain branch points by using branched fatty acids as substrates. For example, although E. coli naturally produces straight chain fatty acids (sFAs), E. coli can be engineered to produce branched chain fatty acids (brFAs) by introducing and expressing or overexpressing genes that provide branched precursors in the E. coli (e.g., bkd, ilv, icm, and fab gene families). Additionally, a host cell can be engineered to express or overexpress genes encoding proteins for the elongation of brFAs (e.g., ACP, FabF, etc.) and/or to delete or attenuate the corresponding host cell genes that normally lead to sFAs.

The first step in forming brFAs is the production of the corresponding α-keto acids by a branched-chain amino acid aminotransferase. Host cells may endogenously include genes encoding such enzymes or such genes can be recombinantly introduced. E. coli, for example, endogenously expresses such an enzyme, IlvE (EC 2.6.1.42; GenBank accession YP_026247). In some host cells, a heterologous branched-chain amino acid aminotransferase may not be expressed. However, E. coli ENE or any other branched-chain amino acid aminotransferase (e.g., IlvE from Lactococcus lactis (GenBank accession AAF34406), IlvE from Pseudomonas putida (GenBank accession NP_745648), or IlvE from Streptomyces coelicolor (GenBank accession NP_629657)), if not endogenous, can be introduced.

The second step is the oxidative decarboxylation of the α-ketoacids to the corresponding branched-chain acyl-CoA. This reaction can be catalyzed by a branched-chain α-keto acid dehydrogenase complex (bkd; EC 1.2.4.4.) (Denoya et al., J. Bacteriol. 177:3504, 1995), which consists of E1α/β (decarboxylase), E2 (dihydrolipoyl transacylase), and E3 (dihydrolipoyl dehydrogenase) subunits. These branched-chain α-keto acid dehydrogenase complexes are similar to pyruvate and α-ketoglutarate dehydrogenase complexes. Any microorganism that possesses brFAs and/or grows on branched-chain amino acids can be used as a source to isolate bkd genes for expression in host cells, for example, E. coli. Furthermore, E. coli has the E3 component as part of its pyruvate dehydrogenase complex (lpd, EC 1.8.1.4, GenBank accession NP_414658). Thus, it can be sufficient to express only the E1 α/β and E2 bkd genes. Table 2 lists non-limiting examples of bkd genes from several microorganisms that can be recombinantly introduced and expressed in a host cell to provide branched-chain acyl-CoA precursors.

TABLE 2

Bkd genes from selected microorganisms

| Organism | Gene | GenBank Accession # |
|---|---|---|
| Streptomyces coelicolor | bkdA1 (E1α) | NP_628006 |
| | bkdB1 (E1β) | NP_628005 |
| | bkdC1 (E2) | NP_638004 |
| Streptomyces coelicolor | bkdA2 (E1α) | NP_733618 |
| | bkdB2 (E1β) | NP_628019 |
| | bkdC2 (E2) | NP_628018 |
| Streptomyces avermitilis | bkdA (E1a) | BAC72074 |
| | bkdB (E1b) | BAC72075 |
| | bkdC (E2) | BAC72076 |
| Streptomyces avermitilis | bkdF (E1α) | BAC72088 |
| | bkdG (E1β) | BAC72089 |
| | bkdH (E2) | BAC72090 |
| Bacillus subtilis | bkdAA (E1α) | NP_390288 |
| | bkdAB (E1β) | NP_390288 |
| | bkdB (E2) | NP_390288 |
| Pseudomonas putida | bkdA1 (E1α) | AAA65614 |
| | bkdA2 (E1β) | AAA65615 |
| | bkdC (E2) | AAA65617 |

In another example, isobutyryl-CoA can be made in a host cell, for example in E. coli, through the coexpression of a crotonyl-CoA reductase (Ccr, EC 1.6.5.5, 1.1.1.1) and isobutyryl-CoA mutase (large subunit IcmA, EC 5.4.99.2; small subunit IcmB, EC 5.4.99.2) (Han and Reynolds, J. Bacteriol. 179:5157, 1997). Crotonyl-CoA is an intermediate in fatty acid biosynthesis in E. coli and other microorganisms. Non-limiting examples of ccr and icm genes from selected microorganisms are listed in Table 3.

TABLE 3

Ccr and icm genes from selected microorganisms

| Organism | Gene | GenBank Accession # |
|---|---|---|
| Streptomyces coelicolor | Ccr | NP_630556 |
| | icmA | NP_629554 |
| | icmB | NP_630904 |
| Streptomyces cinnamonensis | ccr | AAD53915 |
| | icmA | AAC08713 |
| | icmB | AJ246005 |

In addition to expression of the bkd genes, the initiation of brFA biosynthesis utilizes β-ketoacyl-acyl-carrier-protein synthase III (FabH, EC 2.3.1.41) with specificity for branched chain acyl-CoAs (Li et al., J. Bacteriol. 187:3795-3799, 2005). Non-limiting examples of such FabH enzymes are listed in Table 4. fabH genes that are involved in fatty acid biosynthesis of any brFA-containing microorganism can be expressed in a host cell. The Bkd and FabH enzymes from host cells that do not naturally make brFA may not support brFA production. Therefore, bkd and fabH can be expressed recombinantly. Vectors containing the bkd and fabH genes can be inserted into such a host cell. Similarly, the endogenous level of Bkd and FabH production may not be sufficient to produce brFA. In this case, they can be overexpressed. Additionally, other components of the fatty acid biosynthesis pathway can be expressed or overexpressed, such as acyl carrier proteins (ACPs) and β-ketoacyl-acyl-carrier-protein synthase II (fabF, EC 2.3.1.41) (non-limiting examples of candidates are listed in Table 4). In addition to expressing these genes, some genes in the endogenous fatty acid biosynthesis pathway can be attenuated in the host cell (e.g., the E. coli genes fabH (GenBank accession #NP_415609) and/or fabF (GenBank accession #NP_415613)).

TABLE 4

FabH, ACP and fabF genes from selected microorganisms with brFAs

| Organism | Gene | GenBank Accession # |
|---|---|---|
| Streptomyces coelicolor | fabH1 | NP_626634 |
|  | ACP | NP_626635 |
|  | fabF | NP_626636 |
| Streptomyces avermitilis | fabH3 | NP_823466 |
|  | fabC3 (ACP) | NP_823467 |
|  | fabF | NP_823468 |
| Bacillus subtilis | fabH_A | NP_389015 |
|  | fabH_B | NP_388898 |
|  | ACP | NP_389474 |
|  | fabF | NP_389016 |
| Stenotrophomonas maltophilia | SmalDRAFT_0818 (FabH) | ZP_01643059 |
|  | SmalDRAFT_0821 (ACP) | ZP_01643063 |
|  | SmalDRAFT_0822 (FabF) | ZP_01643064 |
| Legionella pneumophila | FabH | YP_123672 |
|  | ACP | YP_123675 |
|  | fabF | YP_123676 |

Formation of Cyclic Olefins

Cyclic olefins can be produced by using cyclic fatty acids as substrates. To produce cyclic fatty acid substrates, genes that provide cyclic precursors (e.g., the ans, chc, and plm gene families) can be introduced into the host cell and expressed to allow initiation of fatty acid biosynthesis from cyclic precursors. For example, to convert a host cell, such as E. coli, into one capable of synthesizing ω-cyclic fatty acids (cyFA), a gene that provides the cyclic precursor cyclohexylcarbonyl-CoA (CHC-CoA) (Cropp et al., Nature Biotech. 18:980-983, 2000) can be introduced and expressed in the host cell. Non-limiting examples of genes that provide CHC-CoA in E. coli include: ansJ, ansK, ansL, chcA, and ansM from the ansatrienin gene cluster of Streptomyces collinus (Chen et al., Eur. J. Biochem. 261: 98-107, 1999) or plmJ, plmK, plmL, chcA, and plmM from the phoslactomycin B gene cluster of Streptomyces sp. HK803 (Palaniappan et al., J. Biol. Chem. 278: 35552-35557, 2003) together with the chcB gene (Patton et al., Biochem. 39:7595-7604, 2000) from S. collinus, S. avermitilis, or S. coelicolor (see Table 5). The genes listed in Table 4 can then be expressed to allow initiation and elongation of ω-cyclic fatty acids. Alternatively, the homologous genes can be isolated from microorganisms that make cyFA and expressed in a host cell (e.g., E. coli).

TABLE 5

Genes for the synthesis of CHC-CoA

| Organism | Gene | GenBank Accession # |
|---|---|---|
| Streptomyces collinus | ansJK | U72144* |
|  | ansL |  |
|  | chcA |  |
|  | ansM |  |
|  | chcB | AF268489 |
| Streptomyces sp. HK803 | pmLJK | AAQ84158 |
|  | pmLL | AAQ84159 |
|  | chcA | AAQ84160 |
|  | pmLM | AAQ84161 |
| Streptomyces coelicolor | chcB/caiD | NP_629292 |
| Streptomyces avermitilis | chcB/caiD | NP_629292 |

*Only chcA is annotated in GenBank entry U72144, ansJKLM are according to Chen et al. (Eur. J. Biochem. 261: 98-107, 1999).

The genes listed in Table 4 (fabH, ACP, and fabF) allow initiation and elongation of ω-cyclic fatty acids because they have broad substrate specificity. If the coexpression of any of these genes with the genes listed in Table 5 does not yield cyFA, then fabH, ACP, and/or fabF homologs from microorganisms that make cyFAs (e.g., those listed in Table 6) can be isolated (e.g., by using degenerate PCR primers or heterologous DNA sequence probes) and coexpressed.

TABLE 6

Non-limiting examples of microorganisms that contain ω-cyclic fatty acids

| Organism | Reference |
|---|---|
| Curtobacterium pusillum | ATCC19096 |
| Alicyclobacillus acidoterrestris | ATCC49025 |
| Alicyclobacillus acidocaldarius | ATCC27009 |
| Alicyclobacillus cycloheptanicus * | Moore, J. Org. Chem. 62: pp. 2173, 1997 |

* Uses cycloheptylcarbonyl-CoA and not cyclohexylcarbonyl-CoA as precursor for cyFA biosynthesis.

Controlling Degree of Saturation in Olefins

The degree of saturation in olefins can be controlled by regulating the degree of saturation of olefin intermediates, for example, fatty acids. The sfa, gns, and fab families of genes can be expressed or overexpressed to control the saturation of fatty acids. For example, host cells can be engineered to produce unsaturated fatty acids by engineering the host cells to overexpress fabB or by growing the host cells at low temperatures (e.g., less than 37° C.). FabB has preference for cis-$\delta^3$decenoyl-ACP and results in unsaturated fatty acid production in E. coli. Overexpression of fabB results in the production of a significant percentage of unsaturated fatty acids (de Mendoza et al., J. Biol. Chem., 258:2098-101, 1983). fabB may be inserted into and expressed in host cells not naturally having the gene. These unsaturated fatty acids can then be used as substrates in host cells that are engineered to produce olefins.

Alternatively, a repressor of fatty acid biosynthesis, for example, fabR (GenBank accession NP_418398), can be deleted, which will result in increased unsaturated fatty acid production in E. coli (Zhang et al., J. Biol. Chem. 277:15558, 2002). Similar deletions may be made in other host cells. A further increase in unsaturated fatty acids can be achieved, for example, by overexpressing fabM (trans-2, cis-3-decenoyl-ACP isomerase, GenBank accession DAA05501) and controlled expression of fabK (trans-2-enoyl-ACP reductase II, GenBank accession NP_357969) from Streptococcus pneumoniae (Marrakchi et al., J. Biol. Chem. 277: 44809, 2002), while deleting *E. coli* fabI (trans-2-enoyl-ACP reductase, GenBank accession NP_415804). In some examples, the endogenous fabF gene can be attenuated. Thus, increasing the percentage of palmitoleate ($C_{16:1}$) produced.

Genetic Engineering of Host Cells to Express Olefins

Various host cells can be used to produce olefins, as described herein. A host cell can be any prokaryotic or eukaryotic cell. For example, a polypeptide described herein can be expressed in bacterial cells, such as *E. coli*, insect cells, yeast or mammalian cells (such as Chinese hamster ovary cells (CHO) cells, COS cells, VERO cells, BHK cells, HeLa cells, Cv1 cells, MDCK cells, 293 cells, 3T3 cells, or PC12 cells). Other exemplary host cells include cells from the members of the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Schizosaccharomyces, Yarrowia,* or *Streptomyces*. Yet other exemplary host cells can be a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, a *Bacillus amyloliquefaciens* cell, a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhizomucor miehei* cell, a *Mucor michei* cell, a *Streptomyces lividans* cell, a *Streptomyces murinus* cell, or an *Actinomycetes* cell. In a preferred embodiment, the host cell is an *E. coli* cell. In a more preferred embodiment, the host cell is from *E. coli* strains B, C, K, or W. Other suitable host cells are known to those skilled in the art.

Various methods well known in the art can be used to genetically engineer host cells to produce olefins. The methods include the use of vectors, preferably expression vectors, containing a nucleic acid encoding an ORF880 polypeptide, polypeptide variant, or a fragment thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell and are thereby replicated along with the host genome. Moreover, certain vectors, such as expression vectors, are capable of directing the expression of genes to which they are operatively linked. In general, expression vectors used in recombinant DNA techniques are often in the form of plasmids. However, other forms of expression vectors, such as viral vectors (e.g., replication defective retroviruses, adenoviruses, and adeno-associated viruses), can also be used.

The recombinant expression vectors described herein include a nucleic acid described herein in a form suitable for expression of the nucleic acid in a host cell. The recombinant expression vectors can include one or more control sequences, selected on the basis of the host cell to be used for expression. The control sequence is operably linked to the nucleic acid sequence to be expressed. Such control sequences are described, for example, in Goeddel, Gene Expression Technology Methods in Enzymology 185, Academic Press, San Diego, Calif. (1990). Control sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors described herein can be introduced into host cells to produce polypeptides, including fusion polypeptides, encoded by the nucleic acids as described herein.

Recombinant expression vectors can be designed for expression of an ORF880 polypeptide or variant in prokaryotic or eukaryotic cells (e.g., bacterial cells, such as *E. coli*, insect cells (using baculovirus expression vectors), yeast cells, or mammalian cells). Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example, by using T7 promoter regulatory sequences and T7 polymerase.

Expression of polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech Inc; Smith et al., *Gene* (1988) 67:31-40), pMAL (New England Biolabs, Beverly, Mass.), and pRITS (Pharmacia, Piscataway, N.J.), which fuse glutathione S-transferase (GST), maltose E binding protein, or protein A, respectively, to the target recombinant polypeptide.

Examples of inducible, non-fusion *E. coli* expression vectors include pTrc (Amann et al., *Gene* (1988) 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant polypeptide expression is to express the polypeptide in a host cell with an impaired capacity to proteolytically cleave the recombinant polypeptide (see Gottesman, Gene Expression Technology:

Methods in Enzymology 185, Academic Press, San Diego, Calif. (1990) 119-128). Another strategy is to alter the nucleic acid sequence to be inserted into an expression vector so that the individual codons for each amino acid are those preferentially utilized in the host cell (Wada et al., *Nucleic Acids Res.* (1992) 20:2111-2118). Such alteration of nucleic acid sequences can be carried out by standard DNA synthesis techniques.

In another embodiment, the host cell is a yeast cell. In this embodiment, the expression vector is a yeast expression vector. Examples of vectors for expression in yeast *S. cerevisiae* include pYepSec1 (Baldari et al., *EMBO J.* (1987) 6:229-234), pMFa (Kurjan et al., *Cell* (1982) 30:933-943), pJRY88 (Schultz et al., *Gene* (1987) 54:113-123), pYES2 (Invitrogen Corporation, San Diego, Calif.), and picZ (Invitrogen Corp, San Diego, Calif.).

Alternatively, a polypeptide described herein can be expressed in insect cells using baculovirus expression vectors. Baculovirus vectors available for expression of proteins in cultured insect cells (e.g., Sf 9 cells) include, for example, the pAc series (Smith et al., *Mol. Cell. Biol.* (1983) 3:2156-2165) and the pVL series (Lucklow et al., *Virology* (1989) 170:31-39).

In yet another embodiment, the nucleic acids described herein can be expressed in mammalian cells using a mammalian expression vector. Examples of mammalian expression vectors include pCDM8 (Seed, *Nature* (1987) 329:840) and pMT2PC (Kaufman et al., *EMBO J.* (1987) 6:187-195). When used in mammalian cells, the expression vector's control functions can be provided by viral regulatory elements. For example, commonly used promoters are derived from polyoma, Adenovirus 2, cytomegalovirus and Simian Virus 40. Other suitable expression systems for both prokaryotic and eukaryotic cells are described in chapters 16 and 17 of Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989.

Vectors can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in, for example, Sambrook et al. (supra).

For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to antibiotics) can be introduced into the host cells along with the gene of interest. Selectable markers include those that confer resistance to drugs, such as ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transfected with the introduced nucleic acid can be identified by drug selection (e.g., cells that have incorporated the selectable marker gene will survive, while the other cells die).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) can be introduced into the host cells along with the gene of interest. Preferred selectable markers include those which confer resistance to drugs, such as G418, hygromycin, and methotrexate. Nucleic acids encoding a selectable marker can be introduced into a host cell on the same vector as that encoding a polypeptide described herein or can be introduced on a separate vector. Cells stably transfected with the introduced nucleic acid can be identified by drug selection (e.g., cells that have incorporated the selectable marker gene will survive, while the other cells die).

In certain instances, an ORF880 polypeptide, polypeptide variant, or a fragment thereof, is produced in a host cell that contains a naturally occurring mutation that results in an increased level of fatty acids in the host cells. In other instances, the host cell is genetically engineered to increase the level of fatty acids in the host cell relative to a corresponding wild-type host cell. For example, the host cell can be genetically engineered to express a reduced level of an acyl-CoA synthase relative to a corresponding wild-type host cell. In one embodiment, the level of expression of one or more genes, e.g., an acyl-CoA synthase gene, is reduced by genetically engineering a "knock out" host cell.

"Gene knockout" refers to a procedure by which the gene encoding the target protein is modified or inactivated so to reduce or eliminate the function of the intact protein. Inactivation of the gene may be performed by general methods such as mutagenesis by UV irradiation or treatment with N-methyl-N'-nitro-N-nitrosoguanidine, site-directed mutagenesis, homologous recombination, insertion-deletion mutagenesis, or "Red-driven integration" (Datsenko et al., *Proc. Natl. Acad. Sci. USA,* 97:6640-45, 2000). For example, in one embodiment, a construct is introduced into a host cell, such that it is possible to select for homologous recombination events in the host cell. One of skill in the art can readily design a knock-out construct including both positive and negative selection genes for efficiently selecting transfected cells that undergo a homologous recombination event with the construct. The alteration in the host cell may be obtained, e.g., by replacing through a single or double crossover recombination a wild type DNA sequence by a DNA sequence containing the alteration. For convenient selection of transformants, the alteration may, e.g., be a DNA sequence encoding an antibiotic resistance marker or a gene complementing a possible auxotrophy of the host cell. Mutations include, but are not limited to, deletion-insertion mutations. An example of such an alteration includes a gene disruption, i.e., a perturbation of a gene such that the product that is normally produced from this gene is not produced in a functional form. This could be due to a complete deletion, a deletion and insertion of a selective marker, an insertion of a selective marker, a frameshift mutation, an in-frame deletion, or a point mutation that leads to premature termination. In some instances, the entire mRNA for the gene is absent. In other situations, the amount of mRNA produced varies.

Any known acyl-CoA synthase gene can be reduced or knocked out in a host cell. Non-limiting examples of acyl-CoA synthase genes include fadD, fadK, BH3103, yhfL, Pfl-4354, EAV15023, fadD1, fadD2, RPC_4074, fadDD35, fadDD22, faa3p or the gene encoding the protein ZP_01644857. Specific examples of acyl-CoA synthase genes include fadDD35 from *M. tuberculosis* H37Rv [NP_217021], fadDD22 from *M. tuberculosis* H37Rv [NP_217464], fadD from *E. coli* [NP_416319], fadK from *E. coli* [YP_416216], fadD from *Acinetobacter* sp. ADP1 [YP_

045024], fadD from *Haemophilus influenza* RdkW20 [NP_438551], fadD from *Rhodopseudomonas palustris* Bis B18 [YP_533919], BH3101 from *Bacillus halodurans* C-125 [NP_243969], Pfl-4354 from *Pseudomonas fluorescens* Pfo-1 [YP_350082], EAV15023 from *Comamonas testosterone* KF-1 [ZP_01520072], yhfL from *B. subtilis* [NP_388908], fadD1 from *P. aeruginosa* PAO1 [NP_251989], fadD1 from *Ralstonia solanacearum* GM1 1000 [NP_520978], fadD2 from *P. aeruginosa* PAO1 [NP_251990], the gene encoding the protein ZP_01644857 from *Stenotrophomonas maltophilia* R551-3, faa3p from *Saccharomyces cerevisiae* [NP_012257], faa1p from *Saccharomyces cerevisiae* [NP_014962], lcfA from *Bacillus subtilis* [CAA99571], or those described in Shockey et al., *Plant. Physiol.* 129:1710-1722, 2002; Caviglia et al., *J. Biol. Chem.* 279:1163-1169, 2004; Knoll et al., *J. Biol. Chem.* 269(23):16348-56, 1994; Johnson et al., *J. Biol. Chem.* 269: 18037-18046, 1994; and Black et al., *J. Biol. Chem.* 267: 25513-25520, 1992.

Transport Proteins

Transport proteins can export polypeptides and hydrocarbons (e.g., olefins) out of a host cell. Many transport and efflux proteins serve to excrete a wide variety of compounds and can be naturally modified to be selective for particular types of hydrocarbons.

Non-limiting examples of suitable transport proteins are ATP-Binding Cassette (ABC) transport proteins, efflux proteins, and fatty acid transporter proteins (FATP). Additional non-limiting examples of suitable transport proteins include the ABC transport proteins from organisms such as *Caenorhabditis elegans, Arabidopsis thalania, Alkaligenes eutrophus,* and *Rhodococcus erythropolis.* Exemplary ABC transport proteins that can be used are listed in FIG. 10 (e.g., CER5, AtMRP5, AmiS2, and AtPGP1). Host cells can also be chosen for their endogenous ability to secrete hydrocarbons. The efficiency of hydrocarbon production and secretion into the host cell environment (e.g., culture medium, fermentation broth) can be expressed as a ratio of intracellular product to extracellular product. In some examples, the ratio can be about 5:1, 4:1, 3:1, 2:1, 1:1, 1:2, 1:3, 1:4, or 1:5.

Fermentation

The production and isolation of olefins can be enhanced by employing beneficial fermentation techniques. One method for maximizing production while reducing costs is increasing the percentage of the carbon source that is converted to hydrocarbon products.

During normal cellular lifecycles, carbon is used in cellular functions, such as producing lipids, saccharides, proteins, organic acids, and nucleic acids. Reducing the amount of carbon necessary for growth-related activities can increase the efficiency of carbon source conversion to product. This can be achieved by, for example, first growing host cells to a desired density (for example, a density achieved at the peak of the log phase of growth). At such a point, replication checkpoint genes can be harnessed to stop the growth of cells. Specifically, quorum sensing mechanisms (reviewed in Camilli et al., *Science* 311:1113, 2006; Venturi *FEMS Microbio. Rev.* 30:274-291, 2006; and Reading et al., *FEMS Microbiol. Lett.* 254:1-11, 2006) can be used to activate checkpoint genes, such as p53, p21, or other checkpoint genes.

Genes that can be activated to stop cell replication and growth in *E. coli* include umuDC genes. The overexpression of umuDC genes stops the progression from stationary phase to exponential growth (Murli et al., *J. of Bact.* 182:1127, 2000). UmuC is a DNA polymerase that can carry out translesion synthesis over non-coding lesions—the mechanistic basis of most UV and chemical mutagenesis. The umuDC gene products are involved in the process of translesion synthesis and also serve as a DNA sequence damage checkpoint. The umuDC gene products include UmuC, UmuD, umuD', UmuD'$_2$C, UmuD'$_2$, and UmuD$_2$. Simultaneously, product-producing genes can be activated, thus minimizing the need for replication and maintenance pathways to be used while an olefin is being made.

The percentage of input carbons converted to olefins can be a cost driver. The more efficient the process is (i.e., the higher the percentage of input carbons converted to olefins), the less expensive the process will be. For oxygen-containing carbon sources (e.g., glucose and other carbohydrate based sources), the oxygen must be released in the form of carbon dioxide. For every 2 oxygen atoms released, a carbon atom is also released leading to a maximal theoretical metabolic efficiency of approximately 34% (w/w) (for fatty acid derived products). This figure, however, changes for other hydrocarbon products and carbon sources. Typical efficiencies in the literature are approximately less than 5%. Host cells engineered to produce olefins can have greater than about 1, 3, 5, 10, 15, 20, 25, and 30% efficiency. In one example, host cells can exhibit an efficiency of about 10% to about 25%. In other examples, such host cells can exhibit an efficiency of about 25% to about 30%. In other examples, host cells can exhibit greater than 30% efficiency.

The host cell can be additionally engineered to express recombinant cellulosomes, such as those described in PCT application number PCT/US2007/003736. These cellulosomes can allow the host cell to use cellulosic material as a carbon source. For example, the host cell can be additionally engineered to express invertases (EC 3.2.1.26) so that sucrose can be used as a carbon source. Similarly, the host cell can be engineered using the teachings described in U.S. Pat. Nos. 5,000,000; 5,028,539; 5,424,202; 5,482,846; and 5,602,030; so that the host cell can assimilate carbon efficiently and use cellulosic materials as carbon sources.

In one example, the fermentation chamber can enclose a fermentation that is undergoing a continuous reduction. In this instance, a stable reductive environment can be created. The electron balance can be maintained by the release of carbon dioxide (in gaseous form). Efforts to augment the NAD/H and NADP/H balance can also facilitate in stabilizing the electron balance. The availability of intracellular NADPH can also be enhanced by engineering the host cell to express an NADH:NADPH transhydrogenase. The expression of one or more NADH:NADPH transhydrogenases converts the NADH produced in glycolysis to NADPH, which can enhance the production of olefins.

For small scale production, the engineered host cells can be grown in batches of, for example, around 100 mL, 500 mL, 1 L, 2 L, 5 L, or 10 L; fermented; and induced to express desired olefins based on the specific genes encoded in the appropriate plasmids. For example, *E. coli* BL21(DE3) cells harboring pBAD24 (with ampicillin resistance and the olefin synthesis pathway) as well as pUMVC1 (with kanamycin resistance and the acetyl CoA/malonyl CoA overexpression system) can be incubated overnight in 2 L flasks at 37° C. shaken at >200 rpm in 500 mL LB medium supplemented with 75 µg/mL ampicillin and 50 µg/mL kanamycin until cultures reach an OD$_{600}$ of >0.8. Upon achieving an OD$_{600}$ of >0.8, the cells can be supplemented with 25 mM sodium proprionate (pH 8.0) to activate the engineered gene systems for production and to stop cellular proliferation by activating UmuC and UmuD proteins. Induction can be performed for 6 h at 30° C. After incubation, the media can be examined for olefins using GC-MS.

For large scale production, the engineered host cells can be grown in batches of 10 L, 100 L, 1000 L or larger; fermented;

and induced to express desired olefins based on the specific genes encoded in the appropriate plasmids. For example, *E. coli* BL21(DE3) cells harboring pBAD24 (with ampicillin resistance and the olefin synthesis pathway) as well as pUMVC1 (with kanamycin resistance and the acetyl-CoA/malonyl-CoA overexpression system) can be incubated from a 500 mL seed culture for 10 L fermentations (5 L for 100 L fermentations, etc.) in LB media (glycerol free) with 50 µg/mL kanamycin and 75 µg/mL ampicillin at 37° C., and shaken at >200 rpm until cultures reach an OD600 of >0.8 (typically 16 h). Media can be continuously supplemented to maintain 25 mM sodium proprionate (pH 8.0) to activate the engineered gene systems for production and to stop cellular proliferation by activating umuC and umuD proteins. Media can be continuously supplemented with glucose to maintain a concentration 25 g/100 mL.

After the first hour of induction, aliquots of no more than 10% of the total cell volume can be removed each hour and allowed to sit without agitation to allow the olefins to rise to the surface and undergo a spontaneous phase separation. The olefin component can then be collected, and the aqueous phase returned to the reaction chamber. The reaction chamber can be operated continuously. When the $OD_{600}$ drops below 0.6, the cells can be replaced with a new batch grown from a seed culture.

Producing Olefins Using Cell-Free Methods

In some methods described herein, an olefin can be produced using a purified polypeptide described herein and a fatty acid substrate. For example, a host cell can be engineered to express a polypeptide (e.g., an ORF880 polypeptide or variant) as described herein. The host cell can be cultured under conditions suitable to allow expression of the polypeptide. Cell free extracts can then be generated using known methods. For example, the host cells can be lysed using detergents or by sonication. The expressed polypeptides can be purified using known methods. After obtaining the cell free extracts, fatty acid substrates described herein can be added to the cell free extracts and maintained under conditions to allow conversion of the fatty acid substrates to olefins. The olefins can then be separated and purified using known techniques.

Post-Production Processing

The olefins produced during fermentation can be separated from the fermentation media. Any known technique for separating olefins from aqueous media can be used. One exemplary separation process is a two phase (bi-phasic) separation process. This process involves fermenting the genetically engineered host cells under conditions sufficient to produce an olefin, allowing the olefin to collect in an organic phase, and separating the organic phase from the aqueous fermentation broth. This method can be practiced in both a batch and continuous fermentation setting.

Bi-phasic separation uses the relative immiscibility of olefins to facilitate separation. Immiscible refers to the relative inability of a compound to dissolve in water and is defined by the compound's partition coefficient. One of ordinary skill in the art will appreciate that by choosing a fermentation broth and organic phase, such that the olefin being produced has a high log P value, the olefin can separate into the organic phase, even at very low concentrations, in the fermentation vessel.

The olefins produced by the methods described herein can be relatively immiscible in the fermentation broth, as well as in the cytoplasm. Therefore, the olefin can collect in an organic phase either intracellularly or extracellularly. The collection of the products in the organic phase can lessen the impact of the olefin on cellular function and can allow the host cell to produce more product.

The methods described herein can result in the production of homogeneous compounds wherein at least about 60%, 70%, 80%, 90%, or 95% of the olefins produced will have carbon chain lengths that vary by less than about 6 carbons, less than about 4 carbons, or less than about 2 carbons. These compounds can also be produced with a relatively uniform degree of saturation. For example, at least about 60%, 70%, 80%, 90%, or 95% of the olefins will be monounsaturated, diunsaturated, or triunsaturated. These compounds can be used directly as fuels, fuel additives, starting materials for production of other chemical compounds (e.g., polymers, surfactants, plastics, textiles, solvents, adhesives, etc.), or personal care additives. These compounds can also be used as feedstock for subsequent reactions, for example, hydrogenation, catalytic cracking (via hydrogenation, pyrolysis, or both), or epoxidation reactions to make other products.

In some embodiments, the olefins produced using methods described herein can contain between about 50% and about 90% carbon; between about 5% and about 25% hydrogen; or between about 5% and about 25% oxygen. In other embodiments, the olefins produced using methods described herein can contain between about 65% and about 85% carbon; between about 10% and about 15% hydrogen; or between about 10% and about 20% oxygen.

Fuel Compositions

The olefins described herein can be used as or converted into a fuel. One of ordinary skill in the art will appreciate that, depending upon the intended purpose of the fuel, different olefins can be produced and used. For example, a branched olefin may be desirable for automobile fuel that is intended to be used in cold climates. In addition, when the olefins described herein are used as a feedstock for fuel production, one of ordinary skill in the art will appreciate that the characteristics of the olefin feedstock will affect the characteristics of the fuel produced. Hence, the characteristics of the fuel product can be selected for by producing particular olefins for use as a feedstock.

Using the methods described herein, biofuels having desired fuel qualities can be produced from olefins. Biologically produced olefins represent a new source of biofuels, which can be used as jet fuel, diesel, or gasoline. Some biofuels made using olefins have not been produced from renewable sources and are new compositions of matter. These new fuels can be distinguished from fuels derived from petrochemical carbon on the basis of dual carbon-isotopic fingerprinting. Additionally, the specific source of biosourced carbon (e.g., glucose vs. glycerol) can be determined by dual carbon-isotopic fingerprinting (see, e.g., U.S. Pat. No. 7,169,588, in particular col. 4, line 31, to col. 6, line 8).

Hydrocarbons comprising biologically produced hydrocarbons, particularly α-olefins biologically produced using the fatty acid biosynthetic pathway, have not been produced from renewable sources and, as such, are new compositions of matter. These new hydrocarbons can be distinguished from hydrocarbons derived from petrochemical carbon on the basis of dual carbon-isotopic fingerprinting or $^{14}$C dating. Additionally, the specific source of biosourced carbon (e.g., glucose vs. glycerol) can be determined by dual carbon-isotopic fingerprinting (see U.S. Pat. No. 7,169,588, which is herein incorporated by reference).

The ability to distinguish biologically produced hydrocarbons from petroleum based hydrocarbons is beneficial in tracking these materials in commerce. For example, hydrocarbons or chemicals comprising both biologically based and petroleum based carbon isotope profiles may be distinguished from hydrocarbons and chemicals made only of petroleum based materials. Hence, the instant materials may be followed in commerce on the basis of their unique carbon isotope profile.

Hydrocarbons can be distinguished from petroleum based fuels by comparing the stable carbon isotope ratio ($^{13}C/^{12}C$) in each fuel. The $^{13}C/^{12}C$ ratio in a given biologically based material is a consequence of the $^{13}C/^{12}C$ ratio in atmospheric carbon dioxide at the time the carbon dioxide is fixed. It also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway.

Within the precision of measurement, $^{13}C$ shows large variations due to isotopic fractionation effects, the most significant of which for biologically produced hydrocarbons is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the "$C_3$" (or Calvin-Benson) photosynthetic cycle and those that incorporate the "$C_4$" (or Hatch-Slack) photosynthetic cycle.

In $C_3$ plants, the primary $CO_2$ fixation or carboxylation reaction involves the enzyme ribulose-1,5-diphosphate carboxylase and the first stable product is a 3-carbon compound. $C_3$ plants, such as hardwoods and conifers, are dominant in the temperate climate zones.

In $C_4$ plants, an additional carboxylation reaction involving another enzyme, phosphoenol-pyruvate carboxylase, is the primary carboxylation reaction. The first stable carbon compound is a 4-carbon acid which is subsequently decarboxylated. The $CO_2$ thus released is refixed by the $C_3$ cycle. Examples of $C_4$ plants are tropical grasses, corn, and sugar cane.

Both $C_4$ and $C_3$ plants exhibit a range of $^{13}C/^{12}C$ isotopic ratios, but typical values are about –7 to about –13 per mil for $C_4$ plants and about –19 to about –27 per mil for $C_3$ plants (see, e.g., Stuiver et al., *Radiocarbon*, 19: 355 (1977)). Coal and petroleum fall generally in this latter range. The $^{13}C$ measurement scale was originally defined by a zero set by Pee Dee Belemnite (PDB) limestone, where values are given in parts per thousand deviations from this material. The "$\delta^{13}C$", values are in parts per thousand (per mil), abbreviated, ‰, and are calculated as follows:

$$\delta^{13}C(\text{‰})=[(^{13}C/^{12}C)_{sample}-(^{13}C/^{12}C)_{standard}]/(^{13}C/^{12}C)_{standard}\times 1000$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46.

The invention provides a hydrocarbon or biofuel produced by any of the methods disclosed herein. Specifically, the hydrocarbon or biofuel can have a $\delta^{13}C$ of about –28 or greater, about –27 or greater, –20 or greater, –18 or greater, –15 or greater, –13 or greater, –10 or greater, and –8 or greater. For example, the hydrocarbon can have a $\delta^{13}C$ of about –30 to about –15, about –27 to about –19, about –25 to about –21, about –15 to about –5, about –13 to about –7, about –13 to about –10. In some examples, a biofuel composition can be made that includes an olefin having $\delta^{13}C$ of from about –10.9 to about –15.4, where the olefin accounts for at least about 85% of biosourced material (i.e., derived from a renewable resource, such as biomass, cellulosic materials, and sugars) in the composition. The invention also provides for a hydrocarbon or biofuel with a $\delta^{13}C$ of about –10, –11, –12, or –12.3.

Biologically produced hydrocarbons can also be distinguished from petroleum based hydrocarbons by comparing the amount of $^{14}C$ in each fuel. Because $^{14}C$ has a nuclear half life of 5730 years, petroleum based fuels containing "older" carbon can be distinguished from biofuels which contain "newer" carbon (see, e.g., Currie, "Source Apportionment of Atmospheric Particles," *Characterization of Environmental Particles*, J. Buffle and H. P. van Leeuwen, Eds., 1 of Vol. I of the IUPAC Environmental Analytical Chemistry Series (Lewis Publishers, Inc) (1992) 3-74).

The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about $1.2\times 10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.)

It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C. As used herein, "fraction of modern carbon" or "$f_M$" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

The invention provides a hydrocarbon or biofuel which can have an $f_M$ $^{14}C$ of at least about 1. For example, the hydrocarbon or biofuel can have an $f_M$ $^{14}C$ of at least about 1.01, an $f_M$ $^{14}C$ of about 1 to about 1.5, an $f_M$ $^{14}C$ of about 1.04 to about 1.18, or an $f_M$ $^{14}C$ of about 1.111 to about 1.124. In some examples, the olefin in the biofuel composition can have a fraction of modern carbon ($f_M$ $^{14}C$) of, for example, at least about 1.003, 1.010, or 1.5.

Another measurement of $^{14}C$ is known as the percent of modern carbon, pMC. For an archaeologist or geologist using $^{14}C$ dates, AD 1950 equals "zero years old". This also represents 100 pMC. "Bomb carbon" in the atmosphere reached almost twice the normal level in 1963 at the peak of thermonuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC.

A biologically based carbon content is derived by assigning 100% equal to 107.5 pMC and 0% equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material.

The invention provides a hydrocarbon or biofuel which can have a pMC of at least about 50, 60, 70, 75, 80, 85, 90, 95, 96, 97, 98, 99, or 100. The invention further provides for a hydrocarbon or fuel which has a pMC of between about 50 to about 100, about 60 to about 100, about 70 to about 100, about 80 to about 100, about 85 to about 100, and about 87 to about 98, about 90 to about 95. The invention further provides for a hydrocarbon or biofuel with a pMC of about 90, 91, 92, 93, 94, or 94.2.

Fuel additives are used to enhance the performance of a fuel or engine. For example, fuel additives can be used to alter the freezing/gelling point, cloud point, lubricity, viscosity, oxidative stability, ignition quality, octane level, and/or flash point. In the United States, all fuel additives must be registered with Environmental Protection Agency. The names of fuel additives and the companies that sell the fuel additives are publicly available by contacting the EPA or by viewing the agency's website. One of ordinary skill in the art will appreciate that the olefin-based biofuels described herein can be mixed with one or more fuel additives to impart a desired quality.

The olefin-based biofuels described herein can be mixed with other fuels, such as various alcohols, such as ethanol and butanol, and petroleum-derived products, such as gasoline, diesel, or jet fuel.

In some examples, the mixture can include at least about 10%, 15%, 20%, 30%, 40%, 50%, or 60% by weight of the olefin. In other examples, a biofuel composition can be made that includes at least about 5%, 10%, 20%, 30%, 40%, 50%, 60%, 70%, 80%, 85%, 90% or 95% of an olefin that includes a carbon chain that is 8:1, 10:1, 12:1, 13:1, 14:1, 14:2, 15:1, 15:2, 16:1, 16:2, 17:1, 17:2, 18:1, 18:2, 18:3, 19:1, 19:2, 19:3, 20:1, 20:2, 20:3, 22:1, 22:2, or 22:3. Such biofuel compositions can additionally include at least one additive selected from a cloud point lowering additive that can lower the cloud point to less than about 5° C., or 0° C.; a surfactant; a microemulsion; at least about 5%, 10%, 15%, 20%, 30%, 40%, 50%, 60%, 70%, 80%, 85%, 90%, or 95% diesel fuel from triglycerides; petroleum-derived gasoline; or diesel fuel from petroleum.

EXAMPLES

The invention is further described in the following examples, which do not limit the scope of the invention described in the claims.

Example 1

Identification and Reclassification of a Microorganism Belonging to the Genus *Jeotgalicoccus* that is an α-olefin Producer

*Micrococcus candicans* ATCC 8456 was previously reported to synthesize aliphatic hydrocarbons with carbon chain lengths ranging from $C_{18}$ to $C_{20}$ (Morrison et al., *J. Bacteriol.* 108:353-358, 1971). To identify the hydrocarbons produced by this strain, ATCC 8456 cells were cultured in 15 mL TSBYE medium (3% Tryptic Soy Broth+0.5% Yeast Extract), for 40-48 h at 30° C. Cells from 5 mL of culture were pelleted, resuspended in 1 mL methanol, sonicated for 30 min and extracted with 4 mL hexane. After solvent evaporation, samples were resuspended in 0.1 mL hexane and analyzed by GC-MS. The hydrocarbons were identified as the following α-olefins: 15-methyl-1-heptadecene (a-$C_{18}$), 16-methyl-1-heptadecene (i-$C_{18}$), 1-nonadecene (n-$C_{19}$), 17-methyl-1-nonadecene (a-$C_{20}$) and 18-methyl-1-nonadecene (i-$C_{20}$) (i=iso, a=anteiso, n=straight chain) (see, e.g., FIG. 1 and FIG. 2).

Based upon the following analyses, it was determined that ATCC 8456 was previously misidentified as belonging to the genus *Micrococci*. The phylogenetic classification of ATCC 8456 was reassessed by amplifying and sequencing the partial 16s rRNA gene using primers Eubac27 and 1492R (see DeLong et al., *PNAS* 89:5685, 1992). The 16s rRNA sequence of ATCC8456 (SEQ ID NO:3, depicted in FIG. 7C) was analyzed using the classifier program of the Ribosomal Database Project II. Based upon this analysis, the strain was identified as belonging to the genus *Jeotgalicoccus*. The genus *Jeotgalicoccus* has been previously described (see, e.g., Jung-Hoon et al., *Int. J. Syst. Evol. Microbiol.* 53:595-602, 2003).

Figure 3:
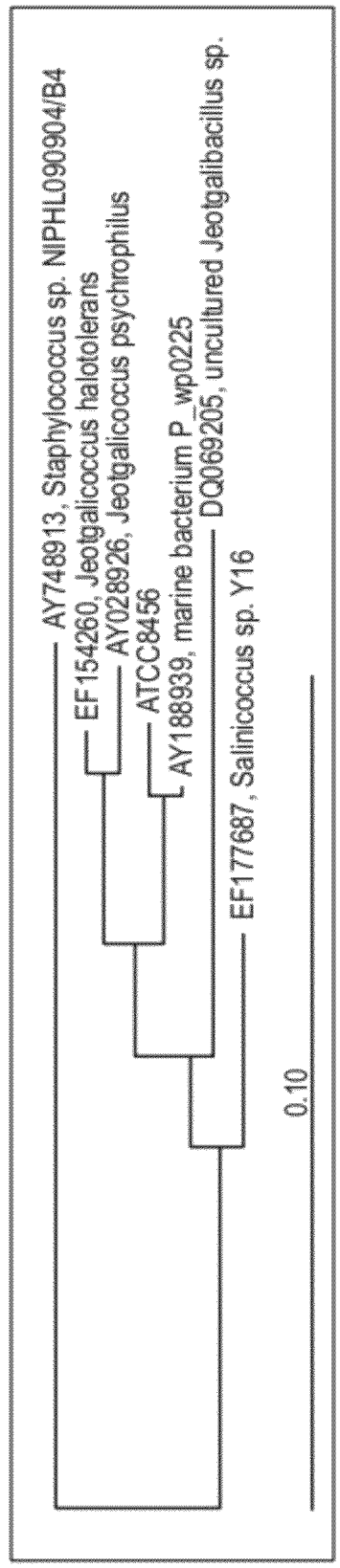
FIG. 3 is a schematic of a phylogenetic analysis of 16s rRNA of *Jeotgalicoccus* ATCC 8456.

Additional analysis using the G+C content of ATCC 8456 was conducted. *Jeotgalicoccus* is a low G+C Gram-positive bacteria related to the genus *Staphylococcus* (see FIG. 3). *Micrococci* are high G+C Gram-positive bacteria. The ends of several clones from a cosmid library of ATCC 8456 genomic DNA were sequenced. Based upon a DNA sequence of approximately 4,000 bp, the G+C content was determined to be approximately 36%. Nucleotide sequence searches against a non-redundant protein database revealed that all sequences with a match to a database entry were similar to proteins from low G+C Gram-positive bacteria, such as species belonging to the genus *Staphylococcus* or *Bacillus*, but not the genus *Micrococcus*.

Next, an analysis of the entire genome of ATCC 8456 was conducted. Based on a DNA sequence of approximately 2.1 MB, the G+C content of the entire genome was determined to be about 36.7%. In contrast, bacteria of the genus *Micrococcus* are known to have high G+C genomes. For example, the genome of *Micrococcus luteus* NCTC 2665 has a G+G content of 72.9% (GenBank Accession ABLQ01000001-68). Based upon the G+C content analysis, it was determined that the ATCC 8456 microorganism does not belong to the genus *Micrococcus*.

Figure 1B:
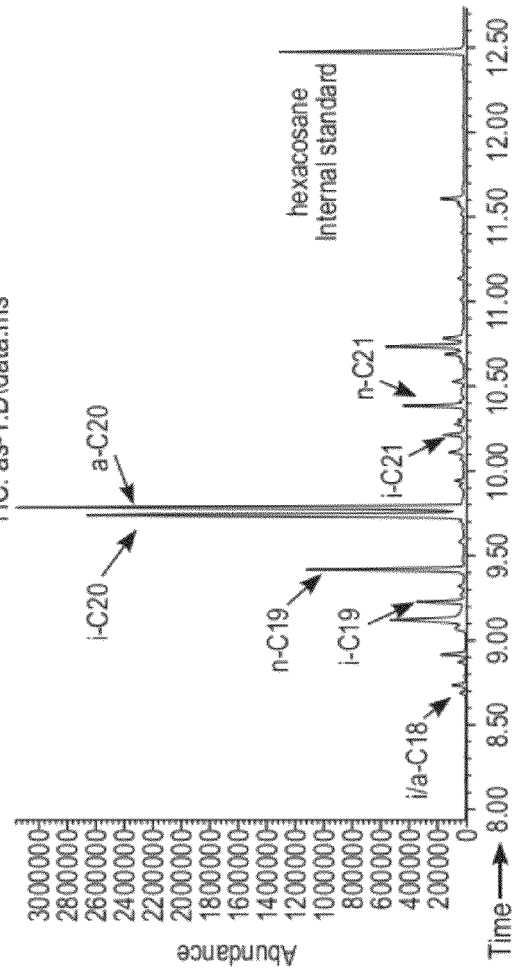
Figure 2A:
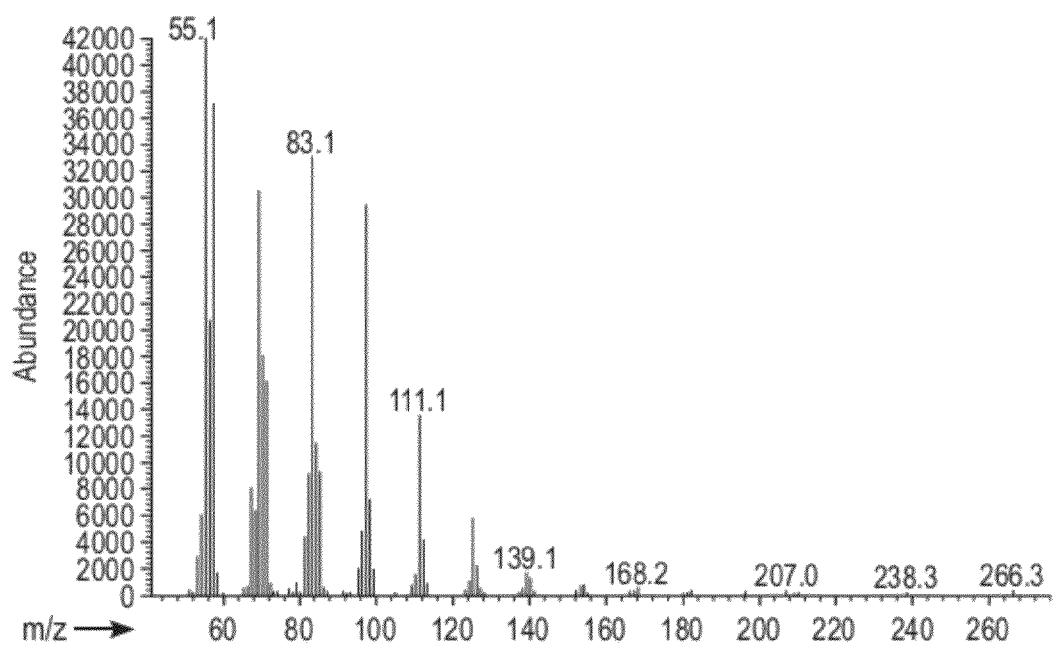
FIGS. 2A and 2B are mass spectrometry fragmentation patterns of two α-olefins produced by *Jeotgalicoccus* ATCC 8456 cells. Compound A was identified as 1-nonadecene and compound B as 18-methyl-1-nonadecene.
Figure 2B:
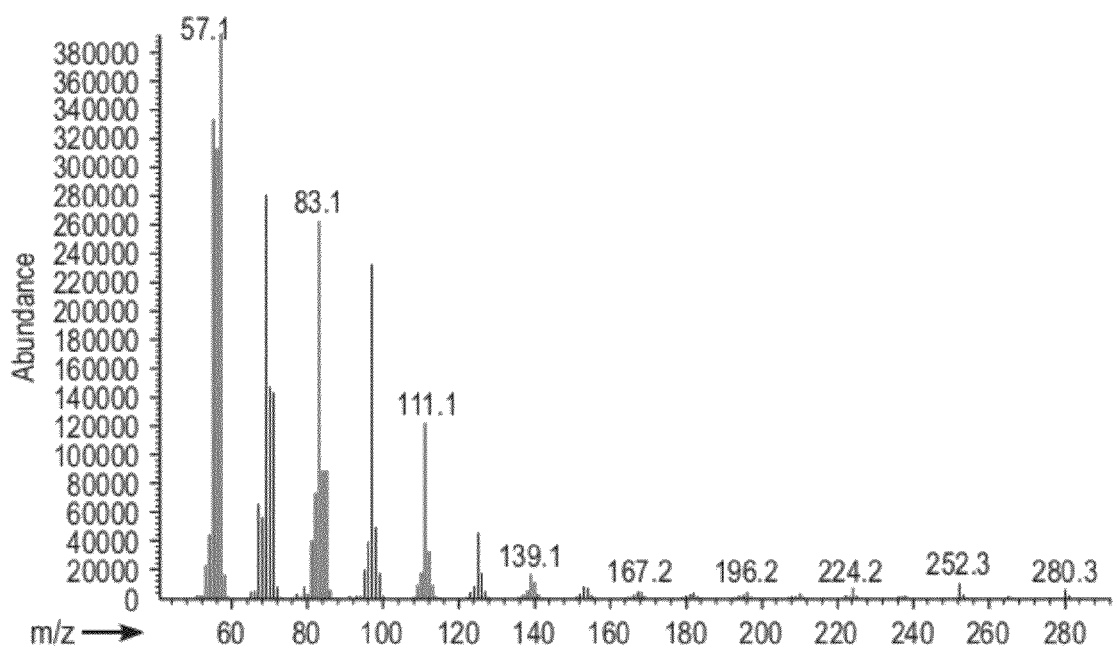

Additional *Jeotgalicoccus* strains were also examined to determine if they produced α-olefins. The following strains of *Jeotgalicoccus* were examined: *Jeotgalicoccus halotolerans* DSMZ 17274, *Jeotgalicoccus psychrophilus* DSMZ 19085, and *Jeotgalicoccus pinnipedalis* DSMZ 17030. Each strain was cultured in 15 mL TSBYE medium (3% Tryptic Soy Broth+0.5% Yeast Extract), and the hydrocarbons were isolated and analyzed by GC-MS as described above. All three strains produced α-olefins similar to the ones produced by ATCC 8456 (FIGS. 1B, 1C, and 1D depict GC-MS traces for the hydrocarbons produced by *Jeotgalicoccus halotolerans* DSMZ 17274 cells, *Jeotgalicoccus pinnipedalis* DSMZ 17030 cells, and *Jeotgalicoccus psychrophilus* DSMZ 19085 cells, respectively). These data indicate that the ability to produce α-olefins is widespread among the genus *Jeotgalicoccus*.

Example 2

Production of Increased Levels of Olefins and α-Olefins not Normally Produced by ATCC 8456 Cells Using Fatty Acid Feeding The fatty acids eicosanoic acid (straight-chain $C_{20}$ fatty acid), 16-methyl octadecanoic acid, and 17-methyl octadecanoic acid (branched-chain $C_{19}$ fatty acids) were identified as components of ATCC 8456's lipids. These fatty acids were deduced to be the direct precursors, after decarboxylation, for 1-nonadecene, 15-methyl-1-heptadecene, and 16-methyl-1-heptadecene biosynthesis, respectively. In order to improve α-olefin production and to produce olefins not normally produced by ATCC 8456 cells, fatty acid feeding experiments were carried out as described below.

ATCC 8456 cells were grown in 15 mL TSBYE medium (3% Tryptic Soy Broth+0.5% Yeast Extract). Fatty acids were added to the culture medium at final concentrations of 0.5 g/l (0.05%). After growth for 40-48 h at 30° C., cells from 5 mL of culture were pelleted, resuspended in 1 mL methanol, sonicated for 30 min, and extracted with 4 mL hexane. After solvent evaporation, samples were resuspended in 0.1 mL hexane and analyzed by GC-MS.

Figure 4A:
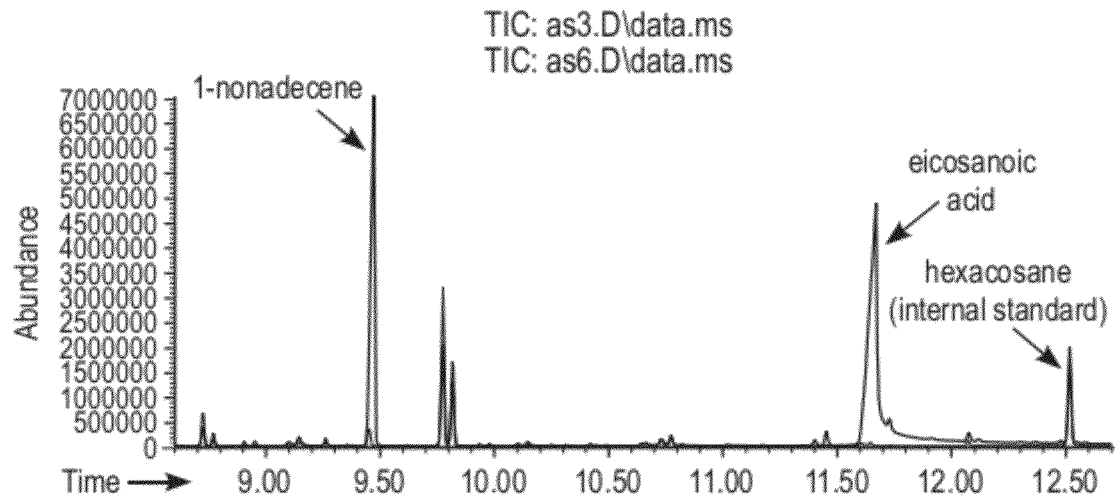
FIGS. 4A and 4B are GC/MS traces of α-olefins produced by *Jeotgalicoccus* sp. ATCC 8456 cells upon feeding with eisosanoic acid (FIG. 4A) or stearic acid (FIG. 4B).
Figure 4B:
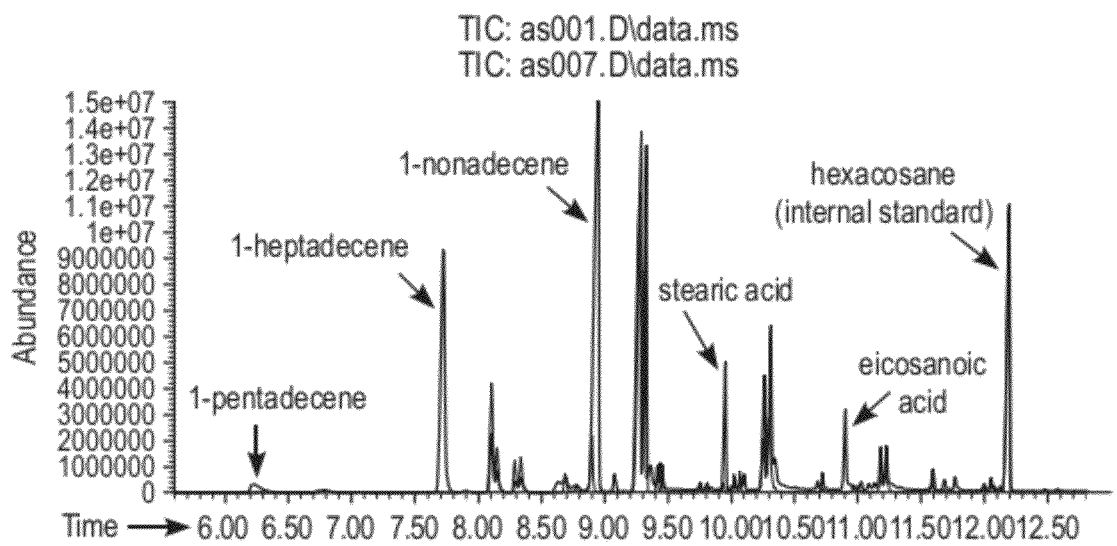

When cultures were fed eicosanoic acid, an increase in 1-nonadecene production of approximately 18-fold was observed (see FIG. 4A; black traces depict production without fatty acid feeding and gray traces depict production with fatty acid feeding). When cultures were fed stearic acid or palmitic acid, an increase in the production of the α-olefins 1-pentadecene and 1-heptadecene, respectively, was observed (see FIG. 4B). These olefins are not normally produced by ATCC 8456 cells. This indicated that fatty acids were the direct precursors for α-olefins and that *Jeotgalicoccus* bacteria could be used to enzymatically convert fatty acids into α-olefins in vivo.

In alternative methods, when resting *Jeotgalicoccus* cells are fed various fatty acids and the production of α-olefins is analyzed, similar results are observed.

Example 3

In Vitro Synthesis of α-Olefins Using Cell Extracts and Partially Purified Proteins A cell free extract of ATCC 8456 was used to convert free fatty acids into α-olefins. The cell free extract was generated using the following procedure: ATCC 8456 cells were grown in TSBYE medium (3% Tryptic Soy Broth+0.5% Yeast Extract) at 30° C. for 24 h with shaking. The cells were then pelleted from the culture by centrifuging at 3,700 rpm for 20 min. The cell pellet was then resuspended in 50 mM Tris buffer pH 7.5 with 0.1 M NaCl and 2.0 mM dithiothreitol to a concentration of 0.1 g/mL cells. To this cell slurry, 200 units/mL of lysostaphin (Sigma) were added on ice. The cell lysis reaction was allowed to proceed for 30 min. The cells were then sonicated at 12 W on ice for three cycles of 1.5 sec of sonication followed by 1.5 sec of rest. Sonication lasted for a total of 9 sec. This procedure was repeated 5 times with a 1 min interval between each sonication cycle. The lysed cells were then centrifuged at 12,000 rpm for 10 min to pellet the cell debris. The supernatant (i.e., cell free extract) was then removed and used for the conversion of free fatty acids to α-olefins.

After obtaining the cell free extract, the free fatty acids, stearic acid and eicosanoic acid, were converted to α-olefins using the cell free extract as described below.

First, a 5% stock solution of sodium or potassium stearate was made in 1% Tergitol solution (Sigma, St. Louis, Mo.). Next, 6 μL of the stock solution was added to 1 mL of the cell free extract at room temperature to obtain a final concentration of 1 mM free fatty acid salt. The reaction was conducted at room temperature for 3 h. The α-olefins were recovered by adding 200 μL of ethyl acetate to the mixture, vortexing briefly, centrifuging briefly, and then removing the organic phase. The α-olefins were detected using GC/MS.

Figure 5:
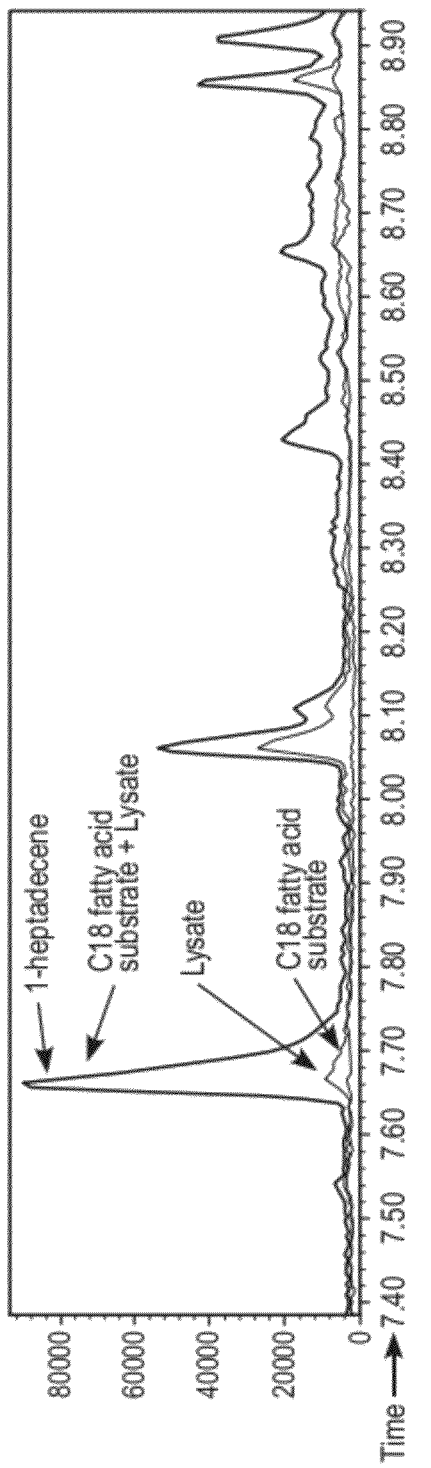
FIG. 5 is a GC/MS trace of α-olefins produced by cell free lysates of *Jeotgalicoccus* sp. ATCC 8456 cells.

FIG. 5 shows the GC/MS trace for assaying stearic acid. In sample 1 (TIC1; black line in FIG. 5), no stearic acid was added to the cell free extract. In sample 2 (TIC3; blue line in FIG. 5), the cell free extract was replaced with 50 mM Tris pH 7.5 buffer with 0.1 M sodium chloride to which stearic acid was added. In sample 3 (TICS; red line in FIG. 5), stearic acid was added to the cell free extract. The peak at 7.62 min had the same retention time and the same mass spectra as a 1-heptadecene standard (Sigma). When eicosanoic acid was added under similar conditions, 1-nonadecene was formed.

Boiling the cell free extract eliminated the production of α-olefins upon the addition of free fatty acids. This data strongly suggested that the ATCC 8456 catalyst was protein based.

The ATCC 8456 cell free extract did not require any additional co-factors to produce α-olefins. When the cell free extract was supplemented with several co-factors in 1 mM concentrations, no increase in α-olefin synthesis was observed. The co-factors examined were NAD+, NADP+, NADH, NADPH, $FADH_2$, SAM, ATP, and CoA. In addition, $Mg^{2+}$ was examined at a 10 mM concentration. The co-factor requirement was also tested by dialyzing the cell free extract with a 10 kDa cut-off membrane for 1.5 h in a volume 200-fold greater than the cell extract volume using a dialysis buffer: 50 mM Tris, pH 7.5 with 0.1 M sodium chloride. No decrease in α-olefin synthesis was observed after dialysis. Additionally, no decrease in α-olefin synthesis was observed when 10 mM EDTA pH 7.5 was added to the reaction mixture.

The ATCC 8456 cell free extract was further enriched by carrying out an ammonium sulfate precipitation. First, enough ammonium sulfate was added to the cell free extract to bring the concentration of ammonium sulfate to 50% (wt/vol) saturation. The mixture was stirred gently on ice for 60 min and then centrifuged at 13,000 rpm for 30 min. The supernatant was recovered and additional ammonium sulfate was added to bring the ammonium sulfate concentration to 65% (wt/vol). The mixture was allowed to mix on ice for 60 min and was centrifuged again for 30 min. The supernatant was discarded. The pellet was then resuspended in 50 mM Tris buffer pH 7.5 with 0.1 M sodium chloride. This mixture was then dialyzed in the aforementioned buffer to remove the ammonium sulfate. The cell free extract treated with ammonium sulfate had the same α-olefin synthesizing activity as the cell free extract.

Example 4

Purification and Identification of a Protein that Converts Fatty Acids into α-Olefins To isolate the protein necessary for α-olefin production from ATCC 8456 cells, the following protein purification procedure was carried out. First, 6 L of ATCC 8456 cells were cultured in TSBYE medium at 30° C. for 24 h with shaking. The cells were pelleted at 3,700 rpm for 20 min at 4° C., and the supernatant was discarded. The cell pellet was resuspended in a solution of 100 mL of 50 mM Tris pH 8.0, 0.1 M NaCl, 2.0 mM DTT, and bacterial protease inhibitors. The cell slurry was then passed through a french press one time at a pressure of 30,000 psi. Next, the cell slurry was sonicated as described in Example 3 to shear the DNA. The cell free extract was next centrifuged at 10,000 rpm for 60 min at 4° C. The supernatant was then removed and ammonium sulfate was added to a final concentration of 50% (wt/vol) ammonium sulfate saturation. The mixture was gently stirred at 4° C. for 60 min and then centrifuged at 10,000 rpm for 30 min. The supernatant was then removed and additional ammonium sulfate was added to 65% (wt/vol) saturation. The mixture was stirred again for 60 min at 4° C. and centrifuged at 10,000 rpm for 30 min. The supernatant was discarded. The remaining pellet was resuspended in 50 mL of 50 mM Tris pH 8.0 and 2.0 mM DTT.

The mixture was passed through a 5 mL HiTrap SP column (GE Healthcare) at 3 mL/min and 4° C. The following buffers were used as an elution gradient: buffer A contained 50 mM Tris pH 8.0 and 2.0 mM DTT and buffer B contained 50 mM Tris pH 8.0, 1.0 M NaCl, and 2.0 mM DTT. After the column was loaded with the mixture, the column was washed with 40% buffer B. Next a 20 min gradient of 40% buffer B to 100% buffer B at 3.0 mL/min was carried out. 5 mL fractions were collected during the elution gradient. Each fraction was tested for activity as described in Example 3. Fractions containing α-olefin production activity typically eluted between 600 and 750 mM NaCl concentration. Fractions containing activity were then pooled and dialyzed into buffer A.

Figure 6:
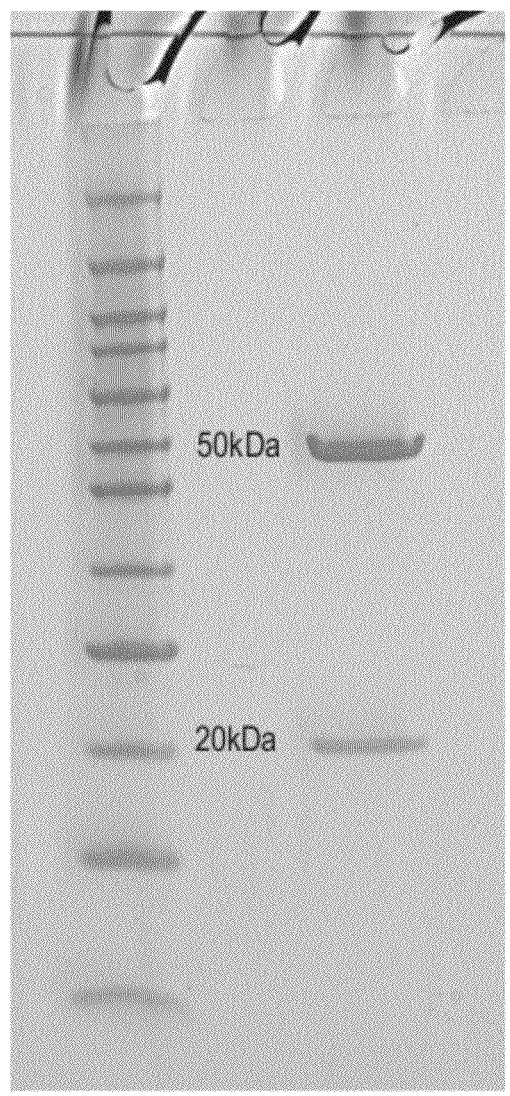
FIG. 6 is a digital representation of an SDS-PAGE gel of final purified α-olefins-producing protein fraction from *Jeotgalicoccus* sp. ATCC 8456 cells.

The dialyzed protein fraction was then loaded onto a 1 mL ResourceQ (GE Healthcare) column at 4 mL/min at 4° C. Buffer B used with the HiTrap SP column was used for the ResourceQ column. A 7-min elution gradient between 0% buffer B and 25% buffer B was run at 4 mL/min. 1.5 mL fractions were collected and assayed for activity. Active fractions eluted between 150 and 200 mM NaCl concentrations. Fractions containing activity were then pooled and concentrated with a Millipore Amicon protein concentrator (4 mL and 10 kDa exclusion size) to about 50 μL. The approximate protein concentration was determined with a Bradford assay (Biorad). Final protein concentrations ranged from about 5 mg/mL to about 10 mg/mL. 30 μL of protein was then loaded onto a SDS PAGE gel (Invitrogen) along with an appropriate protein molecular weight marker. The gel was stained with Simple Safe Coomassie stain (Invitrogen). FIG. 6 depicts a representative gel. Two intense protein bands at 50 kDa and 20 kDa were observed.

To determine the identity of the protein bands, the bands were excised from the gel, digested with trypsin, and analyzed using LC/MS/MS. The LC/MS/MS data was analyzed using the program Mascot (Mann et al., *Anal. Chem.* 66:4390-4399, 1994). The ATCC 8456 genome was sequenced. The genomic data was used to interpret the LC/MS/MS data and to determine the identity of the protein bands. The 50 kDa band had a strong match with ORF880. The Mascot score assigned to this match was 919, a high score. Furthermore, ORF880 has a predicted molecular weight of 48,367 Da. The nucleotide and amino acid sequences of orf880 are presented in FIGS. 7A (SEQ ID NO:1) and 7B (SEQ ID NO:2), respectively.

Example 5

Heterologous Expression of *Jeotgalicoccus* ATCC 8456 orf880 in *E. coli*

Figure 8:
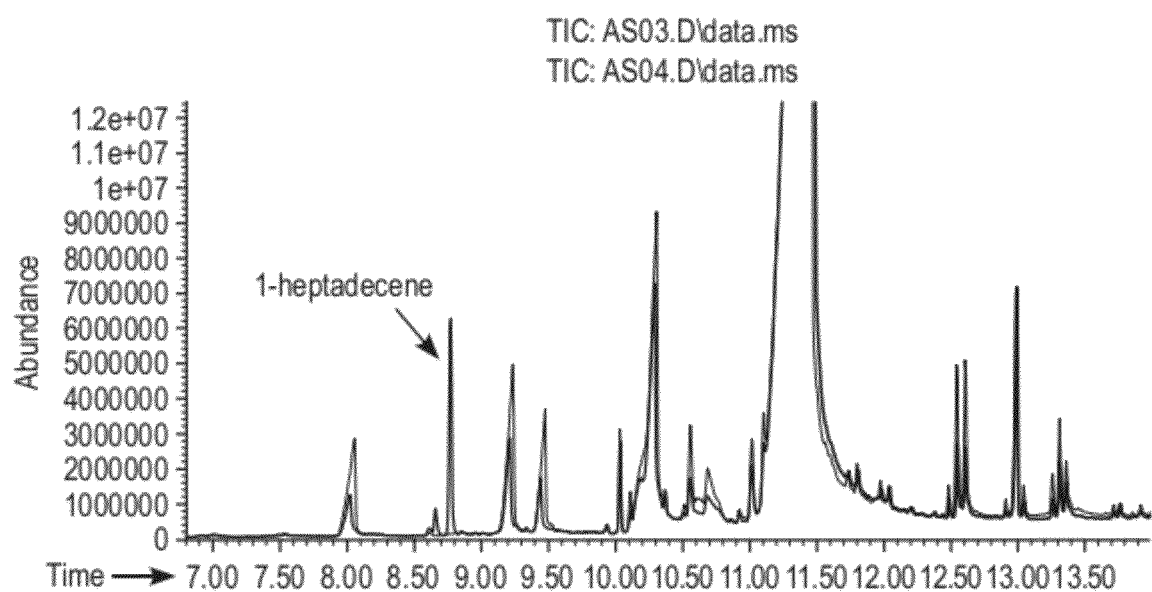
FIG. 8 is a GC/MS trace of α-olefins produced by *E. coli* upon expression of *Jeotgalicoccus* sp. 8456_orf880 and feeding of stearic acid.
Figure 9:
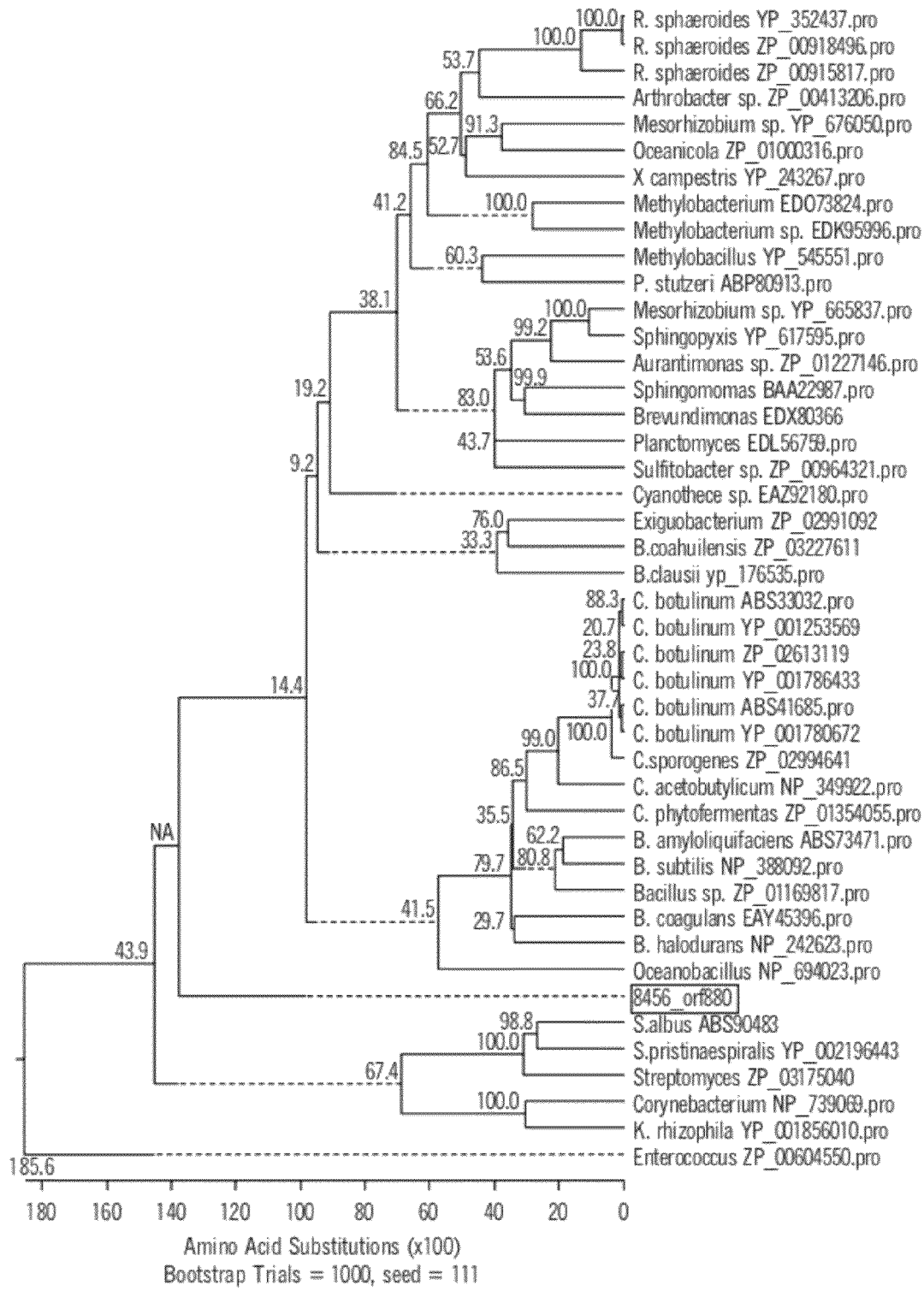
FIG. 9 is a schematic of a bootstrap phylogenetic analysis of 8456_orf880 homologs using ClustalW.

*Jeotgalicoccus* ATCC 8456 ORF880 was identified as one of the two major proteins in a highly purified enzyme fraction that catalyzed the conversion of free fatty acids to α-olefins. The genomic DNA encoding ATCC 8456_orf880 was cloned into pCDF-Duet1 under the control of the T7 promoter, and *E. coli* was transformed with various vectors, as described below. The *E. coli* cells were grown, and the hydrocarbons produced by the cells were analyzed as described in Example 2. When 0.05% stearic acid was fed to cultures of *E. coli* transformed with the 8456_orf880-containing vector, the expression of 8456_orf880 led to the formation of 1-heptadecene in *E. coli* (see FIG. 8, depicting GC/MS traces of α-olefins from *E. coli* either without (black) or with (gray) expression of 8456_orf880). In contrast, adding 0.05% stearic acid to cultures of *E. coli* transformed with a vector control (not containing ATCC— orf880) did not result in the production of 1-heptadecene. This demonstrated that 8456_ORF880 synthesized α-olefins from free fatty acids in an *E. coli* heterologous host. This result indicates that α-olefin biosynthesis can be performed in heterologous organisms. Additionally, when *E. coli* cells expressing 8456_orf880 protein were fed with 0.05% palmitic acid or 0.05% eicosanoic acid, the production of 1-pentadecene or 1-nonadecene, respectively, was observed.

Example 6

Production of α-Olefins from Glucose by Heterologous Expression of *Jeotgalicoccus* ATCC 8456 orf880 in *E. coli* MG1655 ΔfadD Construction of fadD Deletion Strain The fadD gene of *E. coli* MG1655 was deleted using the lambda red system (Datsenko et al., 2000, Proc. Natl. Acad. Sci. USA. 97: 6640-6645) as described below.

The chloramphenicol acetyltransferase gene from pKD3 was amplified with the primers fad1:

(5'-TAACCGGCGTCTGACGACTGACTTAACGCTCAGGCTTTATTGTCCA

CTTTGTGTAGGCTGGAGCTGCTTCG-3'), and fad2:

(5'-CATTTGGGGTTGCGATGACGACGAACACGCATTTTAGAGGTGAAGA

ATTGCATATGAATATCCTCCTTTAGTTCC-3').

Figure 11:
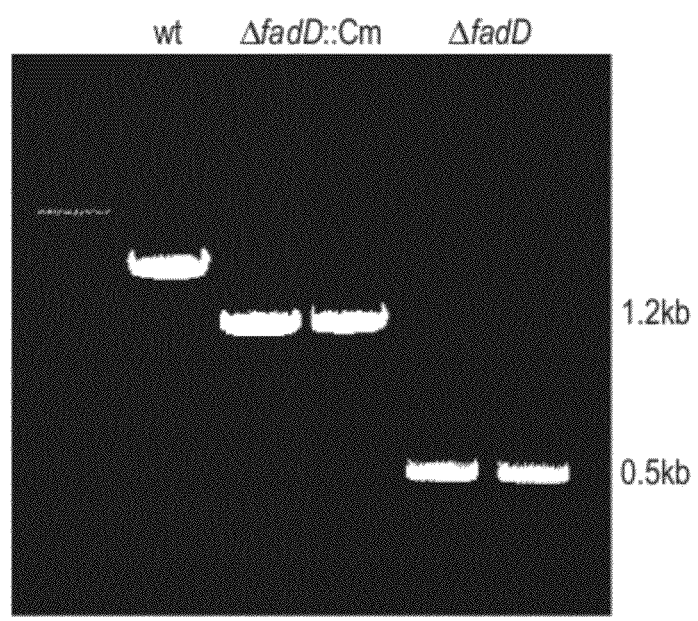
FIG. 11 is a representation of a gel of PCR products from MG1655 wild type cells, ΔfadD::Cm cells, and ΔfadD cells.

This PCR product was electroporated into *E. coli* MG1655 (pKD46). The cells were plated on L-chloramphenicol (30 μg/mL)(L-Cm) and grown overnight at 37° C. Individual colonies were picked on to another L-Cm plate and grown at 42° C. These colonies were then patched to L-Cm and L-carbenicillin (100 mg/mL) (L-Cb) plates and grown at 37° C. overnight. Colonies that were $Cm^R$ and $Cb^S$ were evaluated further by PCR to ensure the PCR product inserted at the correct site. PCR verification was performed on colony lysates of these bacteria using the primers fadF (5'-CGTC-CGTGGTAATCATTTGG-3') and fadR (5'-TCGCAAC-CTTTTCGTTGG-3'). The expected size of the ΔfadD::Cm deletion was about 1200 bp (FIG. 11). The chloramphenicol resistance gene was eliminated using a FLP helper plasmid as described in Datsenko et al. (2000) *Proc. Natl. Acad. Sci. USA.* 97: 6640-6645. PCR verification of the deletion was performed with primers fadF and fadR (FIG. 11). The MG1655 ΔfadD strain was unable to grow on M9+oleate agar plates (oleate as carbon source). It was also unable to grow in M9+oleate liquid media.

Expression of *Jeotgalicoccus* ATCC 8456_orf880 in *E. coli* MG1655 ΔfadD

Figures 12A, 12B:
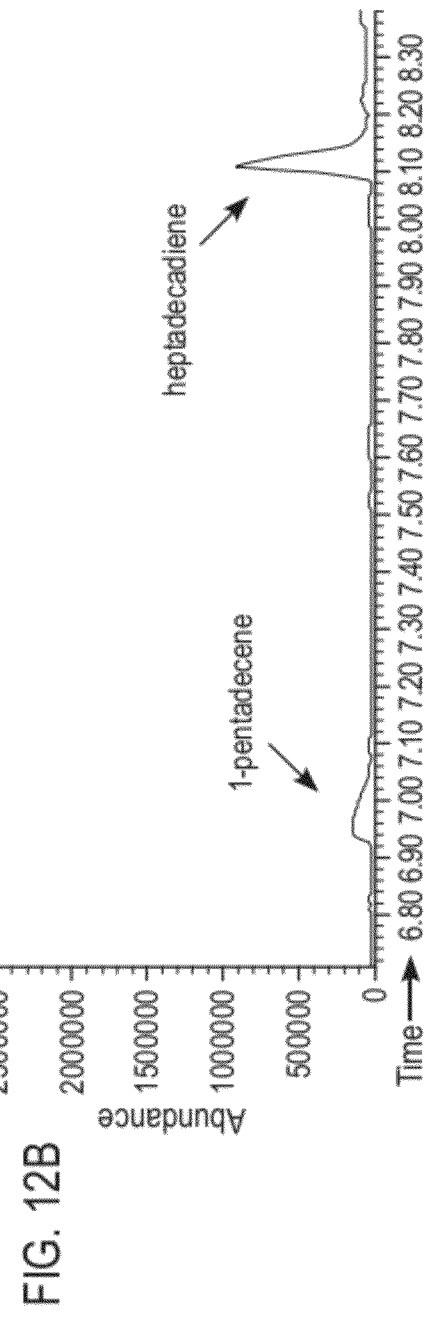
FIG. 12A is a GC/MS trace of α-olefins produced by MG1655 ΔfadD cells transformed with empty vector.
FIG. 12B is a GC/MS trace of α-olefins produced by MG1655 ΔfadD cells transformed with *Jeotgalicoccus* sp. 8456_orf880.

The genomic DNA encoding ATCC 8456_orf880, which was codon-optimized for expression in *E. coli* (SEQ ID NO:4), was cloned into vector OP80 (pCL1920 derivative) under the control of the $P_{trc}$ promoter, and *E. coli* MG1655 ΔfadD was transformed with the resulting vector. The *E. coli* cells were grown at 37° C. in M9 mineral medium supplemented with 20 µg/mL uracil and 100 µg/mL spectinomycin. Glucose (1%, w/v) was the only source of carbon and energy. When the culture reached an $OD_{600}$ of 0.8 to 1.0, IPTG (1 mM) and 0.5 mM delta-aminolaevulinic acid (heme biosynthesis precursor) were added. The temperature was shifted to 25° C. After growth for an additional 18 to 24 h at 25° C., the cells from 10 mL of culture were pelleted, resuspended in 1 mL methanol, sonicated for 30 min, and extracted with 4 mL hexane. After solvent evaporation, the samples were resuspended in 0.1 mL hexane and analyzed by GC-MS. In contrast to the vector-only control, *E. coli* cells transformed with the orf880-bearing vector produced the α-olefins: 1-pentadecene and heptadecadiene (see FIG. 12). This result indicates that expression of orf880 confers on *E. coli* the ability to biosynthesize α-olefins when grown on glucose and that the direct precursors are the most abundant fatty acids in *E. coli*, namely hexadecanoic acid and vaccenic acid (11-cis-octadecenoic acid).

Example 7

Production of α-Olefins in *E. coli* by Heterologous Expression of *Corynebacterium efficiens* YS-134 orfCE2459

Genomic DNA encoding *C. efficiens* YS-134 (DSMZ44549) orfCE2459 (SEQ ID NO:6) was cloned into the NcoI and EcoRI sites of vector OP-80 (pCL1920 derivative) under the control of the $P_{trc}$ promoter. The resulting construct was then transformed into *E. coli* C41 ΔfadE.

The *E. coli* C41 ΔfadE was constructed using primers YafV_NotI and Ivry_O1 to amplify about 830 bp upstream of fadE and primers Lpcaf_ol and LpcaR_Bam to amplify about 960 bp downstream of fadE. Overlap PCR was used to create a construct for in frame deletion of the complete fadE gene. The fadE deletion construct was cloned into the temperature-sensitive plasmid pKOV3, which contained a sacB gene for counterselection, and a chromosomal deletion of fadE was made according to the method of Link et al., *J. Bact.* 179: 6228-6237, 1997. This strain has the acyl-CoA dehydrogenase gene (fadE) deleted, therefore it can not degrade activated fatty acids.

The cells were grown at 37° C. in M9 minimal media supplemented with 20 µg/mL uracil, 1% glucose (w/v), and 100 µg/mL spectinomycin. When the culture reached an $OD_{600}$ of 0.8 to 1.0, it was induced with 1 mM IPTG supplemented with 0.5 mM delta-aminolaevulinic acid (heme biosynthesis precursor), and 0.05% stearic acid (as a substrate for orfCE2459). The temperature was shifted to 25° C. and cells were allowed to grow for an additional 18-20 h Cells from 1 mL of culture were resuspended with 100 µL of methanol, sonicated for 30 min, and extracted with 300 µL of ethyl acetate. After vortexing for 15 min, 300 µL of water was added, and the mixture was vortexed for another 15 min before centrifugation at 15,000 rpm for 10 min. The solvent layer was analyzed by GC-MS.

Figure 13A:
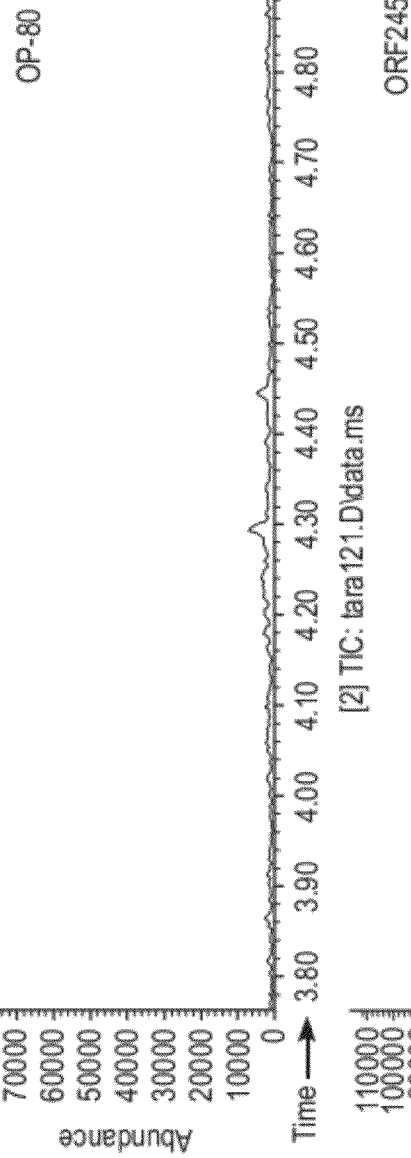
FIGS. 13A, 13B, and 13C are GC/MS traces of α-olefins produced by *E. coli* C41 ΔfadE cells transformed with empty vector (FIG. 13A), *Corynebacterium efficiens* YS-134 orf_CE2459 without stearic acid feeding (FIG. 13B), or with *Corynebacterium efficiens* YS-134 orf_CE2459 with stearic acid feeding (FIG. 13C).
Figure 13B:
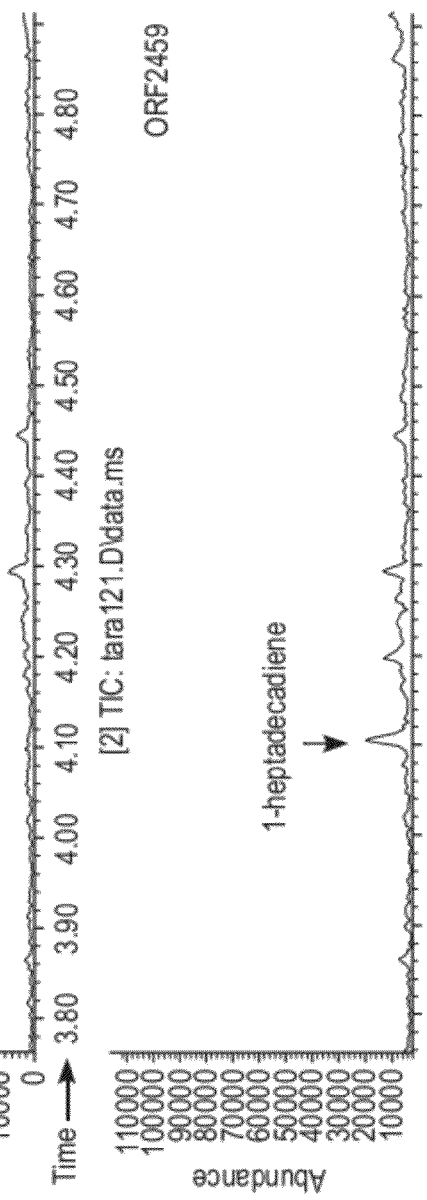
Figure 13C:
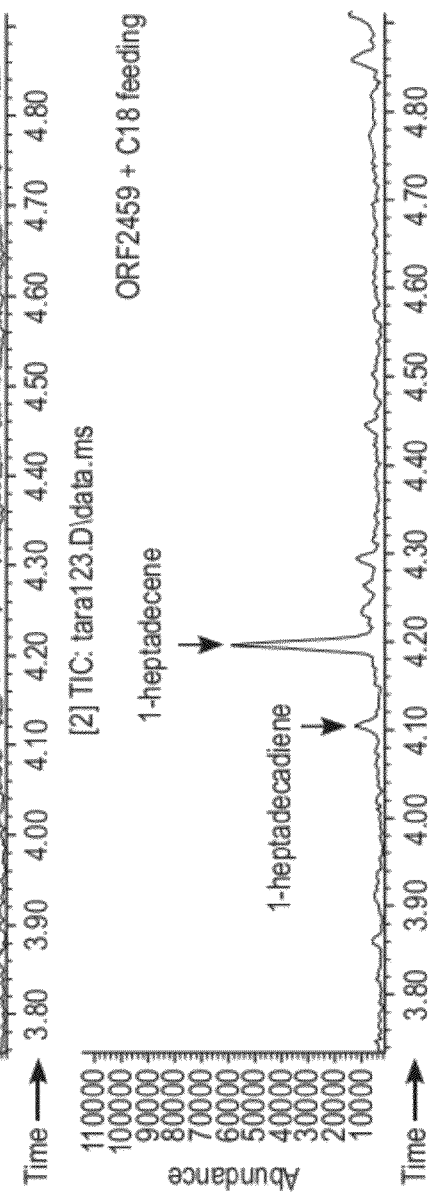
Figure 14A:
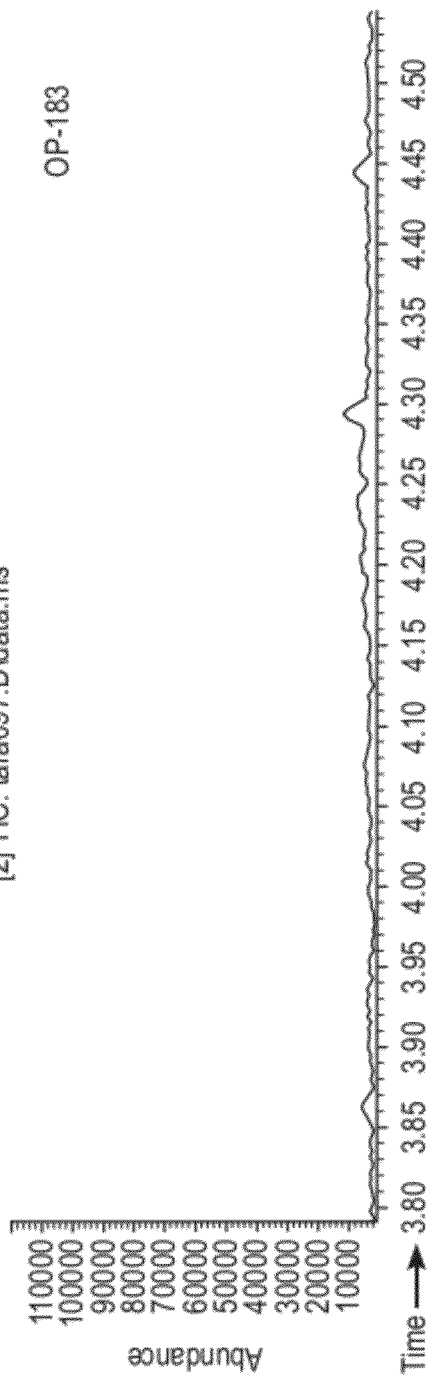
FIGS. 14A, 14B, 14C, and 14D are GC/MS traces of α-olefins produced by *E. coli* C41 ΔfadE cells transformed with empty vector (FIG. 14A), empty vector with stearic acid feeding (FIG. 14B), *Kokuria rhizopila* DC2201 orf_KRH21570 without stearic acid feeding (FIG. 14C), or with *Kokuria rhizopila* DC2201 orf_KRH21570 with stearic acid feeding (FIG. 14D).
Figure 14B:
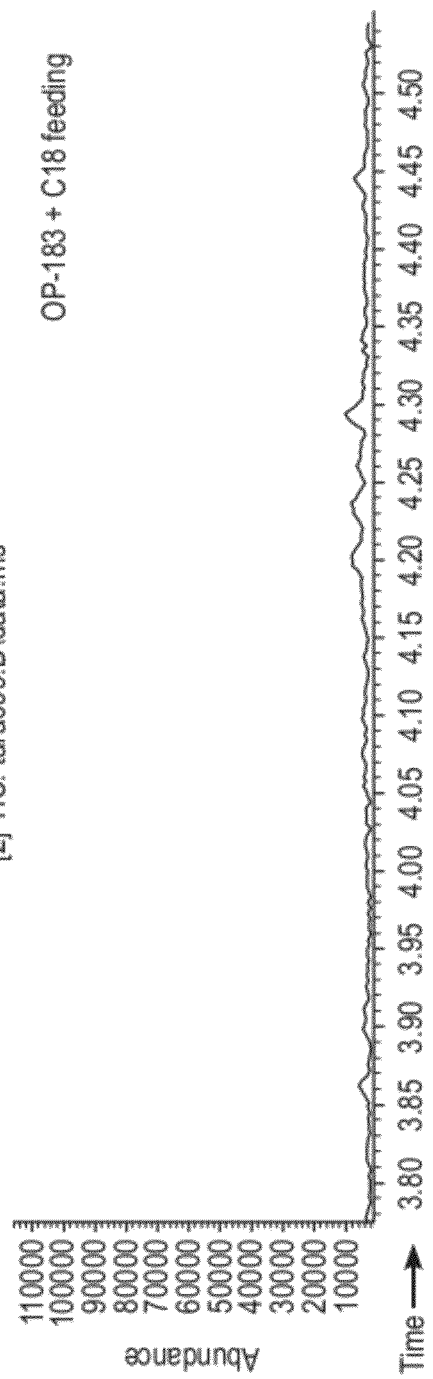
Figure 14C:
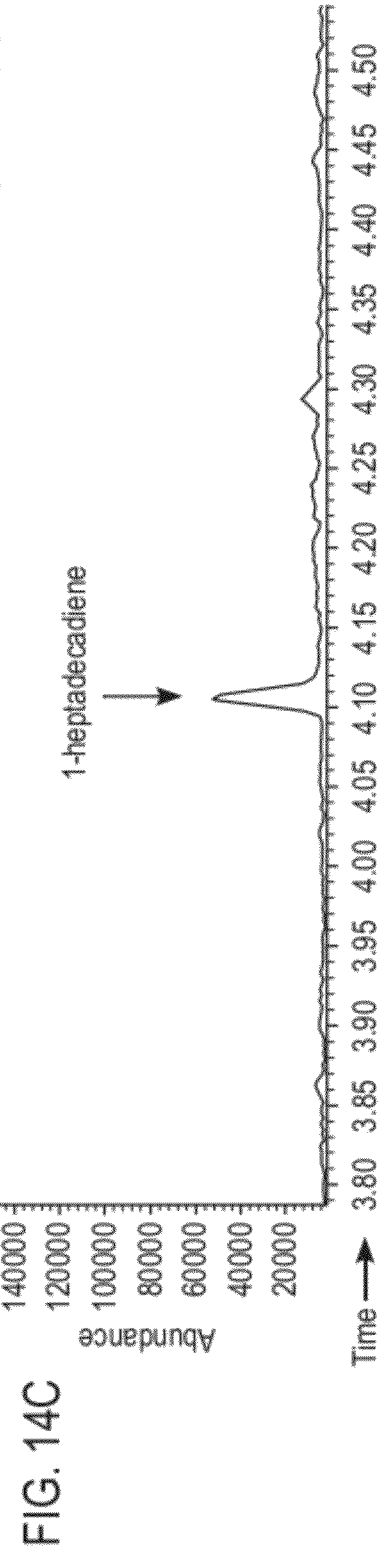
Figure 14D:
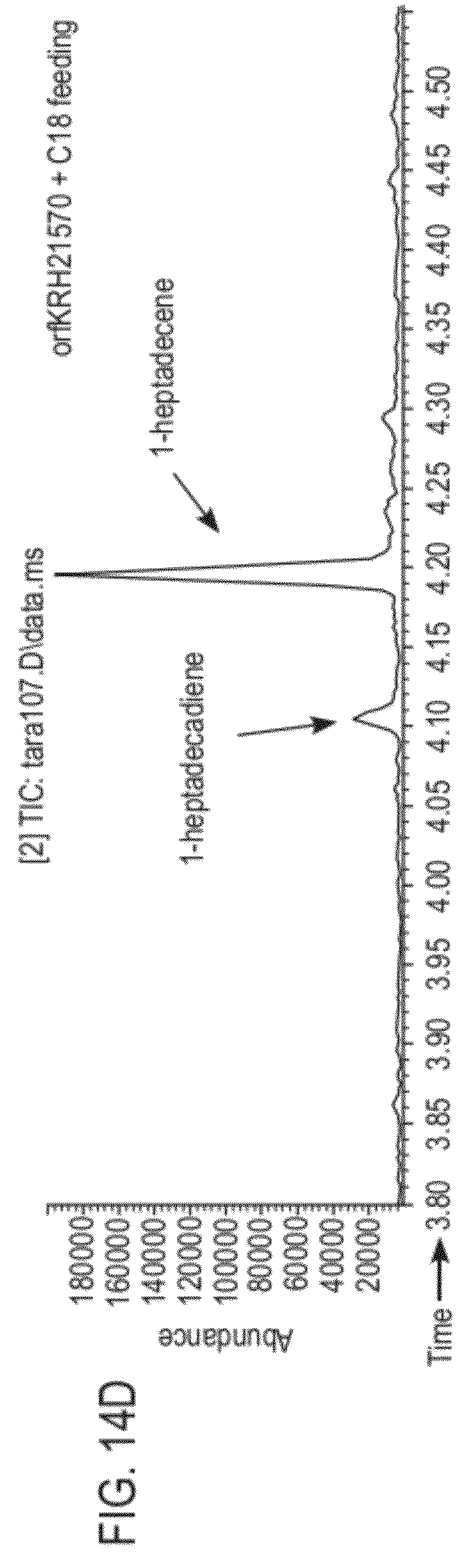

As shown in FIG. 13, *E. coli* cells transformed with an orfCE2459-bearing vector produced 1-heptadecadiene without stearic acid feeding and produced 1-heptadecene with stearic acid feeding. This result indicates that expression of orfCE2459 confers on *E. coli* the ability to biosynthesize α-olefins (e.g., 1-heptadecadiene) when grown on glucose (FIG. 13B) and that orfCE2459 can convert fed fatty acids, such as stearic acid, into α-olefins, such as 1-heptadecene (FIG. 13C).

Example 8

Production of α-Olefins in *E. coli* by Heterologous Expression of *Kokuria rhizophila* orfKRH21570

Genomic DNA encoding *Kokuria rhizophila* DC2201 orfKRH21570 (SEQ ID NO:8), which was codon optimized (SEQ ID NO:9) for expression in *E. coli*, was cloned into the NdeI and XhoI sites of vector OP-183 (pACYC177 derivative) under the control of the $P_{trc}$ promoter. The resulting construct was then transformed into *E. coli* C41 ΔfadE. The cells were grown, extracted, and analyzed as in described in Example 7.

As shown in FIG. 14, *E. coli* cells transformed with codon optimized orfKRH21570-bearing vector produced 1-heptadecadiene without stearic acid feeding and produced 1-heptadecene with stearic acid feeding. This result indicates that expression of orfKRH21570 confers on *E. coli* the ability to biosynthesize α-olefins (e.g., 1-heptadecadiene) when grown on glucose (FIG. 14C) and that orfKRH21570 can convert fed fatty acids, such as stearic acid, into α-olefins, such as 1-heptadecene (FIG. 14D).

Example 9

Production of α-Olefins in *Bacillus subtilis* by Heterologous Expression of *Jeotgalicoccus* sp. ATCC8456 orf880

Genomic DNA encoding *Jeotgalicoccus* ATCC 8456_orf880 was cloned into the BamHI and XbaI sites of vector pHT01 under the control of the $P_{grac}$ promoter. *B. subtilis* IHA01 (lacA::spec leuB8 metB5 r(−)m(+) Sp, obtained from *Bacillus* Genetic Stock Center, Columbus, Ohio, strain number BGSC 1A785) was transformed with the resulting vector. The *B. subtilis* cells were grown at 37° C. in minimal medium supplemented with 2% glucose, 0.3 mM leucine, 0.3 mM methionine, and 10 mg/L chloramphenicol. When the cultures reached an $OD_{600}$ of 0.8 to 1.0, 1 mM IPTG was added (to induce expression of orf880) along with 0.5 mM 5-amino laevulinic acid (as a precursor for heme biosynthesis) and 0.05% stearic acid (as a substrate for ORF880). The temperature was shifted to 25° C. and after growth for additional 18-24 h at 25° C., cells from a 1 mL culture were pelleted, resuspended in 100 µL methanol, sonicated for 1 h, and extracted with 300 µL ethyl acetate. 300 µL of water was added before separating the organic layer by centrifugation at 15,000 rpm for 5 min. The solvent layer was analyzed by GC-MS.

In contrast to cells transformed with the vector only control, *B. subtilis* cells transformed with *Jeotgalicoccus* sp. ATCC8456 orf880-bearing vector produced 1-heptadecene from stearic acid (see FIG. 15B). This example demonstrates that in *B. subtilis* fatty acids, such as stearic acid, can be converted to α-olefins by heterologous expression of *Jeotgalicoccus* ATCC 8456_orf880 in *Bacillus subtilis*.

Example 10

Production of α-Olefins in *Bacillus subtilis* by Heterologous Expression of *Corynebacterium efficiens* YS-134 orfCE2459

Genomic DNA encoding *Corynebacterium efficiens* YS-134 orfCE2459 was cloned into the BamHI and XbaI sites of vector pHT01 under the control of the $P_{grac}$ promoter and transformed into *B. subtilis* IHA01 cells. The resulting cells were grown, extracted, and analyzed as described in Example 9.

Figure 15A:
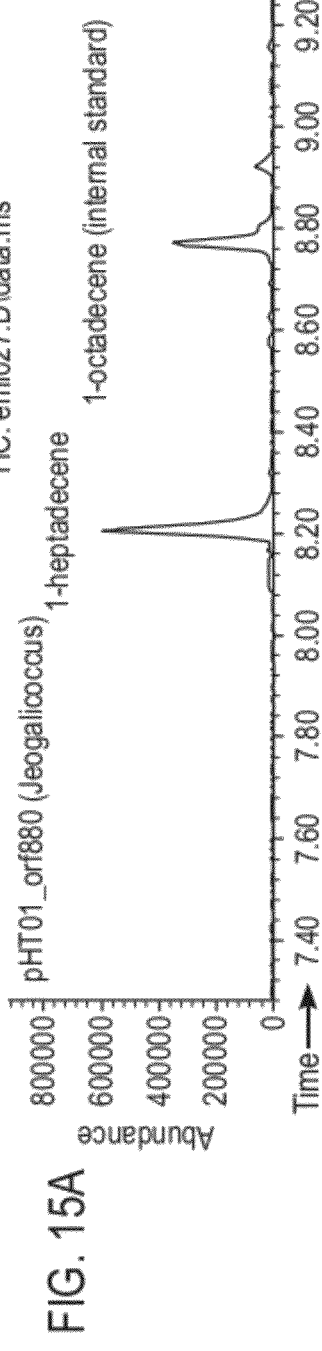
FIGS. 15A, 15B, and 15C are GC/MS traces of α-olefins produced by *B. subtilis* cells transformed with *Jeotgalicoccus* sp. ATCC8456_orf880 (FIG. 15A), *C. efficiens* YS-134 orf_CE2459 (FIG. 15B), or empty vector (FIG. 15C).
Figure 15B:
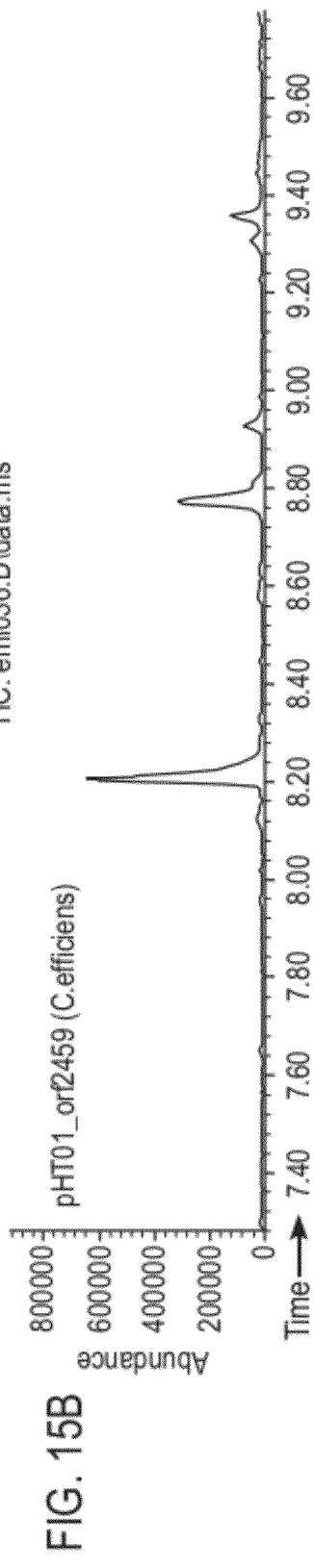
Figure 15C:
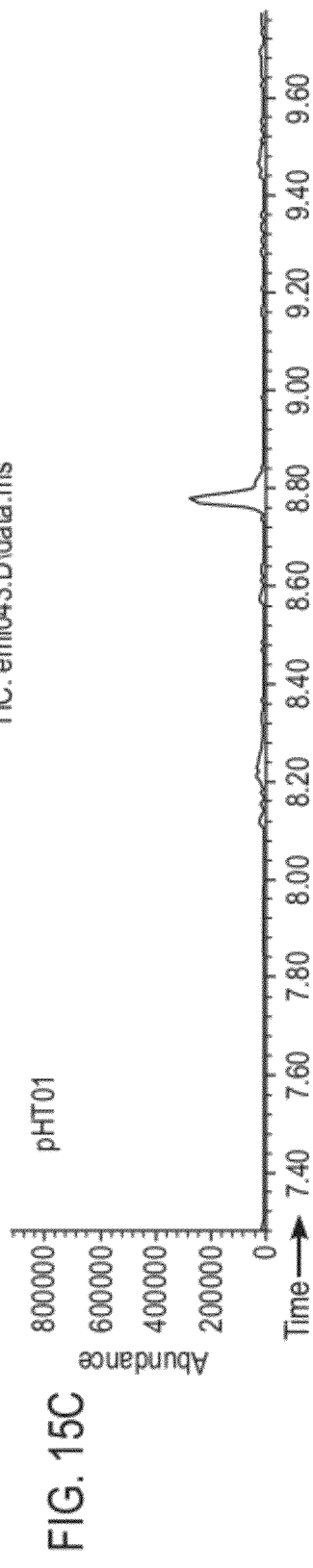
Figure 16:
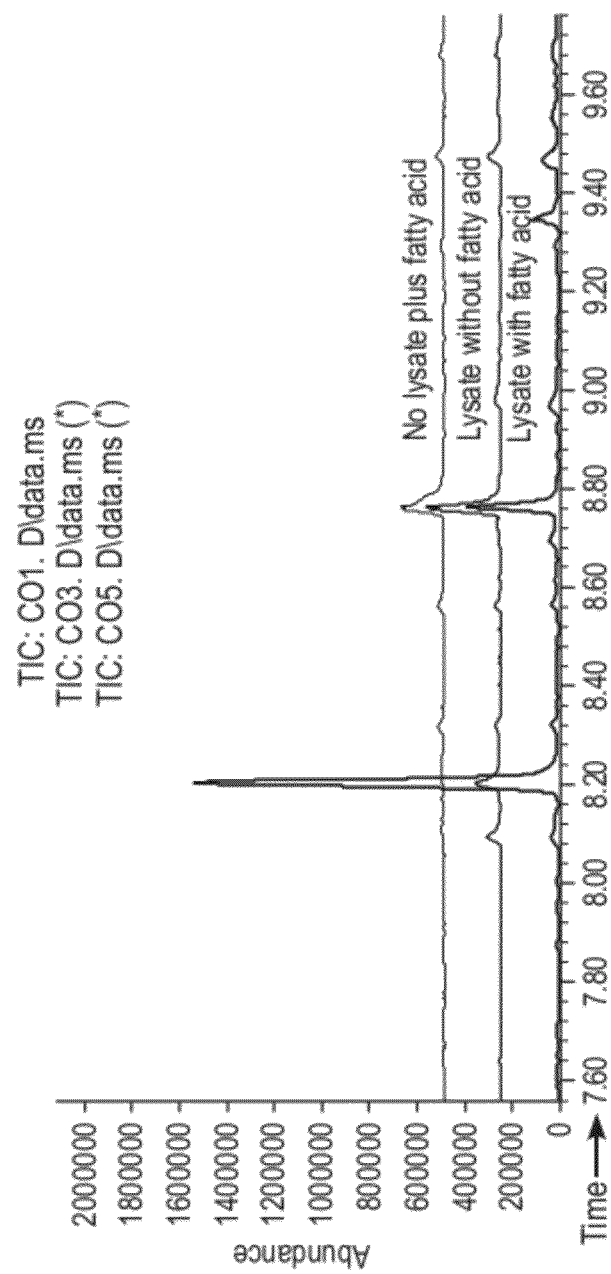
FIG. 16 is a set of GC/MS traces of α-olefins produced in vitro by *Corynebacterium efficiens* ORF_CE2459.

In contrast to cells transformed with the vector only control, *B. subtilis* cells transformed with *Corynebacterium efficiens* YS-134 orf_CE2459-bearing vector produced 1-heptadecene from stearic acid (see FIG. 15). This demonstrates that in *B. subtilis* fatty acids, such as stearic acid, can be converted to α-olefins by heterologous expression of *C. efficiens* orf_CE2459.

Example 11

Production of α-Olefins in *Saccharomyces cerevisiae* by Heterologous Expression of *Jeotgalicoccus* sp. ATCC8456 orf880

Genomic DNA encoding *Jeotgalicoccus* sp. ATCC 8456_orf880 is cloned into the ApaI and XhoI sites of the yeast expression vector pESC-His. *S. cerevisiae* (BY4741) yeast cells are then transformed with either a plasmid containing orf880 or a plasmid not containing orf880. The transformed yeast cells are cultured under suitable conditions to allow expression of ORF880. The cells are pelleted and then lysed using YeastBuster™ (Novagen, Madison, Wis.). The α-olefins are extracted and analyzed as described in Examples 6 and 7.

*Jeotgalicoccus* sp. ATCC8456_orf880 expressed in *S. cerevisiae* produces α-olefins. Similar methods are used to express *Jeotgalicoccus* sp. ATCC8456_orf880 in any cell of interest, after which cell lysates are prepared and the production of α-olefins analyzed.

Example 12

In Vitro Synthesis of α-Olefins by *Jeotgalicoccus* sp. ATCC8456 orf880 Heterologously Expressed in and Purified from *E. coli*

Expression and Purification of *Jeotgalicoccus* sp. ATCC8456_orf880

The genomic DNA encoding *Jeotgalicoccus* sp. ATCC8456_orf880 was cloned into the NdeI and XhoI sites of vector pET15b (Novagen) under the control of the T7 promoter for expression in and purification from *E. coli*. This plasmid expressed an N-terminal His-tagged version of 8456_orf880.

An *E. coli* BL21 strain (DE3) (Invitrogen) was transformed with pET15b-orf880 using routine chemical transformation techniques. Protein expression was carried out by first inoculating a colony of the *E. coli* strain in 5 mL of LB media supplemented with 100 mg/L of carbenecillin and shaken overnight at 37° C. to produce a starter culture. This starter culture was used to inoculate 1 L of LB media supplemented with 100 mg/L of carbenecillin. The culture was shaken at 37° C. until an $OD_{600}$ value of 0.6 was reached. The culture was placed on ice for 10 min before IPTG was added to a final concentration of 250 µM. The culture was then shaken at 18° C. for approximately 18 h. The culture was then centrifuged at 3,700 rpm for 20 min at 4° C. The pellet was then resuspended in 30 mL of buffer containing 100 mM sodium phosphate buffer at pH 7.2 supplemented with Bacterial ProteaseArrest (GBiosciences). The cells were then sonicated at 12 W on ice for 9 sec with 1.5 sec of sonication followed by 1.5 sec of rest. This procedure was repeated 5 times with one min intervals between each sonication cycle. The cell free extract was centrifuged at 10,000 rpm for 30 min at 4° C. 5 mL of Ni-NTA (Qiagen) was added to the supernatant and the mixture was gently stirred at 4° C. The slurry was passed over a column removing the resin from the lysate. The resin was then washed with 30 mL of buffer containing 100 mM sodium phosphate buffer at pH 7.2 plus 30 mM imidazole. Finally, the protein was eluted with 15 mL of 100 mM sodium phosphate buffer at pH 7.2 plus 250 mM imidazole. The protein solution was dialyzed with 200 volumes of 100 mM sodium phosphate buffer at pH 7.2. Protein concentration was determined using the Bradford assay (Biorad). 125 µg/mL of protein was obtained.

In Vitro Synthesis of α-Olefins from Fatty Acid Substrates

In order to assay the in vitro fatty acid substrate specificity of ORF880, potassium salts of the following fatty acids were prepared: tetradecanoic acid, hexadecanoic acid, octadecanoic acid, eicosanoic acid, and behenic acid (Sigma). The fatty acid solutions were made with 2% ethanol and 2% Tergitol solution (Sigma, St. Louis, Mo.) to a final concentration of 20 mM.

The kinetics of the decarboxylation reaction was determined using potassium octadecanoate. A 200 µL reaction was prepared with the following reactant concentrations: 1.25 µM of ORF880, 200 µM of potassium octadecanoate, 200 µL dithiothreitol, and 100 mM sodium phosphate buffer at pH 7.2. The reactions were incubated at room temperature and time points were taken in duplicate between 5 min and 120 min. Reactions were quenched and extracted by adding 100 µL of ethyl acetate containing 1-octadecene at 5 mg/L as an internal reference. Samples were analyzed using GC/MS using the alkane-1 splitless method, which is performed using the following parameters: run time: 20 min; column: HP-5-MS Part No. 19091S-433E (length of 30 meters; I.D.: 0.25 mm narrowbore; film: 0.25 µM); sample: standard ethyl acetate extraction; inject: 1 µL Agilent 6850 inlet; inlet: 300° C. splitless; carrier gas: helium; flow: 1.3 mL/min; oven temp: 100° C. hold 5 min, 320 at 20° C./min, 320 hold 5 min; det: Agilent 5975B VL MSD; det. temp: 300° C.; scan: 50-500 M/Z. Calibration curves were generated using 1-heptadecene dissolved in ethyl acetate. Based upon this analysis, the product production was determined to be linear from 5 min to 60 min.

To assay the reaction rates of different fatty acid substrates, the following reactions were prepared at 200 µL scales: 1.0 µM ORF880 enzyme, 200 µM of a test fatty acid salt, 200 µL dithiothreitol, and 100 mM sodium phosphate buffer at pH 7.2. The reactions were carried out at room temperature and time points were taken in triplicate at 20 min and 47 min using the extraction and analysis procedure described above. Reference curves were generated using available chemical standards. In some instances, the chemical standards were not available (for example, cis-9-heneicosene was used as a reference for 1-heneicosene and 9-tricosene was used as a reference for 1-tricosene). Activities were calculated by taking the difference between the average α-olefin concentrations for each substrate at 47 min and 20 min and then dividing the difference by 27 min. The results are summarized in Table 7.

TABLE 7

Activity of ORF880 with different fatty acid substrates

| Substrate | Activity (nM alkene produced/min) |
|---|---|
| tetradecanoic acid | 22.9 |
| hexadecanoic acid | 181.9 |
| octadecanoic acid | 77.2 |
| eicosanoic acid | 19.7 |
| behenic acid | 30.6 |

These results demonstrate that heterologously expressed ORF880 was able to convert various fatty acid substrates to α-olefins in vitro. The data also show that ORF880 had highest activity when hexadecanoic acid was the fatty acid substrate.

Example 13

In Vitro Synthesis of α-Olefins by *Corynebacterium efficiens* YS-134 orfCE2459 Heterologously Expressed in *E. coli*

An *E. coli* BL21 strain (DE3) (Invitrogen) was transformed with pET15-orf CE2459 using routine transformation techniques. Protein expression was carried out by first inoculating a colony of the *E. coli* strain in 5 mL of LB media supplemented with 100 mg/L of carbenecillin and then shaking overnight at 37° C. to produce a starter culture. This starter culture was used to inoculate 0.5 L of LB media supplemented with 100 mg/L of carbenecillin. The culture was shaken at 37° C. until an $OD_{600}$ value of 0.6 was reached. The culture was placed on ice for 10 min before IPTG was added to a final concentration of 250 µM. δ-Aminolevulinic acid was also added to a final concentration of 0.5 mM. The culture was then shaken at 25° C. for approximately 18 h. The culture was then centrifuged at 3,700 rpm for 20 min at 4° C. The pellet was then resuspended in 7 mL of buffer containing 100 mM sodium phosphate buffer at pH 7.2 supplemented with Bacterial ProteaseArrest (GBiosciences). The cells were then sonicated at 12 W on ice for 9 sec with 1.5 sec of sonication followed by 1.5 sec of rest. This procedure was repeated 4 times with one min intervals between each sonication cycle. The cell free extract was centrifuged at 10,000 rpm for 30 min at 4° C.

To assay the activity of ORF CE2459, 200 µL of lysate was incubated with 200 µM of hydrogen peroxide and 200 µM of potassium octadecanoate. As a negative control, the same reaction was set up, but without the addition of either cell lysate (100 mM sodium phosphate pH 7.2 was used in its place) or free fatty acid. The reactions were incubated at room temperature overnight. The reactions were then extracted with 100 µL of ethyl acetate with 1-octadecene added at 5 mg/L as an internal standard. Samples were analyzed using GC/MS using the alkane-1 splitless method which was performed using the following parameters: run time: 20 min; column: HP-5-MS Part No. 19091S-433E (length of 30 meters; I.D.: 0.25 mm narrowbore; film: 0.25 µM); sample: standard ethyl acetate extraction; inject: 1 µL Agilent 6850 inlet; inlet: 300° C. splitless; carrier gas: helium; flow: 1.3 mL/min; oven temp: 100° C. hold 5 min, 320 at 20° C./min, 320 hold 5 min; det: Agilent 5975B VL MSD; det. temp: 300° C.; scan: 50-500 M/Z.

As shown in FIG. 17, an *E. coli* lysate expressing orfCE2459 was capable of converting octadecanoic acid into 1-heptadecene. The peak at 5.20 min corresponds to 1-heptadecene and the peak at 8.76 is the internal standard 1-octadecene. Peak identification was determined by comparing the retention time and the MS fragmentation pattern with authentic references from Sigma. This result demonstrates that ORF CE2459 exhibits similar in vitro fatty acid decarboxylase activity as ORF880.

Example 14

In Vitro Synthesis of α-Olefins by *Kokuria rhizophila* orf_KRH21570 Heterologously Expressed in and Purified from *E. coli*

The genomic DNA encoding *Kokuria rhizophila* orf_KRH21570 was cloned into the NdeI and XhoI sites of vector pET15b (Novagen) under the control of the T7 promoter for expression in and purification from *E. coli*. This plasmid expressed an N-terminal His-tagged

*E. coli* C41 DE3 (ΔfadE) cells were transformed with pET15b-orfKRH21570 using routine transformation techniques. Protein expression was carried out by first inoculating 5 mL of LB broth supplemented with 100 mg/L carbenicillin with a colony of the *E. coli* strain which was followed by shaking the cells overnight at 37° C. to produce a starter culture. This starter culture was used to inoculate 0.5 L of LB media supplemented with 100 mg/L of carbenicillin. The culture was shaken at 37° C. until an $OD_{600}$ value of 0.6 was reached, after which it was induced with 1 mM IPTG and 0.5 mM delta-aminolaevulinic acid. The culture was then shaken at 25° C. for approximately 18 h. The protein was purified as described in Example 12.

To assay the activity of ORF_KRH21570, 200 µL of purified protein was incubated with 200 µM of hydrogen peroxide and 200 µM of potassium hexadecanoate. As a negative control, the same reaction was conducted, but without the addition of either purified protein (100 mM sodium phosphate pH 7.2 was used in its place) or free fatty acid. The reactions were performed in duplicates and incubated at room temperature overnight. The reactions were then extracted with 100 µL of ethyl acetate with 1-octadecene added at 5 mg/L as an internal standard. Trimethylanilinium hydroxide was added to the ethyl acetate layer at a 1:1 ratio and the extracts analyzed by GC/MS using the MAR_splitless_short method. The parameters used were as follows: 9.50 min; column: DB5-ht Part No. J&W 122-5711 (length of 15 meters; I.D.: 0.25 mm narrowbore; film: 0.10 µM); sample: standard ethyl acetate extraction; inject: 1 µL Agilent 6850 inlet; inlet: 300 C splitless; carrier gas: helium; flow: 1.3 mL/min; oven temp: 80° C. hold 1.0 min, 320 at 30° C./min, 320 hold 0.5 min; det: Agilent 5975B VL MSD; E1 mode; det. temp: 230° C.; scan: 50-330 M/Z.

Figures 18A, 18B, 18C:
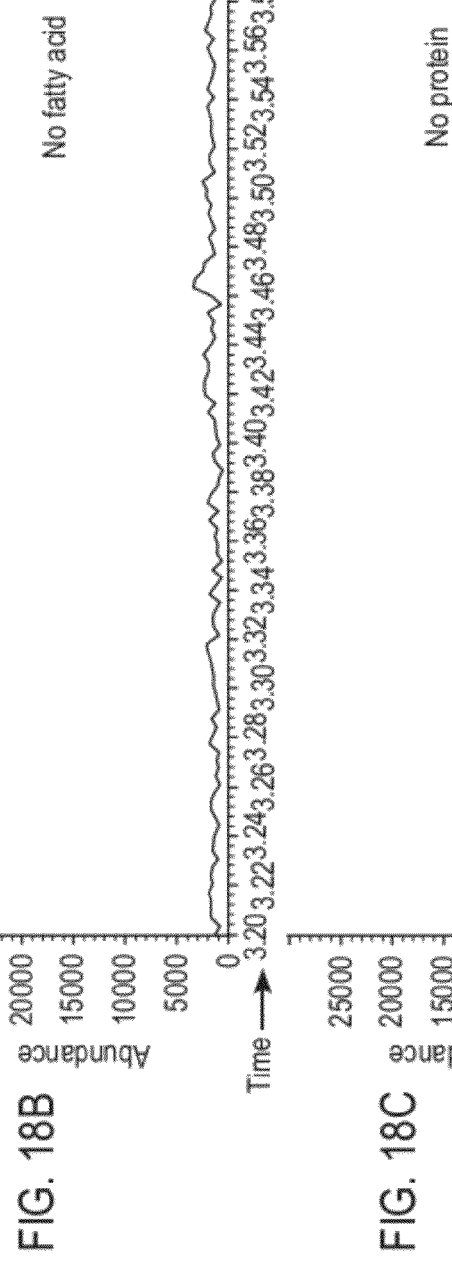
FIGS. 18A, 18B, and 18C are GC/MS traces of α-olefins produced in vitro by purified *Methylobacterium populi* orf_Mpop1292 with hexadecanoic acid as substrate (FIG. 18A), by purified *Methylobacterium populi* orf_Mpop1292 with no substrate (FIG. 18B), and with no enzyme (FIG. 18C).

As shown in FIG. 18, *Kokuria rhizophila* ORF_KRH21570 was capable of converting hexadecanoic acid to 1-pentadecene in vitro.

Example 15

In Vitro Synthesis of α-Olefins by *Methylobacterium populi* orf_Mpop1292 Heterologously Expressed in and Purified from *E. coli*

The genomic DNA encoding *Methylobacterium populi* orf_Mpop1292 (SEQ ID NO:11) was cloned into the NdeI and XhoI sites of vector pET15b (Novagen) under the control of the T7 promoter for expression in and purification from *E. coli*. This plasmid expressed an N-terminal His-tagged version of orf_KRH21570.

*E. coli* C41 DE3 (ΔfadE) cells were transformed with pET15b-orf_Mpop1292 using routine transformation techniques. Protein expression was carried out by first inoculating 5 mL of LB broth supplemented with 100 mg/L carbenicillin with a colony of the *E. coli* strain, and then shaking the cells overnight at 37° C. to produce a starter culture. This starter culture was used to inoculate 0.5 L of LB media supplemented with 100 mg/L of carbenicillin. The culture was shaken at 37° C. until an $OD_{600}$ value of 0.6 was reached, after which it was induced with 1 mM IPTG and 0.5 mM delta-aminolaevulinic acid. The culture was then shaken at 25° C. for about 18 h. The protein was purified as described in Example 12 and assayed as described in Example 14.

Figure 19:
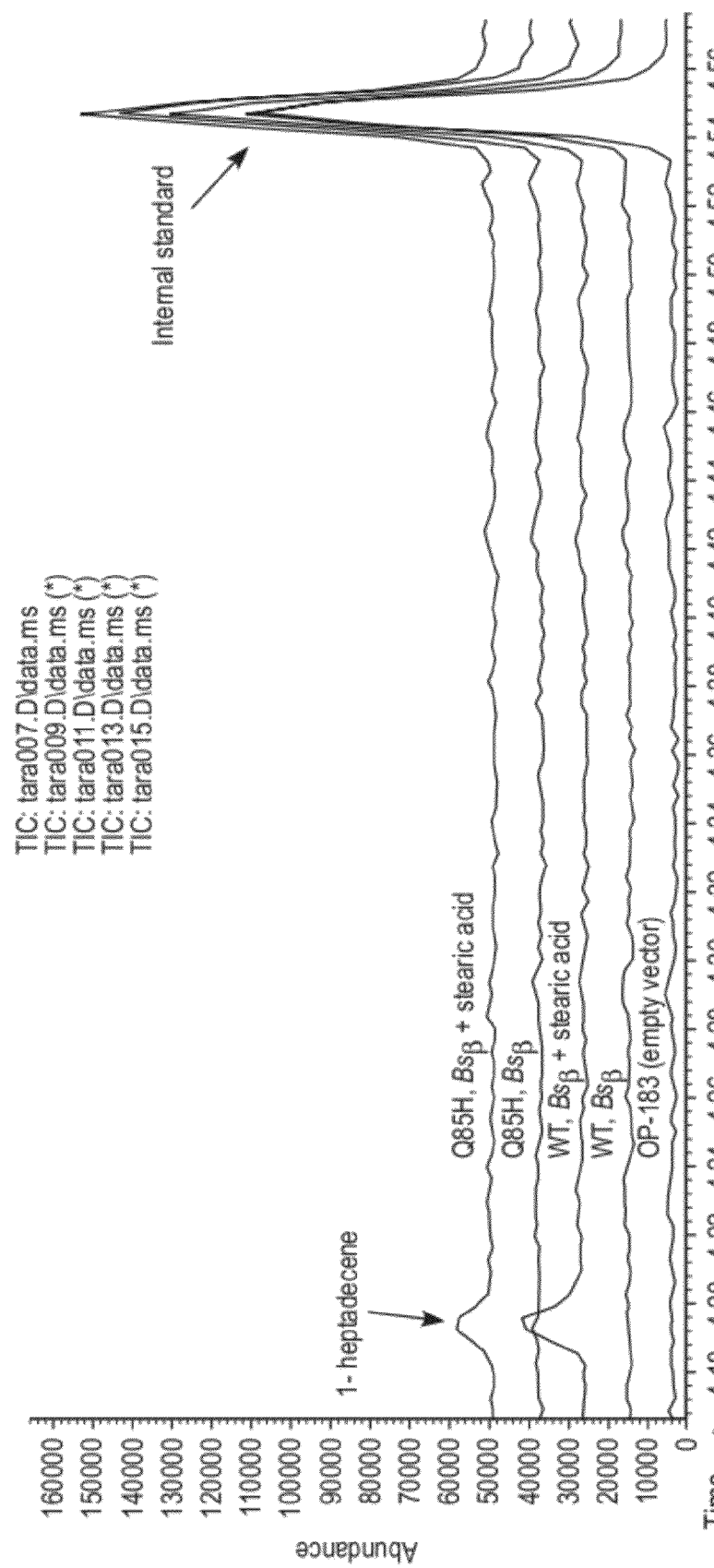
FIG. 19 is a set of GC/MS traces of α-olefins produced by *E. coli* cells transformed with *Bacillus subtilis* P450$_{BSβ}$ or empty vector.

As shown in FIG. 19, *Methylobacterium populi* ORF_Mpop1292 was capable of converting hexadecanoic acid to 1-pentadecene in vitro.

Example 16

Production of α-Olefins in *E. coli* Through Heterologous Expression of *Bacillus subtilis* Fatty Acid Hydroxylase, $P450_{Bsβ}$ The genomic DNA encoding *Bacillus subtilis* fatty acid hydroxylase, Cyp152A1 (SEQ ID NO:13) or $P450_{Bsβ}$, was cloned into the NdeI and XhoI sites of vector OP-183 (pACYC177 derivative) under the control of the $P_{trc}$ promoter. The construct was used as a template to introduce a mutation at position 85 changing the Glu to His using the following primer: GTTAATGCGATTCAcGGAATGGATGGC. The resulting constructs were then transformed into *E. coli* C41 (ΔfadE). The cells were grown at 37° C. in M9 minimal media supplemented with 20 µg/mL uracil, 1% glucose (w/v), and 100 µg/mL carbenicillin. When the culture reached $OD_{600}$ of 0.8-1.0, it was induced with 1 mM IPTG; supplemented with 0.5 mM delta-aminolaevulinic acid (heme biosynthesis precursor) and 0.05% stearic acid (as a substrate for $Bs_b$). The temperature was shifted down to 25° C. and cells were allowed to grow for an additional 18-20 h. Cells from 1 mL of culture was resuspended with 100 µL of methanol, sonicated for 30 min, and extracted with 300 µL of ethyl acetate. After vortexing the extract for 15 min, 300 µL of water was added, vortexed for another 15 minutes before centrifugation at 15,000 rpm for 10 minutes. The solvent layer was analyzed by GC-MS.

Figure 20:
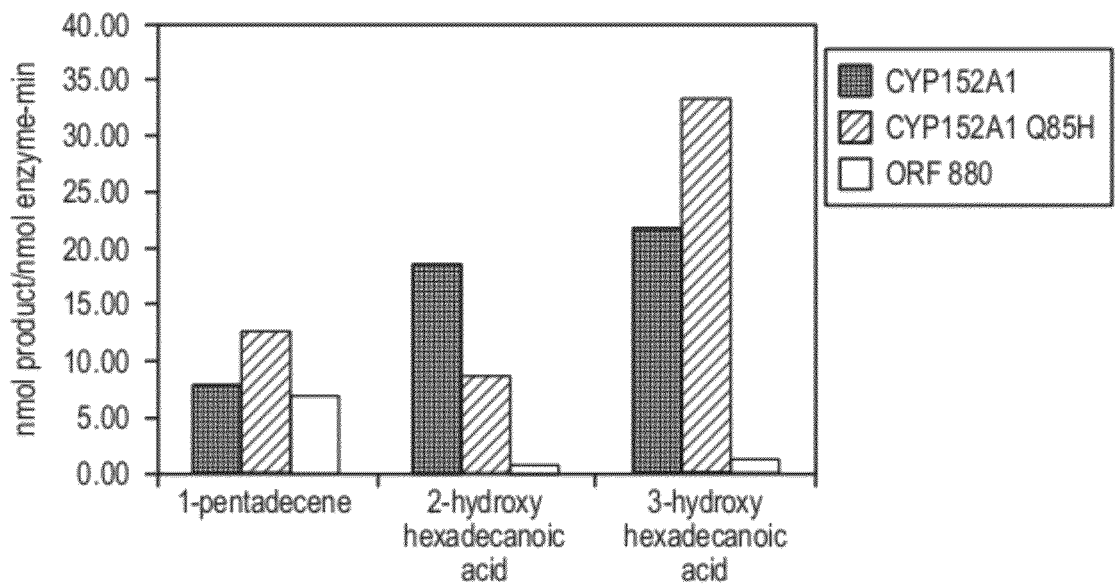
FIG. 20 is a graph demonstrating the specific activity of 1-pentadecene and α(2)- and β(3)-hydroxy hexadecanoic acid production for ORF880, CYP152A1, and CYP152A1 Q85H using hexadecanoic acid as a substrate.

As shown in FIG. 20, *E. coli* cells transformed with *Bacillus subtilis* $P450_{Bsβ}$-bearing vectors produced 1-heptadecene with stearic acid feeding. This result indicates that *Bacillus subtilis* $P450_{Bsβ}$ can convert fed fatty acids, such as stearic acid, into α-olefins, such as 1-heptadecene (FIG. 20). Both the wildtype protein and the Gln85-His-mutant protein were capable of carrying out this reaction.

Example 17

Specific Activity of α-Olefin Production and α and β Hydroxy Fatty Acid Production Using ORF880, CYP152A1 ($P450_{Bsβ}$), and CYP152A1 Q85H The specific activity of α-olefin formation as well as α-(2) and β-(3)hydroxy fatty acid formation were determined for ORF880, CYP152A1, and CYP152A1 Q85H (see Examples 12 and 16). An *E. coli* BL21 strain (DE3) (Invitrogen) was transformed with either pET15b-orf 880, pET15b-cyp152A1, and pET15b-cyp152A1 Q85H using routine chemical transformation techniques. Protein expression was carried out by first inoculating a colony of the *E. coli* strain in 5 mL of LB media supplemented with 100 mg/L of carbenicillin and shaken overnight at 37° C. to produce a starter culture. This starter culture was used to inoculate 0.5 L of LB media supplemented with 100 mg/L of carbenicillin. The culture was shaken at 37° C. until an $OD_{600}$ value of 0.6 was reached. The culture was placed on ice for 10 min before IPTG was added to a final concentration of 250 µM. The culture was shaken at 25° C. for approximately 18 h, and then centrifuged at 3,700 rpm for 20 min at 4° C. The pellet was then resuspended in 10 mL of buffer containing 100 mM sodium phosphate buffer at pH 7.2 supplemented with Bacterial ProteaseArrest (GBiosciences). The cells were then sonicated at 12 W on ice for 9 sec with 1.5 sec of sonication followed by 1.5 sec of rest. This procedure was repeated 5 times with one min intervals between each sonication cycle. The cell free extract was centrifuged at 10,000 rpm for 30 min at 4° C. 5 mL of Ni-NTA (Qiagen) was added to the supernatant, and the mixture was gently stirred at 4° C. The slurry was passed over a column removing the resin from the lysate. The resin was then washed with 30 mL of buffer containing 100 mM sodium phosphate buffer at pH 7.2 plus 30 mM imidazole. Finally, the protein was eluted with 15 mL of 100 mM sodium phosphate buffer at pH 7.2 plus 250 mM imidazole. The protein solution was dialyzed with 200 volumes of 100 mM sodium phosphate buffer at pH 7.2 with 20% glycerol. Protein concentration was determined using the Bradford assay (Biorad). 578 µg/mL of ORF880, 865 µg/mL of CYP152A1, and 653 µg/mL of CYP152A1 Q85H protein was obtained.

To determine the specific activity with potassium hexadecanoate, the following reactions were set-up where each time point consisted of 500 µL. Each reaction contained of 500 µM $H_2O_2$, 200 µM of potassium hexadecanoate, 100 mM sodium phosphate buffer at pH 7.2, and protein at the following concentrations: ORF880-0.23 or 0.46 µM; CYP152A1-8.65, 17.3, or 34.6 µM; CYP152A1 Q85H-6.53, 13.06, or 26.12 µM. The reactions were carried out at room temperature and time points were taken at 0, 1, 3, 5, 7, 10, 14, and 20 minutes. Reactions were quenched with 50 µL of 12 M HCl and then extracted with 200 µL of ethyl acetate. 50 µL of this extract was then reacted with 50 µL N,O-Bis(trimethylsilyl)trifluoroacetamide with trimethyl-chlorosilane (Aldrich). Samples were analyzed using GC/MS using the following parameters: run time: 20 min; column: HP-5-MS Part No. 190915-433E (length of 30 meters; I.D.: 0.25 mm narrowbore; film: 0.25 µM); inject: 1 µL Agilent 6850 inlet; inlet: 300° C. splitless; carrier gas: helium; flow: 1.3 mL/min; oven temp: 100° C. hold 5 min, 320° C. at 20° C./min, 320° C. hold 5 min; det: Agilent 5975B VL MSD; det. temp: 300° C.; scan: 50-500 M/Z. Calibration curves were generated using 1-pentadecene, α(2)-hydroxyhexadecanoic acid, and β(3)-hydroxyhexadecanoic acid dissolved in ethyl acetate and derivatized as described herein.

Figure 21:
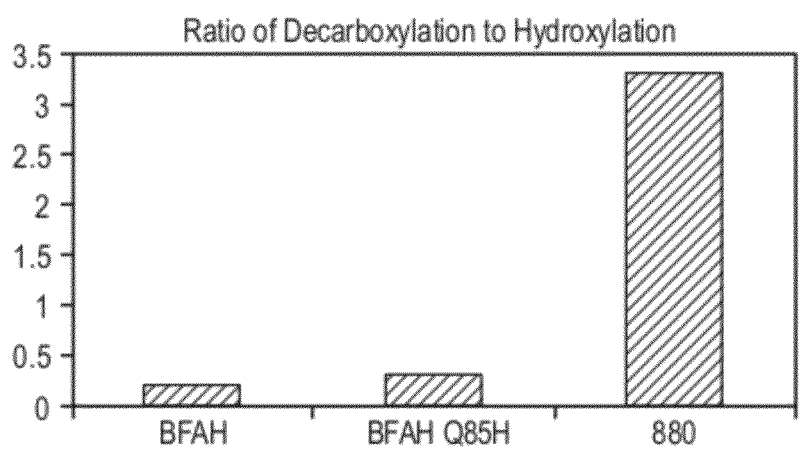
FIG. 21 is a graph demonstrating the ratio of decarboxylation to hydroxylation specific activities for ORF880, CYP152A1, and CYP152A1 Q85H.

Based upon this analysis, product formation was determined to be linear within the first three minutes. The specific activities for each enzyme concentration in the linear range were averaged for a given reaction (e.g., decarboxylation, α-hydroxylation, or β-hydroxylation). FIG. 21 summarizes the results. The specific activity for 1-pentadecene formation was similar for ORF880 and CYP152A1. Mutating the glutamine 85 residue to a histidine increased the specific activity of 1-pentadecene formation (i.e., increased fatty acid decarboxylase activity). This mutation also increased the rate of β-hydroxyhexadecanoic acid formation and lowered the rate of α-hydroxyhexadecanoic acid formation as compared with the wild-type version of CYP152A1. The rate of hydroxyhexadecanoic acid production by ORF880 was about 1/50$^{th}$ of the rates exhibited by the two CYP152A1 enzymes. The ratio of 1-pentadecene formation (i.e. decarboxylation) to hydroxyhexadeconic acid formation (i.e., hydroxylation) activities for each enzyme is given in FIG. 22.

Example 18

Analysis of ORF880 Homolog Activity

As described in Examples 7 through 17, five P450 enzymes were able to convert fatty acids into α-olefins in-vivo and in-vitro, and three of these P450 enzymes were also able to convert fatty acids into β-hydroxy fatty acids (see Table 8). In contrast, two P450 enzymes, *Bacillus claussii* orf_ABC3040 and *Sphingomonas paucimobilis* P450$_{spα}$, were not able to make α-olefins or β-hydroxy fatty acids. These P450 enzymes converted fatty acids only to the corresponding α-hydroxy fatty acids (see Table 8). Consequently, there appears to be a correlation between the ability of a P450 enzyme to hydroxylate fatty acids in the β-position and to decarboxylate fatty acids to the α-olefin, and the inability of a P450 enzyme to decarboxylate fatty acids to α-olefins if the enzyme can only hydroxylate fatty acids in the α-position. In other words, P450 enzymes that hydroxylate fatty acids in the β-position also have the potential to decarboxylate these fatty acids to α-olefins.

Table 8 also demonstrates that when a His or Met is at position 85, the enzyme has the ability to produce α-olefins. Table 8 also shows the percent identity of each enzyme tested relative to *Jeotgalicoccus* sp. 8456 ORF880.

TABLE 8

| ORF880 Homologs Tested | | | | | |
|---|---|---|---|---|---|
| Organism/P450 enzyme | Position 85 [3] | Percent Identity | Makes α-olefin [4] | Makes α-hyFA [4] | Makes β-hyFA [4] |
| *Jeotgalicoccus* sp. 8456 orf880 (fatty acid decarboxylase) | His | 100 | + | − | + |
| *Corynebacterium efficiens* NP_739069 (orf_CE2459) [1] | His | 27 | + | (−) | (−) |
| *Kokuria rhizophila* YP_001856010 (orf_KRH21570) | His | 29 | + | − | + |
| *Bacillus clausii* YP_176535 (orf_ABC3040) | Gln | 37 | − | + | − |
| *Methylobacterium populi* ZP_02200540 (orf_Mpop1292) [2] | Met | 31 | + | − | − |
| *Bacillus subtilis* NP_388092 (α/β-fatty acid hydroxylase, P450$_{Bsβ}$) | Gln | 41 | + | + | + |
| *Sphingomonas paucimobilis* BAA22987 (α-fatty acid hydroxylase, P450$_{Spα}$) | Gln | 36 | − | + | − |

[1] in-vitro experiments with lysate, not with purified protein, difficult to detect hydroxyl fatty acids
[2] poorly expressed in *E. coli*, activity was only detected in-vitro
[3] Relative to the position in ORF880
[4] with hexadecanoic acid as substrate (in-vitro and in-vivo)
hyFA = hydroxy fatty acid Other Embodiments It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant host cell engineered to produce an olefin, comprising a polynucleotide sequence encoding a polypeptide having at least 95% sequence identity to the amino acid sequence of SEQ ID NO: 7, wherein the polypeptide has fatty acid decarboxylase activity.

2. The recombinant host cell of claim 1, wherein the polynucleotide sequence is endogenous to the microorganism.

3. The recombinant host cell of claim 1, wherein the polynucleotide sequence is heterologous to the microorganism.

4. The recombinant host cell of claim 1, wherein the recombinant host cell expresses an increased level of the polypeptide having fatty acid decarboxylase activity relative to a corresponding wild-type host cell.

5. The recombinant host cell of claim 1, wherein a gene encoding an acyl-CoA synthase is attenuated or deleted in the host cell and wherein the host cell expresses a reduced level of an acyl-CoA synthase relative to a corresponding wild type microorganism.

6. The recombinant host cell of claim 5, wherein the acyl-CoA synthase gene is fadD.

7. The recombinant host cell of claim 4, wherein the recombinant host cell is engineered to express, overexpress, or attenuate expression of a thioesterase.

8. A cell culture comprising the recombinant host cell of claim 4, wherein an olefin is produced in the cell culture when the recombinant host cell is cultured in medium containing a substrate under conditions effective to express the polypeptide having fatty acid decarboxylase activity.

9. A cell culture comprising the recombinant host cell of claim 7, wherein an olefin is produced in the cell culture when the recombinant host cell is cultured in medium containing a substrate under conditions effective to express the polypeptide having fatty acid decarboxylase activity.

10. The cell culture of claim 8, wherein the olefin is a terminal olefin.

11. The cell culture of claim 8, wherein the olefin is secreted by the host cell.

12. The cell culture of claim 10, wherein the terminal olefin is selected from the group consisting of a $C_5$-$C_{25}$ terminal olefin, a $C_{13}$-$C_{21}$ terminal olefin, nonadecene, methylnonadecene, heptadecene, methylheptadecene, and pentadecene, an unsaturated terminal olefin, a monounsaturated terminal olefin, a straight chain terminal olefin, a branched chain terminal olefin, and a terminal olefin comprising a cyclic moiety.

13. The cell culture of claim 8, wherein the substrate is a carbon source.

14. The cell culture of claim 13, wherein the carbon source is a fatty acid.

15. The cell culture of claim 13, wherein the carbon source is a carbohydrate.

16. The cell culture of claim 14, wherein the fatty acid is selected from the group consisting of a $C_6$-$C_{26}$ fatty acid, a $C_{14}$-$C_{22}$ fatty acid, tetradecanoic acid, hexadecanoic acid, octadecanoic acid, behenic acid, methyl eicosanoic acid, eicosanoic acid, methyl octadecanoic acid, stearic acid, and palmitic acid, an unsaturated fatty acid, a monounsaturated fatty acid, a saturated fatty acid, a straight chain fatty acid, and a cyclic moiety.

17. A method of producing an olefin comprising culturing the host cell of claim 1, under conditions sufficient to allow expression of the fatty acid decarboxylase polypeptide.

18. The method of claim 17, further comprising culturing the host cell in the presence of at least one biological substrate for the polypeptide.

19. The method of claim 18, further comprising isolating the olefin from the culture medium.

20. An olefin produced by the method of claim 19, wherein the olefin has a $\delta^{13}C$ selected from the group consisting of about −15.4 or greater, about −15.4 to about −10.9, and about −13.92 to about −13.84.

21. An olefin produced by the method of claim 19, wherein the olefin has an $f_M{}^{14}C$ selected from the group consisting of at least about 1.003, at least about 1.01, at least about 1.5, and about 1.111 to about 1.124.

* * * * *